US011571386B2

(12) United States Patent
Worsham

(10) Patent No.: US 11,571,386 B2
(45) Date of Patent: Feb. 7, 2023

(54) METHODS FOR CONTINUOUS MANUFACTURE OF LIPOSOMAL DRUG PRODUCTS

(71) Applicant: Insmed Incorporated, Bridgewater, NJ (US)

(72) Inventor: Robert Worsham, Bridgewater, NJ (US)

(73) Assignee: INSMED INCORPORATED, Bridgewater, NJ (US)

( * ) Notice: Subject to any disclaimer, the term of this patent is extended or adjusted under 35 U.S.C. 154(b) by 309 days.

(21) Appl. No.: 16/981,149

(22) PCT Filed: Mar. 29, 2019

(86) PCT No.: PCT/US2019/024901
§ 371 (c)(1),
(2) Date: Sep. 15, 2020

(87) PCT Pub. No.: WO2019/191627
PCT Pub. Date: Oct. 3, 2019

(65) Prior Publication Data
US 2021/0015750 A1 Jan. 21, 2021

Related U.S. Application Data

(60) Provisional application No. 62/650,372, filed on Mar. 30, 2018.

(51) Int. Cl.
| | | |
|---|---|---|
| *A61K 9/127* | (2006.01) |
| *A61K 31/145* | (2006.01) |
| *A61K 31/4174* | (2006.01) |
| *A61K 31/4196* | (2006.01) |
| *A61K 31/42* | (2006.01) |
| *A61K 31/4375* | (2006.01) |
| *A61K 31/496* | (2006.01) |
| *A61K 31/5025* | (2006.01) |
| *A61K 31/505* | (2006.01) |
| *A61K 31/65* | (2006.01) |
| *A61K 31/7036* | (2006.01) |
| *A61K 31/7048* | (2006.01) |
| *A61K 38/14* | (2006.01) |
| *B01F 23/41* | (2022.01) |
| *B01F 101/22* | (2022.01) |

(52) U.S. Cl.
CPC .......... *A61K 9/1277* (2013.01); *A61K 31/145* (2013.01); *A61K 31/4174* (2013.01); *A61K 31/4196* (2013.01); *A61K 31/42* (2013.01); *A61K 31/4375* (2013.01); *A61K 31/496* (2013.01); *A61K 31/5025* (2013.01); *A61K 31/65* (2013.01); *A61K 31/7036* (2013.01); *A61K 31/7048* (2013.01); *A61K 38/14* (2013.01); *B01F 23/4105* (2022.01); *B01F 2101/22* (2022.01)

(58) Field of Classification Search
None
See application file for complete search history.

(56) References Cited

U.S. PATENT DOCUMENTS

| | | |
|---|---|---|
| 3,091,572 A | 5/1963 | Luedemann et al. |
| 3,136,704 A | 6/1964 | Charney |
| 3,852,557 A | 12/1974 | Brown et al. |
| 4,235,871 A | 11/1980 | Paphadjopoulos et al. |
| 4,372,949 A | 2/1983 | Kodama et al. |
| 4,394,448 A | 7/1983 | Szoka, Jr. et al. |
| 4,396,630 A | 8/1983 | Riedl et al. |
| 4,451,447 A | 5/1984 | Kaplan et al. |
| 4,515,736 A | 5/1985 | Deamer |
| 4,522,803 A | 6/1985 | Lenk et al. |
| 4,547,490 A | 10/1985 | Ecanow et al. |
| 4,588,578 A | 5/1986 | Fountain et al. |
| 4,606,939 A | 8/1986 | Frank et al. |
| 4,684,625 A | 8/1987 | Eppstein et al. |
| 4,693,999 A | 9/1987 | Axelsson et al. |
| 4,721,612 A | 1/1988 | Janoff et al. |
| 4,767,874 A | 8/1988 | Shima et al. |
| 4,833,134 A | 5/1989 | Kishimoto et al. |
| 4,857,311 A | 8/1989 | Domb et al. |
| 4,895,452 A | 1/1990 | Yiournas et al. |
| 4,895,719 A | 1/1990 | Radhakrishnan et al. |
| 4,897,384 A | 1/1990 | Janoff et al. |
| 4,933,121 A | 6/1990 | Law et al. |
| 4,952,405 A | 8/1990 | Yau-Young |
| 4,963,367 A | 10/1990 | Ecanow |
| 4,975,282 A | 12/1990 | Cullis et al. |
| 4,981,692 A | 1/1991 | Popescu et al. |
| 5,000,958 A | 3/1991 | Fountain et al. |
| 5,006,343 A | 4/1991 | Benson et al. |
| 5,008,050 A | 4/1991 | Cullis et al. |
| 5,023,087 A | 6/1991 | Yau-Young |
| 5,030,453 A | 7/1991 | Lenk et al. |

(Continued)

FOREIGN PATENT DOCUMENTS

| | | |
|---|---|---|
| CA | 2174803 A1 | 10/1997 |
| CA | 2101241 C | 12/1998 |

(Continued)

OTHER PUBLICATIONS

Extended European Search Report for European Application No. 19774338.8, dated Nov. 19, 2021, 8 pages.
Extended European Search Report for European Application No. 19797021.3, dated Feb. 22, 2022, 8 pages.
Google Scholar, Amikacin Liposome Inhalation Suspension Ethambutol Search Results, [Online search], Retrieved from the Internet: https://scholar.google.com/scholar?hl=en&as_sdt=0%2C47&q=amikacin+liposome+inhalation+suspension+ethambutol, Retrieved on Jan. 12, 2022, 3 pages.

(Continued)

*Primary Examiner* — Nannette Holloman
(74) *Attorney, Agent, or Firm* — Cooley LLP

(57) ABSTRACT

Provided herein are methods for making liposomal API formulations via continuous in-line diafiltration processes. Also provided herein are liposomal API formulations manufactured by the disclosed methods.

20 Claims, 7 Drawing Sheets

(56) References Cited

U.S. PATENT DOCUMENTS

| | | |
|---|---|---|
| 5,041,278 A | 8/1991 | Janoff et al. |
| 5,049,388 A | 9/1991 | Knight et al. |
| 5,049,389 A | 9/1991 | Radhakrishnan |
| 5,059,421 A | 10/1991 | Loughrey et al. |
| 5,059,591 A | 10/1991 | Janoff et al. |
| 5,077,056 A | 12/1991 | Bally et al. |
| 5,169,637 A | 12/1992 | Lenk et al. |
| 5,178,876 A | 1/1993 | Khokhar et al. |
| 5,192,549 A | 3/1993 | Barenolz et al. |
| 5,211,955 A | 5/1993 | Legros et al. |
| 5,252,339 A | 10/1993 | Cristofori et al. |
| 5,264,618 A | 11/1993 | Felgner et al. |
| 5,269,979 A | 12/1993 | Fountain |
| 5,279,833 A | 1/1994 | Rose |
| 5,316,771 A | 5/1994 | Barenholz et al. |
| 5,320,906 A | 6/1994 | Eley et al. |
| 5,334,761 A | 8/1994 | Gebeyehu et al. |
| 5,401,511 A | 3/1995 | Margalit |
| 5,409,704 A | 4/1995 | Bally et al. |
| 5,415,867 A | 5/1995 | Minchey et al. |
| 5,459,127 A | 10/1995 | Feigner et al. |
| 5,508,269 A | 4/1996 | Smith et al. |
| 5,540,936 A | 7/1996 | Coe et al. |
| 5,543,152 A | 8/1996 | Webb et al. |
| 5,549,102 A | 8/1996 | Lintl et al. |
| 5,569,464 A | 10/1996 | Endo et al. |
| 5,578,320 A | 11/1996 | Janoff et al. |
| 5,580,575 A | 12/1996 | Unger et al. |
| 5,596,982 A | 1/1997 | Blaha-Schnabel |
| 5,610,198 A | 3/1997 | Barry, III et al. |
| 5,614,216 A | 3/1997 | Janoff |
| 5,616,334 A | 4/1997 | Janoff et al. |
| 5,616,341 A | 4/1997 | Mayer et al. |
| 5,631,018 A | 5/1997 | Zalipsky et al. |
| 5,641,662 A | 6/1997 | Debs et al. |
| 5,643,599 A | 7/1997 | Lee et al. |
| 5,662,929 A | 9/1997 | Legace et al. |
| 5,665,383 A | 9/1997 | Grinstaff et al. |
| 5,723,147 A | 3/1998 | Kim et al. |
| 5,736,155 A | 4/1998 | Bally et al. |
| 5,740,966 A | 4/1998 | Blaha-Schnabel |
| 5,741,516 A | 4/1998 | Webb et al. |
| 5,753,613 A | 5/1998 | Ansell et al. |
| 5,756,120 A | 5/1998 | Hersch et al. |
| 5,756,121 A | 5/1998 | Bracken |
| 5,756,353 A | 5/1998 | Debs |
| 5,759,571 A | 6/1998 | Hersch et al. |
| 5,766,627 A | 6/1998 | Sankaram et al. |
| 5,785,987 A | 7/1998 | Hope et al. |
| 5,795,589 A | 8/1998 | Mayer et al. |
| 5,814,335 A | 9/1998 | Webb et al. |
| 5,820,848 A | 10/1998 | Boni et al. |
| 5,823,178 A | 10/1998 | Lloyd |
| 5,837,279 A | 11/1998 | Janoff et al. |
| 5,837,282 A | 11/1998 | Fenske et al. |
| 5,840,702 A | 11/1998 | Bedwell |
| 5,843,473 A | 12/1998 | Woodle et al. |
| 5,849,490 A | 12/1998 | Schonwetter et al. |
| 5,861,159 A | 1/1999 | Pardoll et al. |
| 5,871,710 A | 2/1999 | Bogdanov et al. |
| 5,875,776 A | 3/1999 | Vaghefi |
| 5,883,074 A | 3/1999 | Boggs et al. |
| 5,891,468 A | 4/1999 | Martin et al. |
| 5,922,350 A | 7/1999 | Janoff et al. |
| 5,939,096 A | 8/1999 | Clerc et al. |
| 5,945,122 A | 8/1999 | Abra et al. |
| 5,957,389 A | 9/1999 | Wunderlich et al. |
| 5,958,449 A | 9/1999 | Hersch et al. |
| 5,965,549 A | 10/1999 | Purwar et al. |
| 5,972,379 A | 10/1999 | Guo et al. |
| 5,993,850 A | 11/1999 | Sankaram et al. |
| 6,000,394 A | 12/1999 | Blaha-Schnabel et al. |
| 6,045,828 A | 4/2000 | Bystrom et al. |
| 6,051,251 A | 4/2000 | Zalipsky et al. |
| 6,051,549 A | 4/2000 | Roberts et al. |
| 6,083,530 A | 7/2000 | Mayer et al. |
| 6,085,741 A | 7/2000 | Becker |
| 6,086,851 A | 7/2000 | Boni et al. |
| 6,090,407 A | 7/2000 | Knight et al. |
| 6,093,730 A | 7/2000 | Weidmann et al. |
| 6,106,479 A | 8/2000 | Wunderlich et al. |
| 6,106,858 A | 8/2000 | Ye et al. |
| 6,124,273 A | 9/2000 | Drohan et al. |
| 6,147,060 A | 11/2000 | Zasloff et al. |
| 6,162,462 A | 12/2000 | Bolotin et al. |
| 6,176,237 B1 | 1/2001 | Wunderlich et al. |
| 6,197,333 B1 | 3/2001 | Onyuksel et al. |
| 6,211,162 B1 | 4/2001 | Dale et al. |
| 6,221,385 B1 | 4/2001 | Camu et al. |
| 6,221,388 B1 | 4/2001 | Hersch et al. |
| 6,228,346 B1 | 5/2001 | Zhang et al. |
| 6,228,393 B1 | 5/2001 | DiCosmo et al. |
| 6,235,177 B1 | 5/2001 | Borland et al. |
| 6,274,175 B1 | 8/2001 | Gombotz et al. |
| 6,316,024 B1 | 11/2001 | Allen et al. |
| 6,338,859 B1 | 1/2002 | Leroux et al. |
| 6,348,069 B1 | 2/2002 | Vacant et al. |
| 6,352,996 B1 | 3/2002 | Cao et al. |
| 6,355,267 B1 | 3/2002 | Collins |
| 6,387,886 B1 | 5/2002 | Montgomery et al. |
| 6,419,901 B2 | 7/2002 | Placke et al. |
| 6,440,393 B1 | 8/2002 | Waldrep et al. |
| 6,443,898 B1 | 9/2002 | Unger et al. |
| 6,447,753 B2 | 9/2002 | Edwards et al. |
| 6,451,784 B1 | 9/2002 | Placke et al. |
| 6,458,373 B1 | 10/2002 | Lambert et al. |
| 6,468,532 B1 | 10/2002 | Hsei et al. |
| 6,475,779 B2 | 11/2002 | Mathiowitz et al. |
| 6,481,438 B1 | 11/2002 | Gallem et al. |
| 6,492,560 B2 | 12/2002 | Wilbur et al. |
| 6,497,901 B1 | 12/2002 | Royer |
| 6,509,323 B1 | 1/2003 | Davis et al. |
| 6,511,676 B1 | 1/2003 | Boulikas |
| 6,513,727 B1 | 2/2003 | Jaser et al. |
| 6,518,243 B1 | 2/2003 | Kahne et al. |
| 6,521,211 B1 | 2/2003 | Unger et al. |
| 6,521,736 B2 | 2/2003 | Watterson et al. |
| 6,534,018 B1 | 3/2003 | Baker et al. |
| 6,546,927 B2 | 4/2003 | Litherland et al. |
| 6,554,201 B2 | 4/2003 | Klimowicz et al. |
| 6,596,305 B1 | 7/2003 | Edgerly-Plug |
| 6,599,912 B1 | 7/2003 | Au et al. |
| 6,606,990 B2 | 8/2003 | Stapleton et al. |
| 6,613,352 B2 | 9/2003 | Lagace et al. |
| 6,615,824 B2 | 9/2003 | Power |
| 6,623,671 B2 | 9/2003 | Coe et al. |
| 6,629,646 B1 | 10/2003 | Ivri |
| 6,676,034 B2 | 1/2004 | Tanaka et al. |
| 6,679,251 B1 | 1/2004 | Gallem et al. |
| 6,759,057 B1 | 7/2004 | Weiner et al. |
| 6,770,291 B2 | 8/2004 | Smyth-Templeton et al. |
| 6,843,942 B2 | 1/2005 | Katinger et al. |
| 6,845,770 B2 | 1/2005 | Klimowicz et al. |
| 6,855,296 B1 | 2/2005 | Baker et al. |
| 6,890,555 B1 | 5/2005 | Desai et al. |
| 6,900,184 B2 | 5/2005 | Cohen et al. |
| 6,915,962 B2 | 7/2005 | Power et al. |
| 6,916,490 B1 | 7/2005 | Garver et al. |
| 6,948,491 B2 | 9/2005 | Loeffler et al. |
| 6,962,151 B1 | 11/2005 | Knoch et al. |
| 6,983,747 B2 | 1/2006 | Gallem et al. |
| 6,991,809 B2 | 1/2006 | Anderson |
| 7,059,320 B2 | 6/2006 | Feiner et al. |
| 7,063,860 B2 | 6/2006 | Chancellor et al. |
| 7,077,126 B2 | 7/2006 | Kummer et al. |
| 7,100,600 B2 | 9/2006 | Loeffler et al. |
| 7,104,463 B2 | 9/2006 | Litherland et al. |
| 7,131,440 B2 | 11/2006 | Sonntag |
| 7,244,413 B2 | 7/2007 | Barbera-Guillem |
| 7,252,085 B2 | 8/2007 | Kunschir |
| 7,255,106 B2 | 8/2007 | Gallem et al. |
| 7,297,344 B1 | 11/2007 | Fleischer et al. |
| 7,331,339 B2 | 2/2008 | Smith et al. |
| 7,368,102 B2 | 5/2008 | Tarara et al. |

(56) References Cited

U.S. PATENT DOCUMENTS

| | | |
|---|---|---|
| D583,928 S | 12/2008 | Knoch |
| 7,458,372 B2 | 12/2008 | Feiner et al. |
| 7,472,701 B2 | 1/2009 | Pfichner et al. |
| 7,544,369 B2 | 6/2009 | Boni et al. |
| 7,600,511 B2 | 10/2009 | Power et al. |
| 7,686,014 B2 | 3/2010 | Boehm et al. |
| 7,718,189 B2 | 5/2010 | Boni et al. |
| 7,748,377 B2 | 7/2010 | Smith et al. |
| 7,758,886 B2 | 7/2010 | Jauernig et al. |
| 7,771,642 B2 | 8/2010 | Power et al. |
| 7,779,838 B2 | 8/2010 | Hetzer et al. |
| 7,879,351 B2 | 2/2011 | Li et al. |
| 7,891,352 B2 | 2/2011 | Gallem et al. |
| 7,931,212 B2 | 4/2011 | Urich et al. |
| D638,117 S | 5/2011 | Eckstein et al. |
| 7,958,887 B2 | 6/2011 | Kelliher et al. |
| 7,971,588 B2 | 7/2011 | Fink et al. |
| 7,980,247 B2 | 7/2011 | Boehm et al. |
| 3,006,698 A1 | 8/2011 | Boehm et al. |
| 8,071,127 B2 | 12/2011 | Cipolla et al. |
| D652,908 S | 1/2012 | Eckstein et al. |
| 8,100,162 B2 | 1/2012 | Joern et al. |
| 8,113,194 B2 | 2/2012 | Boehm et al. |
| 8,119,156 B2 | 2/2012 | Cipolla et al. |
| D656,604 S | 3/2012 | Eckstein et al. |
| 8,226,975 B2 | 7/2012 | Weers |
| 8,263,645 B2 | 9/2012 | Keller |
| 8,268,347 B1 | 9/2012 | Cipolla et al. |
| 8,333,187 B2 | 12/2012 | Gallem et al. |
| 8,342,171 B2 | 1/2013 | Boehm et al. |
| 8,347,873 B2 | 1/2013 | Schuschnig et al. |
| 8,387,895 B2 | 3/2013 | Stangl |
| 8,398,001 B2 | 3/2013 | Borland et al. |
| D680,214 S | 4/2013 | Eckstein et al. |
| 8,414,915 B2 | 4/2013 | Cipolla et al. |
| 8,459,252 B2 | 6/2013 | Gallem et al. |
| 8,511,581 B2 | 8/2013 | Urich et al. |
| 8,596,264 B2 | 12/2013 | Sommer |
| 8,616,195 B2 | 12/2013 | Power et al. |
| 8,632,804 B2 | 1/2014 | Weers |
| 8,642,075 B2 | 2/2014 | Weers |
| 8,671,933 B2 | 3/2014 | Boehm et al. |
| 8,673,348 B2 | 3/2014 | Weers |
| 8,673,349 B2 | 3/2014 | Weers |
| 8,679,532 B2 | 3/2014 | Weers |
| 8,720,432 B2 | 5/2014 | Borgschulte et al. |
| 8,720,435 B2 | 5/2014 | Gallem et al. |
| 8,739,777 B2 | 6/2014 | Kreutzmann et al. |
| 8,802,137 B2 | 8/2014 | Boni et al. |
| 8,985,100 B2 | 3/2015 | Minocchieri et al. |
| 9,016,272 B2 | 4/2015 | Gallem et al. |
| 9,027,548 B2 | 5/2015 | Borgschulte et al. |
| 9,028,864 B2 | 5/2015 | Cipolla et al. |
| 9,046,092 B2 | 6/2015 | Boehm et al. |
| 9,061,303 B2 | 6/2015 | Waldner et al. |
| 9,072,464 B2 | 7/2015 | Haartsen et al. |
| 9,078,897 B1 | 7/2015 | Cipolla et al. |
| 9,084,862 B2 | 7/2015 | Blakey et al. |
| 9,095,676 B2 | 8/2015 | Gallem et al. |
| 9,108,211 B2 | 8/2015 | Ivri |
| 9,114,081 B2 | 8/2015 | Gupta |
| 9,119,783 B2 | 9/2015 | Gupta |
| 9,119,930 B2 | 9/2015 | Kreutzmann et al. |
| 9,149,588 B2 | 10/2015 | Gordon et al. |
| 9,161,963 B2 | 10/2015 | Keller et al. |
| 9,168,556 B2 | 10/2015 | Pumm et al. |
| 9,198,859 B2 | 12/2015 | Keller et al. |
| 9,259,424 B2 | 2/2016 | Cipolla et al. |
| 9,265,900 B2 | 2/2016 | Loenner et al. |
| 9,333,214 B2 | 5/2016 | Gupta |
| 9,402,845 B2 | 8/2016 | Weers |
| 9,511,082 B2 | 12/2016 | Weers |
| 9,549,925 B2 | 1/2017 | Weers |
| 9,549,939 B2 | 1/2017 | Weers |
| 9,566,234 B2 | 2/2017 | Perkins et al. |
| 9,724,301 B2 | 8/2017 | Gupta |
| 9,737,555 B2 | 8/2017 | Gupta |
| 9,827,317 B2 | 11/2017 | Boni et al. |
| 9,895,385 B2 | 2/2018 | Eagle et al. |
| 9,925,205 B2 | 3/2018 | Malinin |
| 10,064,882 B2 | 9/2018 | Gupta |
| 10,124,066 B2 | 11/2018 | Perkins et al. |
| 10,238,675 B2 | 3/2019 | Eagle et al. |
| 10,251,900 B2 | 4/2019 | Eagle et al. |
| 10,328,071 B2 | 6/2019 | Weers |
| 10,398,719 B2 | 9/2019 | Eagle et al. |
| 10,471,149 B2 | 11/2019 | Perkins et al. |
| 10,588,918 B2 | 3/2020 | Eagle et al. |
| 10,751,355 B2 | 8/2020 | Eagle et al. |
| 10,828,314 B2 | 11/2020 | Eagle et al. |
| 2001/0006660 A1 | 7/2001 | Legace et al. |
| 2002/0035061 A1 | 3/2002 | Krieger et al. |
| 2002/0039596 A1 | 4/2002 | Hartounian et al. |
| 2002/0052390 A1 | 5/2002 | Ponikau |
| 2002/0086852 A1 | 7/2002 | Cantor et al. |
| 2002/0187105 A1 | 12/2002 | Zou et al. |
| 2003/0039615 A1 | 2/2003 | Katz |
| 2003/0059375 A1 | 3/2003 | Perez-Soler et al. |
| 2003/0096774 A1 | 5/2003 | Gonda et al. |
| 2003/0099697 A1 | 5/2003 | Panzner et al. |
| 2003/0118636 A1 | 6/2003 | Friesen et al. |
| 2003/0138481 A1 | 7/2003 | Zadi |
| 2003/0148964 A1 | 8/2003 | Dunne |
| 2003/0224039 A1 | 12/2003 | Boni et al. |
| 2004/0009126 A1 | 1/2004 | Pilkiewicz et al. |
| 2004/0032037 A1 | 2/2004 | Katinger et al. |
| 2004/0089295 A1 | 5/2004 | Gallem et al. |
| 2004/0091541 A1 | 5/2004 | Unger |
| 2004/0101553 A1 | 5/2004 | Lee et al. |
| 2004/0142025 A1 | 7/2004 | MacLachlan et al. |
| 2004/0142026 A1 | 7/2004 | Boni et al. |
| 2004/0156888 A1 | 8/2004 | Jensen et al. |
| 2004/0180082 A1 | 9/2004 | Kang et al. |
| 2005/0019926 A1 | 1/2005 | Gonda et al. |
| 2005/0025822 A1 | 2/2005 | Wong et al. |
| 2005/0042341 A1 | 2/2005 | Thomas et al. |
| 2005/0113337 A1 | 5/2005 | Taneja et al. |
| 2005/0119202 A1 | 6/2005 | Kreutzer et al. |
| 2005/0207987 A1 | 9/2005 | Speirs et al. |
| 2005/0214224 A1 | 9/2005 | Weers et al. |
| 2005/0217666 A1 | 10/2005 | Fink et al. |
| 2005/0220752 A1 | 10/2005 | Charmot et al. |
| 2005/0249795 A1 | 11/2005 | Zhang et al. |
| 2006/0062738 A1 | 3/2006 | Hofmann et al. |
| 2006/0067998 A1 | 3/2006 | Kurzrock et al. |
| 2006/0073198 A1 | 4/2006 | Boni et al. |
| 2006/0110441 A1 | 5/2006 | Wong et al. |
| 2006/0198940 A1 | 9/2006 | McMorrow |
| 2006/0217603 A1 | 9/2006 | Nagai et al. |
| 2006/0286038 A1 | 12/2006 | Rairkar et al. |
| 2007/0065367 A1 | 3/2007 | Condos et al. |
| 2007/0077290 A1 | 4/2007 | Li et al. |
| 2007/0081963 A1 | 4/2007 | Oh et al. |
| 2007/0105758 A1 | 5/2007 | May et al. |
| 2007/0196461 A1 | 8/2007 | Weers |
| 2007/0267010 A1 | 11/2007 | Fink et al. |
| 2008/0089927 A1 | 4/2008 | Malinin |
| 2008/0108104 A1 | 5/2008 | Eckstein et al. |
| 2008/0131497 A1 | 6/2008 | Perkins et al. |
| 2008/0246472 A1 | 10/2008 | Igney et al. |
| 2009/0053489 A1 | 2/2009 | Yamamura et al. |
| 2009/0104256 A1 | 4/2009 | Gupta |
| 2009/0104257 A1 | 4/2009 | Li et al. |
| 2009/0105126 A1 | 4/2009 | Li et al. |
| 2009/0269396 A1 | 10/2009 | Cipolla et al. |
| 2009/0274754 A1 | 11/2009 | Cipolla et al. |
| 2010/0068257 A1 | 3/2010 | Boni et al. |
| 2010/0196455 A1 | 8/2010 | Malinin |
| 2010/0260829 A1 | 10/2010 | Boni et al. |
| 2011/0064796 A1 | 3/2011 | Cipolla et al. |
| 2011/0150983 A1 | 6/2011 | Cipolla et al. |
| 2011/0159079 A1 | 6/2011 | Li et al. |
| 2011/0256175 A1 | 10/2011 | Hope et al. |
| 2012/0010162 A1 | 1/2012 | Norling |

(56) References Cited

U.S. PATENT DOCUMENTS

| | | |
|---|---|---|
| 2012/0077786 A1 | 3/2012 | Byron et al. |
| 2012/0192861 A1 | 8/2012 | Surber |
| 2012/0244206 A1 | 9/2012 | Cipolla et al. |
| 2013/0028960 A1 | 1/2013 | Weers |
| 2013/0034534 A1 | 2/2013 | Kroneberg et al. |
| 2013/0052260 A1 | 2/2013 | Weers |
| 2013/0064883 A1 | 3/2013 | Weers |
| 2013/0071468 A1 | 3/2013 | Weers |
| 2013/0071469 A1 | 3/2013 | Weers |
| 2013/0087480 A1 | 4/2013 | Stark et al. |
| 2013/0089598 A1 | 4/2013 | Gupta |
| 2013/0121918 A1 | 5/2013 | Hong et al. |
| 2013/0136788 A1 | 5/2013 | Gupta |
| 2013/0177629 A1 | 7/2013 | Martin et al. |
| 2013/0280174 A1 | 10/2013 | Lipic et al. |
| 2013/0330400 A1 | 12/2013 | Perkins et al. |
| 2013/0330440 A1 | 12/2013 | Fulgham |
| 2014/0018431 A1 | 1/2014 | Wade et al. |
| 2014/0072620 A1 | 3/2014 | Weers |
| 2014/0248335 A1 | 9/2014 | Malinin |
| 2014/0308304 A1 | 10/2014 | Manoharan et al. |
| 2014/0314835 A1 | 10/2014 | Boni et al. |
| 2014/0371293 A1 | 12/2014 | Brown et al. |
| 2015/0110855 A1 | 4/2015 | Cipolla et al. |
| 2015/0272880 A1 | 10/2015 | Seidel et al. |
| 2015/0283076 A1 | 10/2015 | Cipolla et al. |
| 2015/0283133 A1 | 10/2015 | Gonda et al. |
| 2015/0306173 A1 | 10/2015 | Chen et al. |
| 2015/0314002 A1 | 11/2015 | Perkins et al. |
| 2015/0328244 A1 | 11/2015 | Eagle et al. |
| 2016/0113927 A1 | 4/2016 | Weers |
| 2016/0120806 A1 | 5/2016 | Cipolla et al. |
| 2016/0143849 A1 | 5/2016 | Gupta |
| 2016/0151402 A1 | 6/2016 | Gupta |
| 2016/0184301 A1 | 6/2016 | Weers |
| 2016/0184302 A1 | 6/2016 | Weers |
| 2016/0271125 A1 | 9/2016 | Boni et al. |
| 2016/0317563 A1 | 11/2016 | Weers |
| 2016/0317564 A1 | 11/2016 | Weers |
| 2016/0354371 A1 | 12/2016 | Weers |
| 2017/0014342 A1 | 1/2017 | Li et al. |
| 2017/0087155 A1 | 3/2017 | Weers |
| 2017/0100420 A1 | 4/2017 | Boni et al. |
| 2017/0165374 A1 | 6/2017 | Perkins et al. |
| 2017/0196900 A1 | 7/2017 | Perkins et al. |
| 2017/0360816 A1 | 12/2017 | Eagle et al. |
| 2017/0360818 A1 | 12/2017 | Gupta |
| 2018/0104345 A1 | 4/2018 | Boni et al. |
| 2018/0153918 A1 | 6/2018 | Weers |
| 2018/0169124 A1 | 6/2018 | Boni et al. |
| 2018/0185401 A1 | 7/2018 | Eagle et al. |
| 2018/0200186 A1 | 7/2018 | Chen et al. |
| 2018/0311267 A1 | 11/2018 | Eagle et al. |
| 2018/0318326 A1 | 11/2018 | Boni et al. |
| 2018/0318327 A1 | 11/2018 | Boni et al. |
| 2018/0360864 A1 | 12/2018 | Perkins et al. |
| 2019/0008970 A1 | 1/2019 | Boni et al. |
| 2019/0022232 A1 | 1/2019 | Perkins et al. |
| 2019/0142854 A1 | 5/2019 | Boni et al. |
| 2019/0160086 A1 | 5/2019 | Eagle et al. |
| 2019/0160087 A1 | 5/2019 | Boni et al. |
| 2019/0201534 A1 | 7/2019 | Boni et al. |
| 2019/0216834 A1 | 7/2019 | Eagle et al. |
| 2020/0009171 A1 | 1/2020 | Eagle et al. |
| 2020/0268781 A1 | 8/2020 | Eagle et al. |
| 2020/0345754 A1 | 11/2020 | Eagle et al. |
| 2020/0390758 A1 | 12/2020 | Weers |
| 2021/0113467 A1 | 4/2021 | Worsham |
| 2021/0121574 A1 | 4/2021 | Boni et al. |
| 2021/0228606 A1 | 7/2021 | Eagle et al. |
| 2021/0369752 A1 | 12/2021 | Perkins et al. |
| 2022/0016150 A1 | 1/2022 | Boni et al. |

FOREIGN PATENT DOCUMENTS

| | | |
|---|---|---|
| CA | 2215716 C | 12/1999 |
| CA | 2614764 | 1/2007 |
| CA | 2838111 | 6/2007 |
| CN | 1747738 | 3/2006 |
| EP | 0069307 | 1/1983 |
| EP | 0274431 | 5/1994 |
| EP | 0652008 | 5/1995 |
| EP | 1083881 | 3/2001 |
| EP | 1083886 | 3/2001 |
| EP | 1190705 | 3/2002 |
| EP | 1332755 A1 | 8/2003 |
| EP | 0825852 | 7/2004 |
| EP | 1559431 A1 | 8/2005 |
| EP | 2199298 A1 | 6/2010 |
| EP | 2457609 | 5/2012 |
| GB | 2145107 | 3/1985 |
| JP | S63-500175 | 1/1988 |
| JP | S63-239213 | 10/1988 |
| JP | 6-345663 | 12/1994 |
| JP | H10-511363 | 11/1998 |
| JP | 11-080022 | 3/1999 |
| JP | 2002-318193 | 10/2002 |
| JP | 2006-028069 | 2/2006 |
| JP | 2006-514016 | 4/2006 |
| JP | 2006-514682 | 5/2006 |
| JP | 2008-531197 | 8/2008 |
| JP | 2015-517576 | 6/2015 |
| UA | 27298 | 10/2007 |
| UA | 27804 | 11/2007 |
| WO | WO 85/00968 | 3/1985 |
| WO | WO 85/04578 | 10/1985 |
| WO | WO 86/06959 | 12/1986 |
| WO | WO 87/00043 | 1/1987 |
| WO | WO 87/02219 | 4/1987 |
| WO | WO 88/04573 | 6/1988 |
| WO | WO-8900846 A1 | 2/1989 |
| WO | WO 91/09616 | 7/1991 |
| WO | WO 91/16882 | 11/1991 |
| WO | WO 93/12240 | 6/1993 |
| WO | WO 94/12155 | 6/1994 |
| WO | WO 94/12156 | 6/1994 |
| WO | WO 94/22430 | 10/1994 |
| WO | WO 96/08235 | 3/1996 |
| WO | WO 96/19199 | 6/1996 |
| WO | WO 96/19972 | 7/1996 |
| WO | WO 1996/037194 | 11/1996 |
| WO | WO 97/29851 | 8/1997 |
| WO | WO 99/30686 | 6/1999 |
| WO | WO 99/51202 | 10/1999 |
| WO | WO 99/61003 | 12/1999 |
| WO | WO 99/65466 | 12/1999 |
| WO | WO 00/27359 | 5/2000 |
| WO | WO 00/29103 | 5/2000 |
| WO | WO 00/45791 | 8/2000 |
| WO | WO 01/00173 | 1/2001 |
| WO | WO 01/05373 | 1/2001 |
| WO | WO 01/15678 | 3/2001 |
| WO | WO 01/18280 | 3/2001 |
| WO | WO 01/32246 | 5/2001 |
| WO | WO 2002/032400 | 4/2002 |
| WO | WO 2002/043699 | 6/2002 |
| WO | WO 2003/045965 | 6/2003 |
| WO | WO 2003/075889 | 9/2003 |
| WO | WO 2003/075890 | 9/2003 |
| WO | WO 2004/002453 | 1/2004 |
| WO | WO 2004/047802 | 6/2004 |
| WO | WO 2004/054499 | 7/2004 |
| WO | WO 2004/091623 | 10/2004 |
| WO | WO 2004/110346 | 12/2004 |
| WO | WO 2004/110493 | 12/2004 |
| WO | WO 2005/019472 | 3/2005 |
| WO | WO 2006/096303 | 9/2006 |
| WO | WO 2006/108556 | 10/2006 |
| WO | WO 2007/011940 | 1/2007 |
| WO | WO 2007/012191 | 2/2007 |
| WO | WO 2007/067520 | 6/2007 |
| WO | WO 2007/117509 | 10/2007 |

(56) References Cited

FOREIGN PATENT DOCUMENTS

| | | |
|---|---|---|
| WO | WO 2007/117550 | 10/2007 |
| WO | WO 2008/039989 | 4/2008 |
| WO | WO 2008/063341 | 5/2008 |
| WO | WO 2008/137717 | 11/2008 |
| WO | WO 2008/137917 | 11/2008 |
| WO | WO 2009/045116 | 4/2009 |
| WO | WO 2009/055568 | 4/2009 |
| WO | WO 2009/055571 | 4/2009 |
| WO | WO 2009/126502 | 10/2009 |
| WO | WO 2010/045209 | 4/2010 |
| WO | WO 2010/111641 | 9/2010 |
| WO | WO 2011/050206 | 4/2011 |
| WO | WO 2011/108955 | 9/2011 |
| WO | WO 2011/153323 | 12/2011 |
| WO | WO 2012/050945 | 4/2012 |
| WO | WO 2012/069531 | 5/2012 |
| WO | WO 2012/159103 | 11/2012 |
| WO | WO 2012/168181 | 12/2012 |
| WO | WO 2013/086373 | 6/2013 |
| WO | WO 2013/177226 | 11/2013 |
| WO | WO 2014/025890 | 2/2014 |
| WO | WO 2014/052634 | 4/2014 |
| WO | WO 2014/085526 | 6/2014 |
| WO | WO 2015/017807 | 2/2015 |
| WO | WO 2015/175939 | 11/2015 |
| WO | WO 2016/033546 | 3/2016 |
| WO | WO 2016/149625 | 9/2016 |
| WO | WO 2017/008076 | 1/2017 |

OTHER PUBLICATIONS

Google Scholar, Amikacin Liposome Inhalation Suspension Search Results, [Online search], Retrieved from the Internet: https://scholar.google.com/scholar?hl=en&as_sdt=0%2C47&q=amikacin+liposome+inhalation+suspension, Retrieved on Jan. 12, 2022, 3 pages.
Olivier, K. N. et al., "Randomized Trial of Liposomal Amikacin for Inhalation in Nontuberculous Mycobacterial Lung Disease", American Journal of Respiratory and Critical Care Medicine, Mar. 2017, vol. 195, Issue 6, pp. 814-823, with supplemental data.
International Search Report and Written Opinion for International Application No. PCT/US2008/062469, dated Sep. 18, 2008, 9 pages.
International Preliminary Report on Patentability for International Application No. PCT/US2008/062469, dated Nov. 10, 2009, 7 pages.
International Search Report and Written Opinion for International Application No. PCT/US2008/062868, dated Sep. 18, 2008, 7 pages.
International Preliminary Report on Patentability for International Application No. PCT/US2008/062868, dated Nov. 10, 2009, 5 pages.
Supplementary European Search Report for European Application No. 09821103.0, dated Aug. 12, 2015, 10 pages.
Written Opinion for International Application No. PCT/US2009/060468, dated Jun. 24, 2010, 3 pages.
International Preliminary Report on Patentability for International Application No. PCT/US2009/060468, dated Apr. 19, 2011, 4 pages.
Supplementary European Search Report for European Application No. 08840993.3, dated Aug. 22, 2013, 6 pages.
International Preliminary Report on Patentability for International Application No. PCT/US2008/080954, dated Apr. 27, 2010, 6 pages.
International Search Report and Written Opinion for International Application No. PCT/US2008/080954, dated Jul. 17, 2009, 8 pages.
Supplementary European Search Report for European Application No. 03816990.0, dated Jan. 12, 2009, 5 pages.
International Search Report for International Application No. PCT/US2003/034240, dated Jul. 12, 2005, 1 page.
International Preliminary Report on Patentability for International Application No. PCT/US2003/034240, dated May 6, 2013, 5 pages.
Supplementary European Search Report for European Application No. 06787716.7, dated Dec. 29, 2011, 7 pages.
Generics [UK] Ltd.'s Notice of Opposition for European Application No. 06787716.7, filed Jun. 4, 2014, 17 pages.
Patentee's Response to Notice of Opposition and Declaration of Lee Leserman for European Application No. 06787716.7, filed Jan. 16, 2015, 58 pages.
International Search Report and Written Opinion for International Application No. PCT/US2006/027859, dated Aug. 14, 2007, 8 pages.
International Preliminary Report on Patentability for International Application No. PCT/US2006/027859, dated Jan. 22, 2008, 6 pages.
Supplementary European Search Report for European Application No. 07754853, dated Jan. 16, 2013, 8 pages.
International Search Report and Written Opinion for International Application No. PCT/US2007/008404, dated Sep. 26, 2008, 6 pages.
International Preliminary Report on Patentability for International Application No. PCT/US2007/008404, dated Oct. 21, 2008, 4 pages.
European Search Report for European Patent Application No. 11159754.8, dated Jun. 22, 2011, 5 pages.
European Search Report for European Patent Application No. 13175824.5, dated Sep. 16, 2013, 8 pages.
European Search Report for European Application No. 14183066.1, dated Dec. 16, 2014, 11 pages.
Supplementary European Search Report for European Application No. 06847502.9, dated Dec. 5, 2012, 7 pages.
International Search Report and Written Opinion for International Application No. PCT/US2006/046360, dated Oct. 17, 2007, 5 pages.
International Preliminary Report on Patentability for International Application No. PCT/US2006/046360, dated Jun. 11, 2008, 5 pages.
European Search Report for European Application No. 16156100.6, dated Jul. 25, 2016, 6 pages.
European Search Report for European Application No. 16156099.0, dated Jul. 25, 2016, 7 pages.
Supplementary European Search Report and Written Opinion for European Application No. 07754936.8, dated Jan. 18, 2013, 9 pages.
International Search Report and Written Opinion for International Application No. PCT/US2007/008500, dated Sep. 26, 2008, 9 pages.
International Preliminary Report on Patentability for International Application No. PCT/US2007/008500, dated Oct. 21, 2008, 8 pages.
Supplementary European Search Report for European Application No. 13793204.2, dated Sep. 25, 2015, 5 pages.
International Search Report and Written Opinion for International Application No. PCT/US2013/042113, dated Sep. 4, 2013, 13 pages.
International Preliminary Report on Patentability for International Application No. PCT/US2013/042113, dated Nov. 25, 2014, 9 pages.
Supplementary European Search Report for European Application No. 13858844.7, dated Jun. 15, 2016, 4 pages.
International Search Report and Written Opinion for International Application No. PCT/US2013/072136, dated Feb. 12, 2014, 15 pages.
International Search Report and Written Opinion for International Application No. PCT/US2015/031079, dated Aug. 5, 2015, 9 pages.
Extended European Search Report for European Application No. 15791964.8, dated Dec. 11, 2017, 10 pages.
International Search Report and Written Opinion for International Application No. PCT/US2016/041776, dated Sep. 16, 2016, 9 pages.
International Search Report and Written Opinion for International Application No. PCT/US2019/024901, dated Jun. 12, 2019, 12 pages.

(56) References Cited

OTHER PUBLICATIONS

Worsham, R. D. et al., "Potential of continuous manufacturing for liposomal drug products," Biotechnology Journal, vol. 14, No. 2. pp. 1-8 (2019).
International Search Report and Written Opinion for International Application No. PCT/US2016/062894, dated Jan. 31, 2017, 10 pages.
U.S. Appl. No. 60/748,468, filed Dec. 8, 2005, entitled "Lipid-based compositions of antiinfectives for treating pulmonary infections and methods of use," 26 pages.
United States Patent and Trademark Office, Before The Patent Trial and Appeal Board, *Aradigm Corporation v. Insmed Incorporated*, Case PGR2017-00021; U.S. Pat. No. 9,402,845, Petition for Post Grant Review, filed May 1, 2017, 111 pages.
United States Patent and Trademark Office, Before The Patent Trial and Appeal Board, *Aradigm Corporation v. Insmed Incorporated*, Case PGR2017-00021; U.S. Pat. No. 9,402,845, Declaration of A. Bruce Montgomery, M.D. dated May 1, 2017, Aradigm Exhibit 1020, 146 pages.
United States Patent and Trademark Office, Before The Patent Trial and Appeal Board, *Aradigm Corporation v. Insmed Incorporated*, Case PGR2017-00021; U.S. Pat. No. 9,402,845, Patent Owner's Preliminary Response, filed Aug. 16, 2017, 84 pages.
United States Patent and Trademark Office, Before The Patent Trial and Appeal Board, *Aradigm Corporation v. Insmed Incorporated*, Case PGR2017-00021; U.S. Pat. No. 9,402,845, Declaration of Robert J. Lee, Ph.D. In Support Of Patent Owner Insmed's Preliminary Response, dated Aug. 16, 2017, 92 pages.
Amikacin—DrugBank Accession No. DB00479 (APRD00550) [online], <https://www.drugbank.ca/drugs/DB00479>. Retrieved on Apr. 14, 2017, 10 pages.
The Asthma Center Education and Research Fund, Nebulizer Instructions [online], <http://www.theasthmacenter.org/index.php/disease_information/asthma/using_special_devices/nebulizer_instructions/>. Retrieved on Apr. 14, 2017, 1 page.
Ciprofloxacin—DrugBank, Accession No. DB00537 (APRD00424, EXPT00999) [online], <https://www.drugbank.ca/drugs/DB00537>. Retrieved on Apr. 14, 2017, 19 pages.
Prosecution history for U.S. Pat. No. 9,402,845, issued Aug. 2, 2016 (excerpted), 430 pages.
Allen, T. M. et al., "Effect of liposome size and drug release properties of pharmacokinetics of encapsulated drug to rats," The Journal of Pharmacology and Experimental Therapeutics, 226(2):539-544 (1983).
Alton et al., "Cationic lipid-mediated CFTR gene transfer to the lungs and nose of patients with cystic fibrosis: a double-blind placebo-controlled trial," The Lancet, 353(9157):947-954 (1999).
Anacona et al., "Synthesis and antibacterial activity of metal complexes of ciprofloxacin," Transition Metal Chemistry (2001) 26:228-231.
Andrews, J. M., "Determination of minimum inhibitory concentrations," Journal of Antimicrobial Chemotherapy, 48(S1):5-14 (2001).
Antos, M. et al., "Antibacterial activity of liposomal amikacin against Pseudomonas aeruginosa in vitro," Pharmacological Research, 32(1/2):84-87 (1995).
Bakker-Woudenberg, I. et al., "Efficacy of gentamicin or ceftazidine entrapped in liposomes with prolonged blood circulation and enhanced localization in Klebsiella pneumoniae-infected lung tissue," The Journal Infectious Diseases, 171:938-947 (1995).
Bakker-Woudenberg, I. A. J. M. et al., "Long-Circulating Sterically Stabilized Liposomes in the Treatment of Infections," Method in Enzymology, Available online Feb. 21, 2005, 391:228-260 (2005).
Bakker-Woudenberg et al. (2002). Ciprofloxacin in polyethylene glycol-coated liposomes: efficacy in rat models of acute or chronic Pseudomonas aeruginosa infection. Antimicrobial Agents and Chemotherapy 46(8):2575-2581.
Bakker-Woudenberg et al. (2001). Improved efficacy of ciprofloxacin administered in polyethylene glycol-coated liposomes for treatment of *Klebsiella pneumoniae* pneumonia in rats. Antimicrobial Agents and Chemotherapy 45(5), pp. 1487-1492.

Ball, V. et al., "Complexation mechanism of bovine serum albumin and poly(allylamine hydrochloride)," J. Phys. Chem. B 106(9):2357-2364 (2002).
Bangham, A. D. et al., "Diffusion of univalent ions across the lamellae of swollen phospholipids," J. Mol. Biol., 13(1):238-252 (1965).
Bangham, A. D., Introduction, "Liposomes: An Historical Perspective," in: Liposomes, Ostro, M. J. (ed.), pp. 1-25, Marcel Dekker, Inc., New York (1983).
Bargoni, A. et al., "Transmucosal transport of tobramycin incorporated in solid lipid nanoparticles (SLN) after duodenal administration to rats. Part II—Tissue distribution," Pharmacological Research, 43(5):497-502 (2001).
Beaulac, C. et al., "Eradication of Mucoid Pseudomonas aeruginosa with Fluid Liposome-Encapsulated Tobramycin in an Animal Model of Chronic Pulmonary Infection," Antimicrobial Agents and Chemotherapy, 40(3):665-669 (1996).
Beaulac, C. et al., "In-vitro bactericidal efficacy of sub-MIC concentrations of liposome-encapsulated antibiotic against Gram-negative and Gram-positive bacteria," Journal of Antimicrobial Chemotherapy, 41:35-41 (1998).
Beaulac, C. et al., "Aerolization of low phase transition temperature liposomal tobramycin as a dry powder in an animal model of chronic pulmonary infection caused by Pseudomonas aeruginosa," Journal Drug Targeting, 7(1):33-41 (1999).
Beaulac, C. et al., "In vitro kinetics of drug release and pulmonary retention of microencapsulated antibiotic in liposomal formulations in relation to the lipid composition," Journal Microencapsulation 14(3):335-348 (1997).
Bedard et al. (1989). Interaction of the fluoroquinolone antimicrobial agents ciprofloxacin and enoxacin with liposomes. Antimicrobial Agents and Chemotherapy 33(8), pp. 1379-1382.
Bermudez, L. E. et al., "Treatment of disseminated mycobacterium avium complex infection of beige mice with liposome-encapsulated aminoglycosides," The Journal of Infectious Diseases, 161(6):1262-1268 (1990).
Betageri et al., Liposome Drug Delivery Systems, (Technomic Publishing Co. ed., 1993) (excerpted), 32 pages.
Bhavane, R. et al., "Agglomerated vesicle technology: a new class of particles for controlled and modulated pulmonary drug delivery," Journal of Controlled Release 93(1):15-28 (Nov. 2003).
Bhavane (2006). Nanoparticle agglomerates for pulmonary drug delivery. A dissertation presented to the faculty of the University of Texas Health Science Center at Houston of Health Information Sciences. UMI No. 3237380, 160 pages.
Biller, J. A. et al., "Efficacy Of Liposomal Amikacin For Inhalation (LAI) In Achieving Nontuberculous Mycobacteria (NTM) Culture Negativity In Patients Whose Lung Infection Is Refractory To Guideline-Based Therapy," Poster presented at the ATS 2015 International Conference, May 15-20, 2015, Denver, CO, USA, 1 page.
Biller, J. A. et al., "Efficacy Of Liposomal Amikacin For Inhalation (LAI) In Achieving Nontuberculous Mycobacteria (NTM) Culture Negativity In Patients Whose Lung Infection Is Refractory To Guideline-Based Therapy," Abstract, D108 Diagnosis and Management of Nontuberculous Mycobacteria Infections, Poster Discussion Session, May 20, 2015, Colorado Convention Center, Am J Respir Crit Care Med 191;2015:A6295, Online Abstracts Issue, 1 page.
Bilodeau, M. et al., "Kanamycin aerosol therapy in 200 cases of bronchopulmonary suppurations," Can. Med. Assoc. J., 89:537-541 (1963) (with English Abstract).
Blaser, J. et al., "Once daily dosing of aminoglycosides," Eur. Clin. Microbiol. Infect. Dis., 14(12):1029-1038 (1995).
Bolotin, E. M. et al., "Ammonium Sulfate Gradients for Efficient and Stable Remote Loading of Amphipathic Weak Bases into Liposomes and Ligandoliposomes," Journal of Liposome Research, vol. 4(1), 1994, pp. 455-479.
Bruinenberg, P. et al., "Inhaled Liposomal Ciprofloxacin: Once a Day Management of Respiratory Infections," Respiratory Drug Delivery, 1:73-82 (2010).
Bruinenberg, P., "Safety, tolerability and pharmacokinetics of novel liposomal ciprofloxacin of novel liposomal ciprofloxacin formula-

(56) References Cited

OTHER PUBLICATIONS tions for inhalation in healthy volunteers and in non-cystic bronchiectasis patients," Am. J. Respir. Crit. Care Med. (2010) 181:A3192.
Bucke, W. E. et al., "Surface-modified amikacin-liposomes: organ distribution and interaction with plasma proteins," Journal of Drug Targeting, 5(2):99-108 (1997).
Bunderberg de Jong, H. G. et al., Koazevation (Entmischung in Kolloidalen Systemen), Koll, Zeitsch, 50(10):39-48 (1930).
Cabanes et al., "Sustained release of liposome-encapsulated enrofloxacin after intramuscular administration in rabbits," American Journal of Veterinary Research, 56(11):1498-501 (1995).
Cantin, A. M. et al., "Aerosolized prolastin suppresses bacterial proliferation in a model of chronic pseudomonas aeruginosa lung infection," Am. J. Respir. Crit. Care Med., 160:1130-1135 (1999).
Carlier, M. B. et al., "Inhibition of lysosomal phospholipases by aminoglycoside antibiotics: in vitro comparative studies," Antimicrobial Agents and Chemotherapy, 23(3):440-449 (1983).
Carter, G., "Characterization of biofilm formation by *Mycobacterium avium* strains," J. Med. Microbial. (2003) 52:747-52.
Cash, H. A. et al., "A rat model of chronic respiratory infection with Pseudomonas aeruginosa," American Review of Respiratory Disease, 119(3):453-459 (1979).
Challoner, P. B. et al., "Gamma Scintigraphy Lung Deposition Comparison of TOBI in the PARI LC PLUS Nebulizer and the Aerodose Inhaler," American Thoracic Society 97th International Conference, San Francisco, California, Aerogen, Inc. (2001), 1 page.
Chambless, J. D. et al., "A three-dimensional computer model of four hypothetical mechanisms protecting biofilms from antimicrobials," Appl. Environ. Microbiol., 72(3):2005-2013 (2006).
Chan, C. H. S. et al., "Mycobacteria as a cause of infective exacerbation in bronchiectasis," Postgrad. Med. J., 68:896-899 (1992).
Chapman, D., "Physicochemical Properties of Phospholipids and Lipid-Water Systems," In: Liposome Technology, Chapter 1, vol. I, Preparation of Liposomes, Gregoriadis G. (ed.), CRC Press, Inc., Boca Raton, Florida, pp. 1-18 (1984).
Chmiel, J. F. et al., "State of the art: why do the lungs of patients with cystic fibrosis become infected and why can't they dear the infection?", Respiratory Research, 4:8-20 (2003).
Chono, S, et al., "Influence of particle size on drug delivery to rat alveolar macrophages following pulmonary administration of ciprofloxacin incorporated into liposomes," Journal of Drug Targeting, 14(8):557-566 (2006).
Chuchalin et al., "A formulation of aerosolized tobramycin (Bramitob) in the treatment of patients with cystic fibrosis and Pseudomonas aeruginosa infection: a double-blind, placebo-controlled, multicenter study," Paediatric Drugs, 9(Suppl. 1), pp. 21-31, 2007.
Ciofu, O. et al., "Occurrence of Hypermutable Pseudomonas aeruginosa in Cystic Fibrosis Patients Is Associated with the Oxidative Stress Caused by Chronic Lung Inflammation," Antimicrobial Agents and Chemotherapy, 49(6):2276-2282 (Jun. 2005).
Cipro® Products FDA Approval Letter (Mar. 2004), 4 pages.
Cipro® I.V. Label (Jan. 2005), 26 pages.
Cipolla, D., "Development and Characterization of an In Vitro Release Assay for Liposomal Ciproftoxacin for Inhalation," J. Pharm. Sci., 103(1):314-327 (2014).
Cipolla, D., "Liposomal Formulations for Inhalation," Ther. Deliv., 4(8): 1047-1072 (2013).
Cipolla, D., et al., "Development of Liposomal Ciprofloxacin to Treat Lung Infections," Pharmaceutics 2016, vol. 8, No. 1, doi:10.3390/pharmaceutics 8010006, 31 pages.
Cipolla et al., "Assessment of aerosol delivery systems for recombinant human deoxyribonuclease," S.T.P. Pharma Sciences, 4(1), pp. 50-62 (1994).
Clancy, J. P. et al., "Phase II studies of nebulised Arikace in CF patients with Pseudomonas aeruginosa infection," Thorax, 68(9):818-825 (2013).
Clay. M. M. et al., "Assessment of jet nebulisers for lung aerosol therapy," Lancet, 2:592-594 (1983).
ClinicalTrials.gov, "Safety and Efficacy Study of Ciprofloxacin for Inhalation in Patients With Non-Cystic Fibrosis Bronchiectasis 'ORBIT-1'", Identifier: NCT00889967, First Received: Apr. 27, 2009, 3 pages.
Colardyn, F., "The efficacy and safety of isepamicin and ceftazidime compared with amikacin and ceftazidime in acute lower respiratory tract infection," Journal of Chemotherapy, 7(2):129-135 (1995).
Coleman, L. T. et al., "Bronchiectasis in children," Journal of Thoracic Imaging, 10(4)268-279 (1995).
Comis, R. L., "Carboplatin in the treatment of non-small cell lung cancer: a review," Oncology, 50(2):37-41 (1993).
Conley et al., "Aerosol Delivery of Liposome-Encapsulated Ciprofloxacin: Aerosol Characterization and Efficacy against Francisella tularensis Infection in Mice," Antimicrobial Agents and Chemotherapy, 41(6):1288-1292 (Jun. 1997).
Cooksey, R. C. et al., "Antimicrobial susceptibility patterns of Streptococcus pneumoniae," Antimicrobial Agents and Chemotherapy, 13(4):645-648 (1978).
Costerton, J. W. et al., "Bacterial biofilms: A common cause of persistent infections," Science, 284:1318-1322 (1999).
Couvreur, P. et al., "Liposomes and nanoparticles in the treatment of intracellular bacterial infections," Pharmaceutical Research, 8(9):1079-1085 (1991).
Cremades, M. J. et al., "Repeated pulmonary infection by Nocardia asteroides complex in a patient with bronchiectasis," Respiration, 65:211-213 (1998).
Crowther, N. R. et al., "Inhaled aminoglycoside (gentamicin) in bronchiectasis: Dry powder vs. nebulization vs. intravenous therapy," Clinical and Investigative Medicine, Annual Meeting of the Canadian Society for Clinical Investigation, The Royal College of Physicians and Surgeons of Canada and Participating Societies, Toronto, Canada, Abstract 530 (Sep. 24-27, 1998), 3 pages.
Cullis et al., "Liposomes as Pharmaceuticals," Liposomes From Biophysics to Therapeutics, pp. 39-72 (M. Ostro ed., 1987).
Cullis et al., "Generating and loading of liposomal systems for drug delivery applications," Advanced Drug Delivery Reviews, 3, pp. 267-282 (1989).
Currie, D. C., "Nebulisers for bronchiectasis," Thorax, 52(Suppl. 2):S72-S74 (1997).
British Thoracic Society Nebuliser Project Group, Thorax, 1997, vol. 52 (Suppl. 2), S1-S24.
Cymbala, A. A. et al., "The Disease-Modifying Effects of Twice-Weekly Oral Azithromycin in Patients with Bronchiectasis," Treat Respir. Med. 2005;4(2):117-122.
Cynamon, M. H. et al., "Liposome-Encapsulated-Amikacin Therapy of *Mycobacterium avium* Complex Infection in Geige Mice," Antimicrobial Agents and Chemotherapy, 33(8):1179-1183 (1989).
Dally, M. B. et al., "Ventilatory effects of aerosol gentamicin," Thorax, 33:54-56 (1978).
Damaso, D. et al., "Susceptibility of current clinical isolates of Pseudomonas aeruginosa and enteric gram-negative bacilli to amikacin and other aminoglycoside antibiotics," The Journal of Infectious Diseases, 134:S394-S390 (1976).
Deamer, D. W. et al., "Liposome Preparation: Methods and Mechanisms," Chapter 1 in: Liposomes, Ostro, M. J. (ed.), Marcel Dekker, Inc., New York (1983), 27 pages.
Dees, C. et al., "The mechanism of enhanced intraphagocytic killing of bacteria by liposomes containing antibiotics," Veterinary Immunology and Immunopathology, 24:135-146 (1990).
Del Porto, P. et al., "Dysfunctional CFTR alters the bactericidal activity of human macrophages against Pseudomonas aeruginosa," PLoS ONE, 6(5):e19970 (2011).
Demaeyer, P. et al., "Disposition of liposomal gentamicin following intrabronchial administration in rabbits," Journal Microencapsulation, 10(1):77-88 (1993).
Deol, P. et al., "Lung specific stealth liposomes: stability, biodistribution and toxicity of liposomal antitubular drugs in mice," Biochimica et Biophysica Acta, 1334:161-172 (1997).
Dequin, P. F. et al., "Urinary excretion reflects lung deposition of aminoglycoside aerosols in cystic fibrosis," Eur. Respir. J., 18(2):316-322 (2001).
Desai et al., "A facile method of delivery of liposomes by nebulization," Journal of Controlled Release, 84(1-2):69-78 (2002).

(56) References Cited

OTHER PUBLICATIONS

Desai et al., "A Novel Approach to the Pulmonary Delivery of Liposomes in Dry Powder Form to Eliminate the Deleterious Effects of Milling," Journal of Pharmaceutical Sciences, 91(2):482-491 (Feb. 2002).

Desai, T. R. et al., "Determination of surface free energy of interactive dry powder liposome formulations using capillary penetration technique," Colloids and Surfaces B: Biointerfaces, 22:107-113 (2001).

Desai, "Delivery of liposomes in dry powder form: aerodynamic dispersion properties," European Journal of Pharmaceutical Sciences 20:459-467 (2003).

Di Ninno et al. (1993). Liposome-encapsulated ciprofloxacin is effective in the protection and treatment of BALB/c mice against Francisella tularensis. The Journal of Infectious Diseases 168, pp. 793-794.

Dickie, K. J. et al., "Ventilatory effects of aerosolized kanamycin and polymyxin," Chest, 63(5):694-697 (1973).
Dong, C. et al., "Acacia-gelatin microencapsulated liposomes: preparation, stability and release of acetylsalicylic acid," Pharmaceutical Research, 10(1):141-146 (1993).
Doring, G. et al., "Antibiotic therapy against Pseudomonas aeruginosa in cystic fibrosis: a European consensus," Eur Respir J., 16(4):749-767 (2000).
Drenkard, E. et al., "Pseudomonas biofilm formation and antibiotic resistance are linked to phenotypic variation," Nature, 416:740-743 (2002).
Driscoll et al., "Intratracheal Instillation as an Exposure Technique for the Evaluation of Respiratory Tract Toxicity: Uses and Limitations," Toxicological Sciences, 55, pp. 24-35 (2000).
Dupont et al., "A randomized placebo-controlled study of nebulized liposomal amikacin (Arikace) in the treatment of cystic fibrosis patients with chronic Pseudomonas aeruginosa lung infection," Journal of Cystic Fibrosis, 1(7):S26, Abstract 102, Jan. 2008.
Duzgunes, N. et al., "Treatment of intracellular *Mycobacterium avium* complex infection by free and liposome-encapsulated sparfloxacin," Antimicrobial Agents and Chemotherapy, 40(11):2618-2621 (Nov. 1996).
Eboka (2005). Aqueous solubility of ciprofloxacin in the presence of metal cations. Tropical Journal of Pharmaceutical Research, 4(1), pp. 349-354.
Ehlers, S. et al., "Liposomal amikacin for treatment of *M. avium* Infections in clinically relevant experimental settings," Zbl. Bakt, 284:218-231 (1996).
Eigen (1995). A multicenter study of alternate-day prednisone therapy in patients with cystic fibrosis. The Journal of Pediatrics, 126(4), pp. 515-523.
El-Din, M. A. T. et al., "Nebulizer therapy with antibiotics in chronic suppurative lung disease," Journal of Aerosol Medicine, 7(4):345-350 (1994).
Elhissi et al., "Formulations generated from ethanol-based proliposomes for delivery via medical nebulizers," Journal of Pharmacy and Pharmacology, 58:887-894 (Jul. 2006).
Eller, J. M. et al., "The therapy of bronchiectasis," Deutsche Medizinische Wochenschrift, 118(44):1608-1610 (1993).
Farber, J. E. et al., "The use of aerosol penicillin and streptomycin in bronchopulmonary infections," California Medicine, 73(3):214-217 (1950).
Fenske et al., "Encapsulation of weakly-basic drugs, antisense oligonucleotides, and plasmid DNA within large unilamellar vesicles for drug delivery applications," Liposomes Second Edition A Practical Approach, pp. 167-191 (V. Torchilin et al. eds., 2003).
Fielding, R. M. et al., "Pharmacokinetics and Urinary Excretion of Amikacin in Low-Clearance Unilamellar Liposomes after a Single or Repeated Intravenous Administration in the Rhesus Monkey," Antimicrobial Agents and Chemotherapy, 43(3):503-509 (1999).
Finke, W., "Long-term antibiotic therapy in chronic bronchitis and infectious asthma. Control and prevention of bronchopulmonary disease." Antibiotics and Chemotherapy, 4(3):319-329 (1954).
Finlay, W. H. et al., "Regional lung deposition of nebulized liposome-encapsulated ciprofloxacin," International Journal of Pharmaceutics (Amsterdam), 167(1-2):121-127 (Jun. 1, 1998).
Fountain, M. W. et al., "Treatment of *Brucella canis* and *Brucella abortus* In vitro and in vivo by stable plurilamellar vesicle-encapsulated aminoolycosides," The Journal of Infectious Diseases, 152(3):529-535 (1985).
Furneri et al., "Ofloxacin-Loaded Liposomes: In Vitro Activity and Drug Accumulation in Bacteria," Antimicrobial Agents Chemotherapy, 44(9):2458-2464 (2000).
Garcia, A. T., "Efficacy of amikacin sulfate in lower respiratory infections," Investigacion Medica Internacional, 9(3):235-240 (1982) (with English Abstract).
Gay et al., "In Vitro Activities of Norfloxacin and Ciprofloxacin Against *Mycobacterium tuberculosis*, *M. avium* Complex, M. chelonei, M. fortuitum, and M. kansaii," Antimicrobial Agents and Chemotherapy, vol. 26, No. 1, pp. 94-96 (Jul. 1984).
Geller, D. E. et al., "Pharmacokinetics and bioavailability of aerosolized tobramycin in cystic fibrosis," Chest, 122(1):219-226 (2002).
Gibson, R. L. et al., "Pathophysiology and management of pulmonary infections in cystic fibrosis," American Journal of Respiratory and Critical Care Medicine, 168(8):918-951 (2003).
Gibson, R. L. et al., "Significant microbiological effect of inhaled tobramycin in young children with cystic fibrosis," American Journal of Respiratory and Critical Care Medicine, 167(6):841-849 (2003).
Gilbert, B. E. et al., "Tolerance of volunteers to cyclosporine A-dilauroylphosphatidylcholine liposome aerosol," American Journal of Respiratory and Critical Care Medicine, 156(6):1789-1793 (1997).
Gleiser, C. A. et al., "Pathology of experimental respiratory anthrax in Macaca mulatta," Brit. J. Exp. Path., 44:416-426 (1963).
Goldman, J. M. et al., "Inhaled micronised gentamicin powder: a new delivery system," Thorax, 45:939-940 (1990).
Gonzales-Rothi, R. J. et al., "Liposomes and pulmonary alveolar macrophages: functional and morphologic interactions," Experimental Lung Research, 17:687-705 (1991).
Goss, C. H. et al., "Update on cystic fibrosis epidemiology," Current Opinion in Pulmonary Medicine, 10(6):510-514 (2004).
Graczyk, J. et al., "*Staphylococcal pneumonia*—analysis of material of patients treated in lung diseases hospital in years 1981-1994," Pneumonologia | Alergologia Polska, 65(11-12):767-774 (1997) (with English Abstract).
Greene, K. E. et al., "Radiographic changes in acute exacerbations of cystic fibrosis in adults: A pilot study," AJR, 163:557-562 (1994).
Gubernator, J., "Active methods of drug loading into liposomes: recent strategies for stable drug entrapment and increased in vivo activity," Expert Opinion in Drug Delivery, vol. 8(5), 2011, pp. 565-580.
Gunther, A. et al., "Surfactant alteration and replacement in acute respiratory distress syndrome," Respiratory Research, 2(6): 353-364 (2001).
Gursoy et al. (1997). Characterization of ciprofloxacin liposomes; derivative ultraviolet spectrophotometric determinations. J. Microencapsulation 14(6), pp. 769-776.
Hagwood, S. et al., "Structure and properties of surfactant protein B," Biochimica et Biophysica Acta., 1408:150-160 (1998).
Hansen, C. R. et al., "Long-term azithromycin treatment of cystic fibrosis patients with chronic pseudomonas aeruginosa infection: an observational cohort study," Journal of Cystic Fibrosis, 4(1):35-40 (2005).
Helbich, T. et al., "High-resolution computed tomography of the lung in young patients with cystic fibrosis," Radiologe, 33(3):142-146 (1993) (English Abstract).
Hess, D. et al., "Medication nebulizer performance. Effects of diluent volume nebulizer flow, and nebulizer brand," Chest, 110:498-505 (1996).
Hess, D. R., "Nebulizers: Principles and Performance," Respiratory Care, 45(6):609-622 (2000).
Hewitt, W. L. et al., "Antibiotic therapy of abscess of the lung and bronchiectasis," California Medicine, 76(5):319-324 (1952).
Hoffman, L. R. et al., "Aminoglycoside antibiotics induce bacterial biofilm formation," Nature, 436:1171-1175 (2005).

(56) References Cited

OTHER PUBLICATIONS

Honeybourne, D., "Antibiotic penetration in the respiratory tract and implications for the selection of antimicrobial therapy," Current Opinion in Pulmonary Medicine 1997, 3(2):170-174.
Howell, S. B., "Clinical applications of a novel sustained-release injectable drug delivery system: DepoFoam Technology," Cancer Journal, 7(3):219-227 (2001).
Hrkach, J. S. et al., "Synthesis of poly(L-lactic acid-co-L-lysine) graft copolymers," Macromolecules, 28:4736-4739 (1995).
Hrkach, J. S. et al., "Poly(L-Lactic acid-co-amino acid) graft copolymers: A class of functional biodegradable biomaterials," In: Hydrogels and Biodegradable Polymers for Bioapplications, Chapter 8, ACS Symposium Series No. 627, Ottenbrite, R. M. et al. (eds.), American Chemical Society, pp. 93-102 (1996).
Huang, L. et al., "Progress of liposome's applications in biomedicine," International Journal of Biologicals, 29(3):130-132 and 137 (2006).
Huang et al. (2006). Pulmonary delivery of insulin by liposomal carriers. Journal of Controlled Release 113, pp. 9-14.
Hubble, D., "Discussion on respiratory catarrh in children," Proceedings of the Royal Society of Medicine, 52(9):701-710 (1959).
Hung, O. R. et al., "Pharmacokinetics of inhaled liposome-encapsulated fentanyl," Anesthesiology, 83(2): 277-284 (Aug. 1995).
Hung, J. C. et al., "Evaluation of two commercial jet nebulisers and three compressors for the nebulisation of antibiotics," Archives of Disease in Childhood, 71(4):335-338 (Oct. 1994).
Hyde et al., "Anatomy, pathology, and physiology of the treacheobronchial tree: Emphasis on the distal airways," J. Allergy Clin. Immunol., vol. 124, No. 6, pp. S72-S77 (2009).
Hunt, B. E. et al., "Macromolecular mechanisms of sputum inhibition of tobramycin activity," Antimicrobial Agents and Chemotherapy, 39(1):34-39 (1995).
Ikegami, M. et al., "Surfactant protein metabolism in vivo," Biochimica et Biophysica Acta, 1408:218-225 (1998).
Ikemoto, H. et al., "Susceptibility of bacteria isolated from the patients with lower respiratory tract infections to antibiotics," The Japanese Journal of Antibiotics, 42(11):2350-2353 (1989).
Ip, M. S. M. et al., "Bronchiectasis and related disorders," Respirology, 1:107-114 (1996).
Ishii, F. et al., "Procedure for Preparation of Lipid Vesicles (Liposomes) Using the Coacervation (Phase Separation) Technique," Langmuir, 11(2):483-486 (1995).
Janoff, A. S. et al., "Unusual lipid structures selectively reduce the toxicity of amphotericin B," Proc. Nat. Acad. Sci. USA, 85:6122-6126 (1988).
Jayaraman, S. et al., "Noninvasive in vivo fluorescence measurement of airway-surface liquid depth, salt concentration, and pH," J. Clin. Invest. 107:317-324 (2001).
Johansson, J., "Structure and properties of surfactant protein C," Biochimica et Biophysica Acta, 1408:161-172 (1998).
Johnston, M. J. W. et al., "Therapeutically optimized rates of drug release can be achieved by varying the drug-to-lipid ratio in liposomal vincristine formulations," Biochimica et Biophysica Acta, 1758:55-64 (2006).
Katare, O. P. et al., "Enhanced in vivo Performance of LiposomalIndomethacin Derived From Effervescent Granule Based Proliposomes," J. Microencapsulation, 12(5):487-493 (1995).
Kensil et al., "Alkaline Hydrolysis of Phospholipids in Model Membranes and the Dependence on Their State of Aggregation," Biochemistry, 20:6079-6085 (1981).
Kesavalu, L. et al., "Differential effects of free and liposome encapsulated amikacin on the survival of *Mycobacterium avium* complex in mouse peritoneal macrophages," Tubercle, 71(3):215-217 (1990).
Kim, E. K. et al., "Pharmacokinetics of intravitreally injected liposomes encapsulated tobramycin in normal rabbits," Yonsei Medical Journal, 31(4):308-314 (1990).
Klemens, S. P. et al., "Liposome-encapsulated-gentamicin therapy of *Mycobacterium avium* complex infection in beige mice," Antimicrobial Agents and Chemotherapy, 34(6):967-970 (1990).

Knoch, M. et al., "The customised electronic nebuliser: a new category of liquid aerosol drug delivery systems," Expert Opin. Drug Deliv., 2(2):377-390 (2005).
Knox, K. et al., "Chronic bronchitis. An attempt to control chronic infection with Haemophilus influenzae by aerosol therapy," The Lancet, pp. 120-122 (1955).
Kyriacos et al., "In Vitro Testing of Ciprofloxacin Formulations and Preliminary Study on BCS Biowaiver," Journal of Food and Drug Analysis, (2009) 17(2): 78-84.
Labiris, N. R. et al., "Pulmonary drug delivery. Part II: The role of inhalant delivery devices and drug formulations in Therapeutic effectiveness of aerosolized medications," Br.J.Clin.Pharmacol., 56(6):600-612 (2003).
Lagace, J. et al., "Liposome-encapsulated antibiotics: preparation, drug release and antimicrobial activity against Pseudomona aeruginosa," Journal Microencapsulation, 8(1) 53-61 (1991).
Landyshev, Y. S. et al., "Clinical and experimental aspects of liposomal hydrocortisone treatment of bronchial asthma," Ter. Arkh., 74(8):45-48 (2002) (with English Abstract).
Lasic et al., "Transmembrane gradient driven phase transitions within vesicles: lessons for drug delivery," Biochemica et Biophysica Acta, 1239:145-156 (1995).
Lasic, D. D., "Gelation of liposome interior: A novel method for drug encapsulation," FEBS Letters, 312(2.3):255-258 (Nov. 1992).
Lass, J. S. et al., "New advances in aerosolised drug delivery: vibrating membrane nebuliser technology," Expert Opin Drug Deliv., 3(5):693-702 (2006).
Le Brun, P. P. H. et al., "A review of the technical aspects of drug nebulization," Pharmacy World & Science, 22(3):75-81 (2000).
Le Brun, P. P. H. et al., "Inhalation of tobramycin in cystic fibrosis part 1: The choice of a nebulizer," International Journal of Pharmaceutics, 189:205-214 (1999).
Le Brun, P. P. H. et al., "Inhalation of tobramycin in cystic fibrosis part 2: Optimization of the tobramycin solution for a jet and ultrasonic nebulizer," International Journal of Pharmaceutics, 189:215-225 (1999).
Le Brun, P. P. H et al., "Dry powder inhalation of antibiotics in cystic fibrosis therapy: part 2. Inhalation of a novel colistin dry powder formulation: a feasibility study in healthy volunteers and patients," European Journal of Pharmaceutics and Biopharmaceutics, 54:25-32 (2002).
Li, Z. et al., "Nebulization of liposomal amikacin formulations: SLIT Amikacin," Respiratory Drug Delivery, 3:801-804 (2006).
Li, Z. et al., "Characterization of nebulized liposomal amikacin (Arikace) as a function of droplet size," Journal of Aerosol Medicine and Pulmonary Drug Delivery, 21(3):245-253 (2008).
Lin, H.-C. et al., "Inhaled gentamicin reduces airway neutrophil activity and mucus secretion in bronchiectasis," Am. J. Respir. Crit. Care Med., 155:2024-2029 (1997).
Lipuma, J. J., "Microbiological and immunologic considerations with aerosolized drug delivery," Chest. Sep. 2001;120(3 Suppl):118S-123S.
Lowry et al., "Effects of pH and osmolarity on aerosol-induced cough in normal volunteers," Clinical Science, 74:373-376 (1988).
Lutwyche, P. et al., "Intracellular delivery and antibacterial activity of gentamicin encapsulated in pH-sensitive liposomes," Antimicrobial Agents and Chemotherapy, 42(10):2511-2520 (1998).
Magallanes, M. et al., "Liposome-incorporated ciprofloxacin in treatment of murine salmonellosis," Antimicrobial Agents and Chemotherapy, Nov. 1993, 37(11):2293-2297.
Majumdar, S. et al., "Efficacies of Liposome-Encapsulated Streptomycin and Ciprofloxacin against *Mycobacterium avium*-M. intracellulare Complex Infections in Human Peripheral Blood Monocyte/Macrophages," Antimicrobial Agents and Chemotherapy, 36(12):2808-2815 (Dec. 1992).
Marcotte, G. V. et al., "Chronic productive cough and bronchiectasis in a 40-year-old woman," Annals of Allergy, Asthma & Immunology, 78(6):559-564 (1997).
Marier, J. F. et al., "Liposomal tobramycin against pulmonary infections of Pseudomonas aeruginosa: a pharmacokinetic and efficacy study following single and multiple intratracheal administrations in rats," Journal Antimicrobial Chemotherapy, 52:247-252 (2003).

(56) References Cited

OTHER PUBLICATIONS

Marier, J-F. et al., "Pharmacokinetics and efficacies of liposomal and conventional formulations of tobramycin after intratracheal administration in rats with pulmonary burkholderia cepacia infection," Antimicrobial Agents and Chemotherapy, 46(12):3776-3781 (2002).
Mariotti, A. B. et al., "Aerosol therapy with tobramycin in exacerbations of chronic obstructive lung disease (7 cases)," 66(2):198-202 (1996) (with English Abstract).
Martini, W. Z. et al., "Lung surfactant kinetics in conscious pigs," Am J Physiol., 277(1 Pt 1): E187-E195 (1999).
Marwah, O. S. et al., "Bronchiectasis. How to identify, treat and prevent," Postgrad. Med., 97(2):149-150, 153-156, 159 (1995) (Abstract).
Maurer, N. et al., "Anomalous solubility behavior of the antibiotic ciprofloxacin encapsulated in liposomes: a 1H-NMR study," Biochimica et Biophysica Acta, 1374:9-20 (1998).
McAllister, S. M. et al., "Antimicrobial properties of liposomal polymyxin B," Journal of Antimicrobial Chemotherapy, 43:203-210 (1999).
Meers, P. et al., "Biofilm penetration, triggered release and in vivo activity of inhaled liposomal amikacin in chronic Pseudomonas aeruginosa lung infections," Journal of Antimicrobial Chemotherapy, 61(4):859-868 (2008).
Mendelman, P. M. et al., "Aminoglycoside penetration, inactivation, and efficacy in cystic fibrosis sputum," American Review of Respiratory Disease, 132(4):761-765 (1985).
Mercer, R. R. et al., "Cell Number and Distribution in Human and Rat Airways," Am. J. Respir. Cell Mol. Biol., vol. 10, pp. 613-624, 1994.
Mohanty, B. et al., "Systematic of alcohol-induced simple coacervation in aqueous gelatin solutions," Biomacromolecules, 4:1080-1086 (2003).
Mombelli, G. et al., "Anti-pseudomonas activity in bronchial secretions of patients receiving amikacin or tobramycin as a continuous infusion," Antimicrobial Agents and Chemotherapy, 19(1):72-75 (1981).
Montero et al. (1998). Fluoroquinolone-biomembrane interactions: monolayer and calorimetric studies. Langmuir 14(9), pp. 2451-2454.
Morgan, J. R. et al., "Preparation and properties of liposome-associated gentamicin," Antimicrobial Agents and Chemotherapy, 17(4):544-548 (1980).
Moss, R. B., "Administration of aerosolized antibiotics in cystic fibrosis patients," Chest, 120(3 Suppl):107S-113S (Sep. 2001).
Myers, M. A. et al., "Pulmonary effects of chronic exposure to liposome aerosols in mice," Experimental Lung Research, 19:1-19 (1993).
Nakazawa, S. et al., "Studies on a new aminoglycoside antibiotic, amikacin (BB-K8) in pediatrics," The Japanese Journal of Antibiotics, 27(4):438-445 (1974).
Nasu, M. et al., "Appropriate use of antimicrobial agents," Selection of Anti-infective, Clinic in Japan (Special Number) Infection Disease Study in New Era (first volume), 2003, 61st issue, pp. 718-723.
National Jewish Health, "Third sputum smear test negative for XDR TB patient Andrew Speaker," [Online], Retrieved from the Internet: <URL: https://www.nationaljewish.org/about/news/press-releases/2007/smear-test-3>, Jun. 5, 2007, 2 pages.
Fresenius KABI USA, New Drug Application (NDA): 019887, NebuPent®on Drugs@FDA [online], <https://www.accessdata.fda.gov/scripts/cder/daf/index.cfm?event=BasicSearch.process>, Retrieved on Apr. 24, 2017, 3 pages.
Newton, D. W. et al., Chapter 4: "Coacervation: Principles and Applications," In: Polymers for Controlled Drug Delivery, Tarcha, P. J. (ed.), CRC Press, Boca Raton, pp. 67-81 (1991).
Nightingale, S. D. et al., "Liposome-encapsulated gentamicin treatment of *Mycobacterium avium-Mycobacterium intracellulare* complex bacteremia in AIDS patients," Antimicrobial Agents and Chemotherapy, 37(9):1869-1872 (1993).

Nikolaizik et al., "A pilot study to compare tobramycin 80 mg injectable preparation with 300 mg solution for inhalation in cystic fibrosis patients," Canadian Respiratory Journal, 15(5):259-262, Jul./Aug. 2008.
Niven, R. W. et al., "Nebulization of liposomes. I. Effects of lipid composition," Pharmaceutical Research, 7(11):1127-1133 (Nov. 1990).
Niven, R. W. et al., "Nebulization of liposomes. II. The effects of size and modeling of solute release profiles," Pharmaceutical Research, 8(2):217-221 (1991).
Niven, R. W. et al., "Nebulization of liposomes. III. The effects of operating conditions and local environment," Pharmaceutical Research, 9(4):515-520 (1992).
U.S. Department of Health and Human Services, "Nonclinical Safety Evaluation of Reformulated Drug Products and Products Intended for Administration by an Alternate Route, Guidance for Industry and Review Staff, Good Review Practice," Oct. 2015, 12 pages.
Oh, Y-K et al., "Formulation and Efficacy of Liposome-Encapsulated Antibiotics for Therapy of Intracellular Mycobacterium avium Infection," Antimicrobial Agents and Chemotherapy, 39(9):2104-2111 (Sep. 1995).
Oizumi, K. et al., "Therapeutic effect of amikacin for infections with gram-negative bacilli, especially for stubborn respiratory infections," The Japanese Journal of Antibiotics, 31(1):15-23 (1978).
Olsen, A. M., "Streptomycin aerosol in the treatment of chronic bronchiectasis: preliminary report," Staff Meetings of the Mayo Clinic, pp. 53-54 (1946).
Olsen, A. M., "Nebulization therapy in bronchiectasis: The use of penicillin and streptomycin aerosols," In: Collected Papers of The Mayo Clinic and The Mayo Foundation, Hewitt, R. M. et al. (eds.), 38:579-586 (1946).
Olsen, A. M., "Nebulization therapy in bronchiectasis: The use of penicillin and streptomycin aerosols," J.A.M.A., 134(11):947-953(1947).
Omri, A. et al., "Incorporation, release and in-vitro antibacterial activity of liposomal aminoglycosides against Pseudomonas aeruginosa," Journal Antimicrobial Chemotherapy, 36(4):631-639 (1995).
Omri, A. et al., "Comparison of the bactericidal action of amikacin, netilmicin and tobramtcin in free and liposomal formulation against pseudomonas aeruginosa," Chemotherapy, 42:170-176 (1996).
Omri, A. et al., "Pulmonary retention of free and liposome-encapsulated tobramycin after intratracheal administration in uninfected rats and rats infected with Pseudomonas aeruginosa," Antimicrobial Agents and Chemotherapy, 38(5):1090-1095 (1994).
Pai, V. B. et al., "Efficacy and safety of aerosolized tobramycin in cystic fibrosis," Pediatric Pulmonology, 32(4):314-327 (2001).
Papahadjopoulos, D. et al., "Phospholipid model membranes. I. Structural characteristics of hydrated liquid crystals," Biochimica et Biophysica Acta., 135:624-638 (1967).
Paradisi, F. et al., "Acute and chronic bronchopulmonary infections and aminoglycoside antibiotics," Chemioterapia Antimicrobica, 1(2):224-227 (1978).
Parsek, M. R. et al., "Acyl-homoserine lactone quorum sensing gram-negative bacteria: a signaling mechanism involved in associations with higher organisms," Proc. Nat. Acad. Sci., 97(16):6789-6793 (2000).
Patton, J. S. et al., "The lungs as a portal of entry for systemic drug delivery," Proc. Am. Thor. Soc., 1:338-344 (2004).
Perkins, W. R. et al., "Aerosolization of liposomal amikacin (Arikace) using different nebulizers: Selection of the eflow nebulizer," Poster and Oral Presentation at North American Cystic Fibrosis Conference (Oct. 2007), Pediatric Pulmonology, 42(30):356-357, abs. 434, 14 pages.
Perkins, W. R. et al., "Role of lipid polymorphism in pulmonary surfactant," Science, 273:330-332 (Jul. 1996).
Petersen, E. A. et al., "Liposomal amikacin: improved treatment of *Mycibacterium avium* complex infection in the beige mouse model," Journal Antimicrobial Chemotherapy, 38:819-828 (1996).
Petkowicz, J. et al., "Hypoglycemic Effect of Liposome-Entrapped Insulin Administered by Various Routes into Normal Rats," Pol. J. Pharmacol. Pharm., 41:299-304 (1989).

(56) References Cited

OTHER PUBLICATIONS

Piersimoni et al., "Pulmonary infections associated with non-tuberculous mycobacteria in immunocompetent patients," Lancet Infect Dis, 8: 323-334 (2008).
Pilewski, J. M. et al., "Role of CFTR in airway disease," Physiological Reviews, 79(1):S215-S255 (1999).
Pines, A. et al., "Treatment of severe pseudomonas infections of the bronchi," British Medical Journal, 1:663-665 (1970).
Pines, A. et al., "Gentamicin and colistin in chronic purulent bronchial infections," British Medical Journal, 2:543-545 (1967).
Potter, B. P., "Aerosol antibiotic therapy in suppurative diseases of the lung and bronchi," Diseases of the Chest, 15(4):436-448 (Apr. 1949).
Poyner, E. A. et al., "A comparative study on the pulmonary delivery of tobramycin encapsulated into liposomes and PLA microspheres following intravenous and endotracheal delivery," Journal of Controlled Release, 35(1):41-48 (1995).
Poyner, E. A. et al., "Preparation, properties and the effects of free and liposomal tobramycin on siderophore production by Pseudomonas aeruginosa," Journal of Antimicrobial Chemotherapy, 34:43-52 (1993).
Novartis Pharmaceuticals Corporation, TOBI, Tobramycin Inhalation Solution, USP, Nebulizer Solution, Prescribing Information, Oct. 2015, 14 pages.
Gilead Sciences, Inc., CAYSTON (aztreonam for inhalation solution) Highlights of Prescribing Information (2014), 19 pages.
Press Release, "Transave Announces Positive Phase II Results for Once-Daily Arikace in the Treatment of Cystic Fibrosis Patients Who Have Pseudomonas Lung Infections," Presented at the European Cystic Fibrosis Society Conference, Monmouth Junction, NJ, Jun. 13, 2008, 3 pages.
Price, C. I et al., "Liposome delivery of aminoglycosides in burn wounds," Surgery, Gynecology & Obstetrics, 174(5):414-418 (May 1992).
Price, C. I et al., "Liposome encapsulation: a method for enhancing the effectiveness of local antibiotics," Surgery, 115(4)480-487 (1994).
Price, C. I. et al., "Enhanced effectiveness of intraperitoneal antibiotics administered via liposomal carrier," Arch Surgery, 124:1411-1415 (1989).
Price, K. E. et al., "Amikacin, an aminoglycoside with marked activity against antibiotic-resistant clinical isolates," The Journal of Infectious Diseases, 134:S249-S261 (1976).
Ramsammy, L. S. et al., "The effect of gentamicin on the biophysical properties of phosphatidic acid liposomes is influenced by the O–C=O group of the lipid," Biochemistry, 27:8249-8254 (1988).
Ramsey, B. W. et al., "Intermittent administration of inhaled tobramycin in patients with cystic fibrosis. Cystic Fibrosis Inhaled Tobramycin Study Group," The New England Journal of Medicine, 340(1):23-30 (1999).
Ramsey, B. W. et al., "Efficacy of aerosolized tobramycin in patients with cystic fibrosis," The New England Journal of Medicine, 328:1740-1746 (1993).
Rastogi et al. (2006). Particulate and vesicular drug carriers in the management of tuberculosis. Current Drug Delivery 3(1), pp. 121-128.
Rau, J. L. et al., "Performance Comparison of Nebulizer Designs: Constant-Output, Breath-Enhanced, and Dosimetric," Respir. Care 2004;49(2):174-179.
Roehrborn, A. A. et al., "Lipid-based slow-release formulation of amikacin sulfate reduces foreign body-associated infections in mice," Antimicrobial Agents and Chemotherapy, 39(8):1752-1755 (1995).
Ross et al., "Aqueous solubilities of some variously substituted quinolone antimicrobials," International Journal of Pharmaceutics, 63(3): 237-250 (1990).
Sabra, W. et al., "Physiological responses of pseudomonas aeruginosa PAO1 to oxidative stress in controlled microaerobic and aerobic cultures," Microbiology, 148:3195-3202 (2002).
Saiman et al., "Antibiotic Susceptibility of Multiply Resistant Pseudomonas aeruginosa Isolated from Patients with Cystic Fibrosis, Including Candidates for Transplantation," Clinical Infectious Diseases, 23:532-537 (Sep. 1996).
Sangwan et al., "Aerosolized Protein Delivery in Asthma: Gamma Camera Analysis of Regional Deposition and Perfusion," Journal of Aerosol Medicine, vol. 14, No. 2, pp. 185-195 (2001).
Schaad, U. B. et al., "Efficacy of inhaled amikacin as adjunct to intravenous combination therapy (ceftazidime and amikacin) in cystic fibrosis," Journal of Pediatrics, 111(4):599-605 (Oct. 1987).
Schentag, J. J., Antimicrobial action and pharmacokinetics/pharmacodynamics: the use of AUIC to improve efficacy and avoid resistance, Journal of Chemotherapy, 11(6):426-439 (1999).
Schiffelers, R. et al., "Liposome-encapsulated aminoglycosides in pre-clinical and clinical studies," Journal of Antimicrobial Chemotherapy, 48:333-344 (2001).
Schiffelers, R. M. et al., "Therapeutic efficacy of liposomal gentamicin in clinically relevant rat models," International Journal of Pharmaceutics, 214:103-105 (2001).
Schiffelers, R. M. et al., "In vivo synergistic interaction of liposomecoencapsulated gentamicin and ceftazidime," Journal Pharmacology Experimental Therapeutics, 298(1):369-375 (2001).
Schlegel, L. et al., "In-vitro killing activity of combinations of beta-lactam agents with aminoglycosides against penicillin-resistant pneumococci," The Journal of Antimicrobial Chemotherapy, 39(1):95-98 (1997).
Schreier, H. et al., "Pulmonary delivery of amikacin liposomes and acute liposome toxicity in the sheep," International Journal of Pharmaceutics, 87(1-3):183-193 (1992).
Schreier, H. et al., "Pulmonary delivery of liposomes," Journal of Controlled Release, 24(1):209-223 (1993).
Sermet-Gaudelus, I. et al., "Nebulized antibiotics in cystic fibrosis," Pediatric Drugs, 4(7):455-467 (2002).
Sezer et al., "Encapsulation of Enrofloxacin in Liposomes I: Preparation and In Vitro Characterization of LUV," Journal of Liposome Research, 14(1-2):77-86 (2004).
Shah, S. P. et al., "Liposomal amikacin dry powder inhaler: effect of fines on in vitro performance," AAPS PharmSciTech, 5(4):e65:1-7 (2004).
SHEK et al., "Liposomes in Pulmonary Applications: Physiochemical Considerations, Pulmonary Distribution and Antioxidant Delivery," Journal of Drug Targeting, 2:431-442 (1994).
Shima, K. et al., "A study of amikacin (BB-K8) on the clinical effects on the respiratory infection," Chemotherapy, 23(6):2128-2130 (1975) (with English Abstract).
Singh, P. K. et al., "Quorum-sensing signals indicate that cystic fibrosis lungs are infected with bacterial biofilms," Nature, 407:762-764 (2000).
Skubitz, K. M. et al., "Inhalational interleukin-2 liposomes for pulmonary metastases: a phase I clinical trial," Anti-Cancer Drugs, 11(7): 555-563 (2000).
Smith, A. L. et al., "Safety of aerosol tobramycin administration for 3 months to patients with cystic fibrosis," Pediatric Pulmonology, 7(4):265-271 (1989).
Smith et al. (1986). Pharmacokinetics and sputum penetration of ciprofloxacin in patients with cystic fibrosis. Antimicrobial Agents and Chemotherapy 30(4), pp. 614-616.
Stark, B., "Long-term stability of sterically stabilized liposomes by freezing and freeze-drying: Effects of cryoprotectants on structure," Eur. J. Pharm. Sci. 41:546-555 (2010).
Stott, P. W. et al., "Characterization of complex coacervates of some tricyclic antidepressants and evaluation of their potential for enhancing transdermal flux," Journal of Controlled Release, 41(3):215-227 (1996).
Strauss, G., "Stabilization of lipid bilayer by sucrose during freezing," PNAS (1986) 83:2422-2426.
Sunamoto et al., "Unexpected Tissue Distribution of Liposomes Coated With Amylopectin Derivatives And Successful Use In The Treatment Of Experimental Legionnaires' Diseases," Receptor-Mediated Targeting of Drugs, vol. 82, pp. 359-371 (G. Gregoriadis et al. eds., 1984).
Sunamoto et al., "Improved drug delivery directed to specific tissue using polysaccharide-coated liposomes," Multiphase Biomedical Materials, pp. 167-190 (T. Tsuruta et al. eds., 1989).

(56) References Cited

OTHER PUBLICATIONS

Sweeney et al. (2005). Spray-freeze-dried liposomal ciprofloxacin powder for inhaled aerosol drug delivery. International Journal of Pharmaceutics 305, pp. 180-185.
Swenson, K. A. et al., "Pharmacokinetics and in vivo activity of liposome-encapsulated gentamicin," Antimicrobial Agents and Chemotherapy, 34(2)235-240 (1990).
Swenson, C. E. et al., "Liposomal aminoglycosides and TLC G-65," Aids Patient Care, pp. 290-296 (1991).
Szoka, F. Jr. et al., "Comparative properties and methods of preparation of lipid vesicles (liposomes)," Ann. Rev. Biophys. Bioeng., 9:467-508 (1980).
Szoka, F. Jr. et al., "Procedure for preparation of liposomes with large internal aqueous space and high capture by reverse-phase evaporation," PNAS USA, 75(9):4194-4198 (Sep. 1978).
Tarran, R., "Regulation of Airway Surface Liquid Volume and Mucus Transport by Active Ion Transport," Proc. Am. Thorac. Soc., vol. 1, pp. 42-46, 2004.
Takamoto, M. et al., "Imipenem/cilastatin sodium alone or combined with amikacin sulfate in respiratory infections," The Japanese Journal of Antibiotics, 47(9):1131-1144 (1994) (with English Abstract).
Tateda, K. et al., "Efficacy of beta-lactam antibiotics combined with gentamicin against penicillin-resistant pneumococcal pneumonia in CBA/J mice," The Journal of Antimicrobial Chemotherapy, 43(3):367-371 (1999).
Taylor, K. M. G. et al., "The influence of liposomal encapsulation on sodium cromoglycate pharmacokinetics in man," Pharmaceutical Research, 6(7):633-636 (1989).
Ten, R. M. et al., "Interleukin-2 liposomes for primary immune deficiency using the aerosol route," International Immunopharmacology, 2(2-3):333-344 (2002).
Terzano, C. et al., "Tobramycin aerosol: could the delivery system influence the particle size and deposition in the lower aira/ays?" Recenti. Prog. Med., 89(5):245-249 (1998) (English Abstract).
Thomas, D. A. et al., "Acute effects of liposome aerosol inhalation on pulmonary function in healthy human volunteers," Chest, 99(5):1268-1270 (1991).
Thomasin, C. et al., "Drug microencapsulation by PLA/PLGA coacervation in the light of thermodynamics. 2. Parameters determining microsphere formation," Journal of Pharmaceutical Sciences, 87(3):269-275 (1998).
Trafny, E. A. et al., "Effects of free and liposome-encapsulated antibiotics on adherence of Pseudomonas aeruginosa to collagen type I," Antimicrobial Agents and Chemotherapy, 39(12):2645-2649 (1995).
Ulrich, A. S., "Biophysical aspects of using liposomes as delivery vehicles," Bioscience Reports, 22(2): 129-150 (Apr. 2002).
Van Der Straeten, M. et al., "Amikacin in the treatment of gram-negative bronchopulmonary infections," The Journal of Infectious Diseases, 134:S391-S393 (1976).
Van Heeckeren, A et al., "Effects of bronchopulmonary inflammation induced by Pseudomonas aeruginosa on adenovirus-mediated gene transfer to aira/ay epithelial cells in mice," Gene Ther., 5(3):345-351 (Mar. 1998).
Van Heeckeren, A. et al., "Delivery of CFTR by adenoviral vector to cystic fibrosis mouse lung in a model of chronic Pseudomonas aeruginosa lung infection," Am J Physiol Lung Cell Mol Physiol. Apr. 2004;286(4):L717-26. Epub Sep. 26, 2003.
Van Heeckeren, A. et al., "Effect of Pseudomonas infection on weight loss, lung mechanics, and cytokines in mice," Am J Respir Crit Care Med. Jan. 2000;161(1):271.
Van Heeckeren, A. et al., "Murine models of chronic Pseudomonas aeruginosa lung infection," Lab Anim., 36(3):291-312 (Jul. 2002).
Van Heeckeren, A. et al., "Role of CFTR genotype in the response to chronic Pseudomonas aeruginosa lung infection in mice," Am J Physiol Lung Cell Mol Physiol. Nov. 2004;287(5): L944-52. Epub Jul. 9, 2004.
Vecellio, L., "The mesh nebuliser: a recent technical innovation for aerosol delivery," Breathe, 2(3):253-260 (2006).
Veldhuizen, R. et al., "The role of lipids in pulmonary surfactant," Biochimica et Biophysica Acta, 1408:90-108 (1998).
Vidgren, M. et al., "A study of 99m technetium-labelled bedomethasone dipropionate dilauroylphosphatidylcholine liposome aerosol in normal volunteers," International Journal of Pharmaceutics, 115:209-216 (1995).
Vitas, A. I. et al., "Effect of composition and method of preparation of liposomes on their stability and interaction with murine monocytes infected with *Brucella abortus*," Antimicrobial Agents and Chemotherapy, 40(1):146-151 (1996).
Wang, W. et al., "Research progress in pulmonary administration of liposome," Journal of Shenyang Pharmaceutical University, 17(3):226-229 (2000).
Wang, Z. et al., "Improved drug delivery: Spray freeze dried nano-liposomal inhaled aerosols," Proceedings of the 2004 International Conference on MEMS, NANO and Smart Systems (ICMENS 2004), Badawy W. et al. (eds.), (University of Calgary), 1 page.
Webb, M. S. et al., "Antibacterial Efficacy against an In Vivo Salmonella typhimurium Infection Model and Pharmacokinetics of a Liposomal Ciprofloxacin Formulation," Antimicrobial Agents and Chemotherapy, 42(1):45-52 (Jan. 1998).
Weber et al. (1997). Effect of nebulizer type and antibiotic concentration on device performance. Pediatric Pulmonology 23, pp. 249-260.
Weber, A. et al., "Nebulizer delivery of tobramycin to the lower respiratory tract," Pediatr Pulmonol., 17(5):331-339 (May 1994).
Wichert, B. V. et al., "Amikacin liposomes: characterization, aerosolization, and in vitro activity against *Mycobacterium avium*-intracellulare in alveolar macrophages," International Journal of Pharmaceutics, 78(1-3):227-235 (1992).
Wise et al. (1983). In vitro activity of Bay 09867, a new quinolone derivate compared with those of other antimicrobial agents. Antimicrobial Agents and Chemotherapy 23(4), pp. 559-564.
Westerman, E. M. et al., "Effect of nebulized colistin sulphate and colistin sulphomethate on lung function in patients with cystic fibrosis: a pilot study," Journal of Cystic Fibrosis, 3(1):23-28 (2004).
Whitehead, T. C. et al., "Kinetics and Toxicity of Liposomal and Conventional Amikacin in a Patient with Multidrug-Resistant Tuberculosis," Eur J Clin Microbiol. Infect. Dis., 17:794-797 (1998).
Winthrop, K. L. et al., "Subgroup Analyses of Baseline Demographics and Efficacy in Patients With Refractory Nontuberculous Mycobacteria (NTM) Lung Infection Treated With Liposomal Amikacin for Inhalation (LAI)," Poster presented at the ATS 2015 International Conference, May 15-20, 2015, Denver, Co, USA, 1 page.
Winthrop, K. L. et al., "Subgroup Analyses of Baseline Demographics and Efficacy in Patients With Refractory Nontuberculous Mycobacteria (NTM) Lung Infection Treated With Liposomal Amikacin for Inhalation (LAI)," Abstract, Diagnosis and Management of Nontuberculous Mycobacteria Infections, Poster Discussion Session, May 20, 2015, Colorado Convention Center, Am J Respir Crit Care Med 191;2015:A6294, Online Abstracts Issue, 2 pages.
Wolff, R. K. et al., "Toxicologic testing of inhaled pharmaceutical aerosols," Critical Reviews in Toxicology, 23(4):343-369 (1993).
Wolkers, W. F. et al., "Preservation of dried liposomes in the presence of sugar and phosphate," Biochimica et Biophysica Acta, 1661:125-134 (2004).
Wong et al., "Liposome delivery of ciprofloxacin against intracellular Francisella tularensis infection," Journal of Controlled Release, 92(3):265-273 (2003).
Worlitzsch, D. et al., "Effects of reduced mucus oxygen concentration in airway pseudomonas infections of cystic fibrosis patients," J. Clin. Invest., 109:317-325 (2002).
Xiu, L. et al., "Drug Resistant Analysis of Pseudomonas Aeruginosa in Patients with Mechanical Ventilation," Med. J. Chin. PLA, 27(6):544-545 (2002) (with English Abstract).
Yamazaki, Y. et al., "The ability to form biofilm influences *Mycobacterium avium* invasion and translocation of bronchial epithelial cells," Cellular Microbiology, 8(5):806-814 (2006).
Yanagihara, K. et al., "Design of anti-bacterial drug and anti-Mycobacterial drug for drug delivery system," Current Pharmaceutical Design, 8:475-482 (2002).

(56) References Cited

OTHER PUBLICATIONS

Yim, D. et al., "The Development of Inhaled Liposome-Encapsulated Ciprofloxacin to Treat Cystic Fibrosis," Respiratory Drug Delivery, pp. 425-428 (2006).
Yu et al., "The Effect of Temperature and pH on the Solubility of Quinolone Compounds: Estimation of Heat of Fusion," Pharmaceutical Research, vol. 11, No. 4, pp. 522-527 (1994).
Zeng, S. et al., "Intravitreal Pharmacokinetics of Liposome-encapsulated Amikacin in a Rabbit Model," Ophthamology, 100:1640-1644 (1993).
Zhanel et al., "A Critical Review of the Fluoroquinolones Focus on Respiratory Tract Infections," Drugs, 62(1):13-59 (2002).
Zhang, J. H. et al., "A Novel Method to Prepare Liposomes Containing Amikacin," Journal Microencapsulation, 16(4):511-516 (1999).
Zhang, X. et al., "Antibacterial drug treatment of community acquired pneumonia," Chinese Journal of Respiratory and Critical Care Medicine, 4(4):258-260 (2005).
Zhigaltsev, I. V. et al., "Formation of drug-arylsulfonate complexes inside liposomes: A novel approach to improve drug retention," Journal of Controlled Release, 110:378-386 (2006). Available online Nov. 28, 2005.
Xie, C., Respiratory Diseases, Scientific and Technological Documentation Press, Jun. 2000, pp. 79-81, Chapter II Section XI *Pseudomonas aerugiosa* Pneumonia.
Zlatanov, Z. et al., "Gentamycin-pharmachim. Aerosol inhalation treatment of patients with chronic bronchitis," Medico Biologic Information 2, pp. 5-8 (1976).
Abranches, J. et al., "Invasion of human coronary artery endothelial cells by *Streptococcus mutans* OMZ175," Oral Microbiol Immunol. Apr. 2009; 24(2):141-145. doi:10.1111/j.1399-302X.2008.00487.X.
Ahmad, S. et al., "Azithromycin effectiveness against intracellular infections of Francisella," BMC Microbiology 2010, 10:123.
Bahar, A. A. et al., "Antimicrobial peptides," Pharmaceuticals 2013, 6:1543-1575; doi:10.3390/ph6121543.
Chi, F. et al., "Vimentin-mediated signalling is required for IbeA+ *E. coli* K1 invasion of human brain microvascular endothelial cells," Biochem. J. (2010) 427, 79-90 (Printed in Great Britain) doi:10.1042/BJ20091097.
Cordeiro, C. et al., "Antibacterial Efficacy of Gentamicin Encapsulated in pH-Sensitive Liposomes against an In Vivo *Salmonella enterica* Serovar Typhimurium Intracellular Infection Model," Antimicrobial Agents and Chemotherapy, Mar. 2000, vol. 44, No. 3, p. 533-539.
Deshpande, R. G. et al., "Invasion of Aortic and Heart Endothelial Cells by Porphyromonas gingivalis," Infection and Immunity, Nov. 1998, vol. 66, No. 11, p. 5337-5343.
Domingue, G. J. et al., "Bacterial Persistence and Expression of Disease," Clinical Microbiology Reviews, Apr. 1997, vol. 10, No. 2, p. 320-344.
Dorn, B. R. et al., "Invasion of Human Coronary Artery Cells by Periodontal Pathogens," Infection and Immunity, Nov. 1999, vol. 67, No. 11, p. 5792-5798.
Samoshina, N. M. et al., "Fliposomes: pH-Sensitive Liposomes Containing a trans-2-morpholinocyclohexanol-Based Lipid That Performs a Conformational Flip and Triggers an Instant Cargo Release in Acidic Medium," Pharmaceutics 2011, 3, 379-405; doi:10.3390/pharmaceutics3030379.
Helguera-Repetto, A. C. et al., (May 2014) "Differential Macrophage Response to Slow- and Fast-Growing Pathogenic Mycobacteria," Hindawi Publishing Corporation, BioMed Research International, vol. 2014, Article ID 916521,10 pages, http://dx.doi.org/10.1155/2014/916521.
Jo, E-K., "Innate immunity to mycobacteria: vitamin D and autophagy," Cellular Microbiology (2010) 12(8):1026-1035, doi:10.1111/j.1462-5822.2010.01491.x, First published online Jun. 15, 2010.
Kozarov, E., "Bacterial invasion of vascular cell types: vascular infectology and atherogenesis," Future Cardiol. Jan. 2012; 8(1):123-138. doi:10.2217/fca.11.75.
Leite, E. A. et al., "Encapsulation of cisplatin in long-circulating and pH-sensitive liposomes improves its antitumor effect and reduces acute toxicity," International Journal of Nanomedicine 2012:7 5259-5269.
Falkinham, J. O., III et al., "Mycobacterium avium in a shower linked to pulmonary disease," Journal of Water and Health, Jun. 2, 2008, pp. 209-213, 2008.
Martin, D. W. et al., "Invasion and Intracellular Survival of Burkholderia cepacia," Infection and Immunity, Jan. 2000, vol. 68, No. 1, p. 24-29.
Nahire, R. et al., "pH-Triggered Echogenicity and Contents Release from Liposomes," Mol. Pharmaceutics 2014, 11, 4059-4068.
Nakano, K. et al., "Detection of Cariogenic *Streptococcus mutans* in Extirpated Heart Valve and Atheromatous Plaque Specimens," Journal of Clinical Microbiology, Sep. 2006, vol. 44, No. 9, p. 3313-3317.
Niu, J. et al., "Role of MCP-I in cardiovascular disease: molecular mechanisms and clinical implications," Clinical Science (2009) 117:95-109 (Printed in Great Britain) doi:10.1042/CS20080581.
Oswald-Richter, K. A. et al., "Multiple mycobacterial antigens are targets of the adaptive immune response in pulmonary sarcoidosis," Respiratory Research 2010, 11:161.
Pierce, E. S., "Where Are All the *Mycobacterium avium* Subspecies *paratuberculosis* in Patients with Crohn's Disease?," Mar. 2009, PLoS Pathogens 5(3):e1000234. doi:10.1371/journal.ppat. 1000234.
Pujol, C. et al., "Yersinia pestis Can Reside in Autophagosomes and Avoid Xenophagy in Murine Macrophages by Preventing Vacuole Acidification," Infection and Immunity, Jun. 2009, vol. 77, No. 6, p. 2251-2261.
Pollock, S. et al., "Uptake and trafficking of liposomes to the endoplasmic reticulum," FASEB J. 24, 1866-1878 (2010).
Rahman, S. A. et al., "Comparative Analyses of Nonpathogenic, Opportunistic, and Totally Pathogenic Mycobacteria Reveal Genomic and Biochemical Variabilities and Highlight the Survival Attributes of *Mycobacterium tuberculosis*," mBio, Nov./Dec. 2014, 5(6):e02020-14. doi:10.1128/mBio.02020.
Rose, S. J. et al., "Delivery of Aerosolized Liposomal Amikacin as a Novel Approach for the Treatment of Nontuberculous Mycobacteria in an Experimental Model of Pulmonary Infection," Sep. 2014, PLoS ONE 9(9): e108703. doi:10.1371/journal.pone.0108703.
Savage, P. B. et al., "Antibacterial properties of cationic steroid antibiotics," FEMS Microbiology Letters 217 (2002) 1-7.
Simoes, S. et al., "On the formulation of pH-sensitive liposomes with long circulation times," Advanced Drug Delivery Reviews 56 (2004) 947-965.
Sudimack, J. J. et al., "A novel pH-sensitive liposome formulation containing oleyl alcohol," Biochimica et Biophysica Acta 1564 (2002) 31-37.
Gerasimov, O. V. et al., "Cytosolic drug delivery using pH- and light-sensitive liposomes," Advanced Drug Delivery Reviews 38 (1999) 317-338.
Zeituni, A. E. et al., "Porphyromonas gingivalis-dendritic cell interactions: consequences for coronary artery disease," Journal of Oral Microbiology 2010, 2: 5782. doi: 10.3402/jom.v2i0.5782.
Anderson, K. E. et al., "Formulation and Evaluation of a Folic Acid Receptor-Targeted Oral Vancomycin Liposomal Dosage Form," Pharmaceutical Research, 18(3):316-322 (2001).
Vancomycin (Systemic), VA Classification Primary: AM900, Drugs. com [online], Retrieved from the Internet on Apr. 7, 2011: <URL: http://www.drugs.com/mmx/vancomycin-hydrochloride.html?printable=1>, dated Jun. 15, 1999, 15 pages.
Harris, C. M. et al., "The stabilization of vancomycin by peptidoglycan analogs," J Antibiot (Tokyo). Jan. 1985;38(1):51-57.
Jones, M. N., "Use of Liposomes to Deliver Bactericides to Bacterial Biofilms," Methods of Enzymology, 391:211-228 (2005).
Kadry, A. A. et al., "Treatment of experimental osteomyelitis by liposomal antibiotics," Journal of Antimicrobial Chemotherapy, 54(6):1103-1108 (2004).
Levy, D. E. et al., "PEGylated iminodiacetic acid zinc complex stabilizes cationic RNA-bearing nanoparticles," Bioorganic & Medicinal Chemistry Letters, 20:5499-5501 (Jul. 2010).

(56) References Cited

OTHER PUBLICATIONS

Maiz, L. et al., "Aerosolized vancomycin for the treatment of methicillin-resistant staphylococcus aureus infection in cystic fibrosis," Pediatric Pulmonology, 26(4):287-289 (1998).
Onyeji, C. O. et al., "Enhanced killing of methicillin-resistant *Staphylococcus aureus* in human macrophages by liposome-entrapped vancomycin and teicoplanin," Infection, 22(5):338-342 (1994).
Sanderson, N. M. et al., "Encapsulation of vancomycin and gentamicin within cationic liposomes for inhibition of growth of *Staphylococcus epidermidis*," Journal of Drug Targeting, 4(3):181-189 (1996).
Takeuchi, Y. et al., "Stabilizing effects of some amino acids on membranes of rabbit erythrocytes perturbed by chlorpromazine," J Pharm Sci. Jan. 1989;78(1):3-7.
Weiner, A. L., "Liposomes as carriers for polypeptides," Advanced Drug Delivery Review, 3(3):307-341 (May-Jun. 1989).
Extended European Search Report for European Application No. 17207115.1, dated Jun. 1, 2018, 10 pages.
Novosad, S. et al., "The Challenge of Pulmonary Nontuberculous Mycobacterial Infection," Curr Pulmonol Rep. Sep. 1, 2015; 4(3): 152-161. doi:10.1007/s13665-015-0119-3.
Griffith, D. E. et al., "An Official ATS/IDSA Statement: Diagnosis, Treatment, and Prevention of Nontuberculous Mycobacterial Diseases," Am J Respir Crit Care Med., vol. 175. pp. 367-416, 2007.
Extended European Search Report for European Application No. 18176134.7, dated Nov. 22, 2018, 12 pages.
Griffith, D. E. et al., "Amikacin Liposome Inhalation Suspension for Treatment-Refractory Lung Disease Caused by Mycobacterium avium Complex (CONVERT): A Prospective, Open-Label, Randomized Study," AJRCCM Articles in Press. Published on Sep. 14, 2018 as 10.1164/rccm.201807-13180C, American Thoracic Society, 72 pages.
Olivier, K. N. et al., "Inhaled amikacin for treatment of refractory pulmonary nontuberculous mycobacterial disease," Ann. Am. Thorac. Soc., vol. 11, No. 1, pp. 30-35 (Jan. 2014).
Extended European Search Report for European Application No. 18203799.4, dated Mar. 13, 2019, 14 pages.
Extended European Search Report for European Application No. 16822088.7, dated Feb. 15, 2019, 7 pages.
International Search Report and Written Opinion for International Application No. PCT/US2019/030404, dated Jul. 2, 2019, 8 pages.
Davis, K. K. et al., "Aerosolized amikacin for treatment of pulmonary *Mycobacterium avium* infections: an observational case series," BMC Pulmonary Medicine 2007, 7:2; doi: 10.1186/1471-2466-7-2.
Extended European Search Report for European Application No. 19167132.0, dated Nov. 20, 2019, 8 pages.
Duzgunes, Liposomes, Part A, Methods in Enzymology, Disalvo, E. A. et al., "Interfacial properties of liposomes as measured by fluorescence and optical probes," Chapter 14, pp. 213-232 (2003).
Geller, D. E. et al., Guidance on the Use of eFlow Nebulizers (Altera® and Trio®), Apr. 6, 2010, 5 pages.
Heyes, J. et al., "Cationic lipid saturation influences intracellular delivery of encapsulated nucleic acids," Journal of Controlled Release, 107:276-287 (2005).

Pediatric Pulmonology 2010, vol. 45, Issue S33, The 24th Annual North American Cystic Fibrosis Conference, Baltimore Convention Center, Baltimore, Maryland, Oct. 21-23, 2010, p. 306, among pp. 1-477, No. 243-abstract: Minic, P. et al., "A multi-cycle open label study of nebulized liposomal amikacin (Arikace™) in the treatment of cystic fibrosis patients with chronic pseudomonas aeruginosa lung infection."
Wan, C. et al., "Lipid nanoparticle delivery systems for siRNA-based therapeutics," Drug Deliv. and Transl. Res., 4(1):74-83 (Feb. 2014).
Zhang, J. et al., "Amikacin Liposome Inhalation Suspension (ALIS) Penetrates Non-tuberculous Mycobacterial Biofilms and Enhances Amikacin Uptake Into Macrophages," Frontiers in Microbiology, May 2018, vol. 9, Article 915, 12 pages.
Extended European Search Report for European Application No. 20159434.8, dated Aug. 12, 2020, 7 pages.
Bilton, D. et al., "Phase 3 Efficacy and Safety Data from Randomized, Multicenter Study of Liposomal Amikacin for Inhalation (Arikace) Compared with TOBI in Cystic Fibrosis Patients with Chronic Infection Due to Pseudomanas aeruginosa," Poster 235, North American Cystic Fibrosis Conference, Salt Lake City, Utah, Oct. 2014, 1 page.
Jeffs, L. B. et al., "A Scalable, Extrusion-Free Method for Efficient Liposomal Encapsulation of Plasmid DNA," Pharmaceutical Research, vol. 22, No. 3, Mar. 2005, pp. 362-372.
Levin, A. M. et al., "Association of ANXA11 genetic variation with sarcoidosis in African Americans and European Americans," Genes and Immunity, 2013, vol. 14, No. 1, pp. 13-18.
Minic, P., "A multi-cycle open label study of nebulized liposomal amikacin (Arikace) in the treatment of cystic fibrosis patients with chronic pseudomonas aeruginosa lung infection," Pediatric Pulmonology, vol. 45, Issue S33, Special Issue: The 24th Annual North American Cystic Fibrosis Conference, Baltimore Convention Center, Baltimore, Maryland, Oct. 21-23, 2010, Dec. 2010, p. 306.
Mrazek, F. et al., "Functional variant ANXA11 R230C: true marker of protection and candidate disease modifier in sarcoidosis," Genes and Immunity, 2011, vol. 12, No. 6, pp. 490-494.
Zhang, G. et al., "Performance of the vibrating membrane aerosol generation device: Aeroneb Micropump nebulizer," Journal of Aerosol Medicine, vol. 20, No. 4, 2007, pp. 408-416.
Zhou, L., Guidance for Industry, Liposome Drug Products, Chemistry, Manufacturing, and Controls; Human Pharmacokinetics and Bioavailability; and Labeling Documentation, Draft Guidance, U.S. Department of Health and Human Services, Aug. 2002, 15 pages.
Presant, C. A. et al., "Chapter 18: Design of Liposome Clinical Trials," In: Liposome Technology, Entrapment of Drugs and Other Materials, Gregoriadis, G. (ed.),vol. II, 2nd Edition, CRC Press, Inc., 1993, pp. 307-317.
New, R. R. C., "Chapter 2: Preparation of Liposomes," In: Liposomes: A Practical Approach, IRL Press at Oxford University Press, 1990, pp. 33-104.
Xu, X. et al., "Chapter 11: Liposomes as Carriers for Controlled Drug Delivery," Wright, J. C. et al. (eds.), Long Acting Injections and Implants, Advances in Delivery Science and Technology, 2012, pp. 195-222.
Extended European Search Report for European Application No. 20182665.8, dated Dec. 23, 2020, 9 pages.

METHODS FOR CONTINUOUS MANUFACTURE OF LIPOSOMAL DRUG PRODUCTS

CROSS REFERENCE TO RELATED APPLICATION

This application is a U.S. National Phase of PCT/US2019/024901, filed Mar. 29, 2019, which claims priority from U.S. Provisional Application Ser. No. 62/650,372, filed Mar. 30, 2018, the disclosure of which is incorporated by reference herein in their entireties for all purposes.

BACKGROUND OF THE INVENTION

Continuous manufacturing is a process whereby raw materials constantly flow into a process and intermediates or final product constantly flow out. Such processing has been employed in non-pharmaceutical industries and has recently been adopted in some types of pharmaceutical processes such as the synthesis of active pharmaceutical ingredients (APIs) and generation of solid oral dosage forms (tablets, etc.) (Kleinebudde et al. (Eds.), *Continuous Manufacturing of Pharmaceuticals*, Wiley-VCH, Hoboken 2017; Subramanian, G. (Ed.), *Continuous Process in Pharmaceutical Manufacturing*, Wiley-VCH, Weinheim 2015).

In recent history, continuous manufacturing has been used for the production of biologics. The manufacture of biologics has continued to develop the requirements and aspects to consider surrounding unit operations such as cell culture, chromatography, viral inactivation and various methods for tangential flow filtration (TFF), such as alternating tangential filtration (ATF) and single pass tangential flow filtration (SPTFF) (Subramanian, G. (Ed.), *Continuous Process in Pharmaceutical Manufacturing*, Wiley-VCH, Weinheim 2015)). ATF, for example, is a means of performing buffer/medium exchange with lower shear forces as compared to TFF. Continuous perfusive cell culture has used ATF to support continuous medium exchange with highly concentration suspensions (Castilho, Continuous Animal Cell Perfusion Processes: The First Step Toward Integrated Continuous Manufacturing, in: Subramanian, G. (Ed.), *Continuous Process in Pharmaceutical Manufacturing*, Wiley-VCH, Weinheim 2015, pp. 115-153; Whitford, Single-Use Systems Support Continuous Bioprocessing by Perfusion Culture, in: Subramanian, G. (Ed.), *Continuous Process in Pharmaceutical Manufacturing*, Wiley-VCH, Weinheim 2015, pp. 183-226).

Single pass tangential flow filtration (SPTFF) has been evaluated as well for concentrating protein, allowing this process step to happen in a continuous fashion instead of the batch mode required by traditional TFF (Brower et al. Monoclonal Antibody Continuous Processing Enabled by Single Use, in: Subramanian, G. (Ed.), *Continuous Process in Pharmaceutical Manufacturing*, Wiley-VCH, Weinheim 2015, pp. 255-296: Jungbauer, Continuous downstream processing of biopharmaceuticals. *Trends in Biotechnolgy.* 2013, 8, 479-492; Dizon-Maspat et al., Single pass tangential flow filtration to debottleneck downstream processing for therapeutic antibody production. *Biotechnol Bioeng.* 2012, 4, 962-70).

Other aspects for commercial implementation of continuous manufacturing such as a process analytical technology (PAT) requirement and use of single-use or disposable componentry have been explored. The implementation of single-use or disposable technology provides the same conceptual benefits as it would for a batch process, but increased in magnitude as more product is generated per single-use/disposable item.

The present invention addresses the need for a continuous manufacturing process for liposomal active pharmaceutical ingredients (liposomal APIs), such as liposomal drug products.

SUMMARY OF THE INVENTION

In one aspect of the invention, a method for manufacturing a liposomal API formulation in a continuous manner is provided.

One embodiment of the method for manufacturing the liposomal API formulation comprises mixing a lipid solution comprising a lipid dissolved in an organic solvent with an aqueous API solution, wherein the lipid solution and aqueous API solution are mixed from two separate streams in an in-line fashion, and wherein a liposomal encapsulated API is formed at the intersection of the two streams. The method further comprises introducing the liposomal encapsulated API into a central vessel comprising a first inlet, a second inlet, a first outlet and a second outlet, through the first inlet. The first outlet of the central vessel is in fluid communication with an inlet of a first tangential flow filtration (TFF) unit. The first TFF unit comprises the aforementioned inlet and a first and second outlet. The first outlet of the first TFF unit is in fluid communication with the second inlet of the central vessel and the second outlet of the first TFF unit is a waste outlet. The second outlet of the central vessel is in fluid communication with an inlet of a second TFF unit comprising the inlet and a first and second outlet. The first outlet of the second TFF unit is a retentate outlet and the second outlet of the second TFF unit is a waste (permeate) outlet. The method further comprises continuously flowing the liposomal encapsulated API into the first TFF unit for a first period of time. The liposomal encapsulated API enters the first TFF unit through the TFF inlet and exits through the first outlet. The method further comprises flowing the liposomal encapsulated API from the central vessel through the inlet of the second TFF unit for a second period of time and collecting the liposomal API formulation from the first outlet of the second TFF unit.

In one embodiment, the method comprises flowing the liposomal encapsulated API from the central vessel into one or more additional TFF units prior to flowing the liposomal API formulation into the second TFF unit.

In one embodiment, the second TFF unit is a single pass TFF unit (SPTFF).

In a second embodiment, the method for manufacturing the liposomal API formulation comprises mixing a lipid solution comprising a lipid dissolved in an organic solvent with an aqueous API solution, wherein the lipid solution and aqueous API solution are mixed from two separate streams in an in-line fashion, and wherein a liposomal encapsulated API is formed at the intersection of the two streams. The method further comprises introducing the liposomal encapsulated API into a central vessel comprising an inlet and an outlet, through the inlet. The outlet is in fluid communication with an inlet of a first tangential flow filtration (TFF) unit. The first TFF unit comprises the aforementioned inlet and a first and second outlet. The first outlet of the first TFF unit is in fluid communication with the inlet of a second TFF and the second outlet of the first TFF unit is a waste (permeate) outlet. The second TFF comprises the aforementioned inlet and a first and second outlet. The first outlet of the second TFF unit is a retentate outlet and the second outlet of the second TFF unit is a waste (permeate) outlet. The method further comprises continuously flowing the liposomal encapsulated API into the first TFF unit for a first period of time. The liposomal encapsulated API enters the first TFF unit through the TFF inlet and exits through the first outlet. The method further comprises flowing the liposomal encapsulated API from the first outlet of the first TFF through the inlet of the second TFF unit for a second period of time and collecting the liposomal API formulation from the first outlet of the second TFF unit.

In a further embodiment, the method comprises flowing the liposomal encapsulated API from the central vessel into one or more additional TFF units prior to flowing the liposomal API formulation into the second TFF unit.

In one embodiment, the second TFF unit is a single pass TFF unit (SPTFF).

In a third embodiment, the method for manufacturing a liposomal API formulation comprises mixing a lipid solution comprising a lipid dissolved in an organic solvent with an aqueous API solution, wherein the lipid solution and aqueous API solution are mixed from two separate streams in an in-line fashion, and wherein liposomal encapsulated API is formed at the intersection of the two streams. The method further comprises introducing the liposomal encapsulated API into a central vessel comprising a first inlet, a second inlet, a first outlet and a second outlet, through the first inlet. The first outlet is in fluid communication with an inlet of a first tangential flow filtration (TFF) unit comprising the inlet and a first and second outlet. The first outlet of the first TFF unit is in fluid communication with the second inlet of the first central vessel and the second outlet of the first TFF unit is a waste outlet. The second outlet of the first central vessel is in fluid communication with a first inlet of a second central vessel. The second central vessel comprises the first inlet, a second inlet, a first outlet and a second outlet, and the first outlet of the second central vessel is in fluid communication with an inlet of a second tangential flow filtration (TFF) unit comprising the inlet and a first and second outlet. The first outlet of the second TFF unit is in fluid communication with the second inlet of the second central vessel, the second outlet of the second TFF unit is a waste outlet. The second outlet of the second central vessel is in fluid communication with an inlet of a third TFF unit comprising the inlet and a first and second outlet, the first outlet of the third TFF unit is a retentate outlet and the second outlet of the third TFF unit is a waste (permeate) outlet. The method further comprises continuously flowing the liposomal encapsulated API into the first TFF unit for a first period of time, wherein the liposomal encapsulated API enters the first TFF unit through the TFF inlet and exits through the first outlet. The method further comprises flowing the liposomal encapsulated API from the first central vessel into the second central vessel for a second period of time and continuously flowing the liposomal encapsulated API into the second TFF unit from the second central vessel for a third period of time. The liposomal encapsulated API enters the second TFF unit through the TFF inlet and exits through the first outlet. The method further comprises flowing the liposomal encapsulated API from the second central vessel through the inlet of the third TFF unit for a fourth period of time; and collecting the liposomal encapsulated API formulation from the first outlet of the third TFF unit.

In one aspect of the third embodiment, the method comprises flowing the liposomal encapsulated API from the second central vessel into one or more additional TFF units prior to flowing the liposomal API formulation into the third TFF unit.

In another aspect of the third embodiment, the third TFF unit is a single pass TFF unit (SPTFF).

In one embodiment of the methods provided herein, mixing the lipid solution and the aqueous API solution results in the formation of a API coacervate. In a further embodiment, the API coacervate initiates lipid bilayer formation around the API coacervate.

In one embodiment of the methods provided herein, the API is an aminoglycoside. In a further embodiment, the aminoglycoside is amikacin, or a pharmaceutically acceptable salt thereof. In even a further embodiment, the amikacin is amikacin sulfate.

In one embodiment of the methods provided herein, a buffer is introduced into the first central vessel through a third inlet prior to the first period of time or during the first period of time.

In another aspect of the invention, a liposomal API formulation made by a continuous method described herein, is provided.

DETAILED DESCRIPTION OF THE INVENTION

Figure 1:
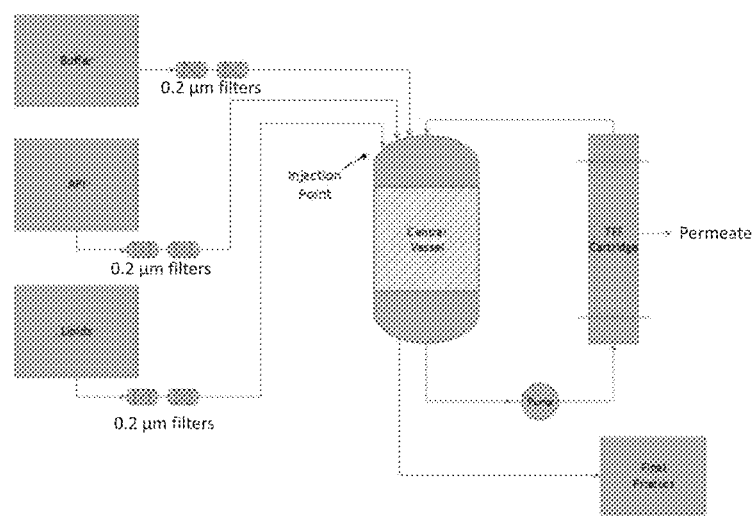
FIG. 1 is a liposomal API manufacturing process flow diagram. Ethanol/ether injection batch design method: lipid/solvent solution is directly fed into the central vessel. Formulations are refined in multi-step buffer exchange diafiltration and concentration steps.

The present invention, in one aspect, relates to the use of continuous manufacturing processes for the manufacture of liposomal API products. The potential benefits of implementing a continuous manufacturing process without wishing to be bound by theory, include economic advantages (lower capital expenditures, smaller facility footprint, lower overall cost of goods sold (COGS)), as well as improved consistency and quality of product.

In another aspect, a liposomal API formulation manufactured by a process provided herein is provided.

One aspect of the method for manufacturing the liposomal API formulation provided herein comprises an initial liposomal API encapsulation step. The liposomal API encapsulation, in one embodiment, comprises mixing a lipid solution comprising a lipid dissolved in an organic solvent with an aqueous API solution, wherein the lipid solution and aqueous API solution are mixed from two separate streams in an in-line fashion, and wherein a liposomal encapsulated API is formed at the intersection of the two streams. In another embodiment, the liposomal API encapsulation takes place in a central vessel via an alcohol injection method.

The method, in a first embodiment, comprises introducing a liposomal encapsulated API into a central vessel or forming a liposomal encapsulated API in the central vessel. The central vessel comprises a first inlet, a second inlet, a first outlet and a second outlet. The liposomal encapsulated API in one embodiment, is introduced through the first inlet of the central vessel.

The first outlet of the central vessel is in fluid communication with an inlet of a first tangential flow filtration (TFF) unit.

The terms "tangential flow filtration unit" or "TFF unit" are art-known and mean a device that includes at least one housing (such as a cylinder or cartridge) and at least one cross-flow (tangential) filter positioned in the housing such that a large portion of the filter's surface is positioned parallel to the flow of a fluid (e.g., a liposomal suspension) through the unit. In one embodiment, a TFF unit includes one filter. In another embodiment, a TFF unit includes two filters. In yet another embodiment, the TFF unit includes three filters. TFF units are well-known in the art and are commercially available, e.g., from Pall Life Sciences. The housing can include a first inlet/outlet and a second inlet/outlet positioned, e.g., to allow fluid to pass through the first inlet/outlet, cross the at least one cross-flow filter, and through the second inlet/outlet. In some examples, a circuit system can include multiple TFF units, e.g., connected in series and/or in parallel. In the methods provided herein, TFF units can be connected in series and/or parallel to provide a fluid path of desired length. For example, 4, 5, 6, 7, 8, 9 or 10 TFF units can be connected in parallel and/or series in the methods provided herein. In one embodiment, 6, 7, 8, 9, 10, 11, 12, 13, 14 or 15 TFF units are connected in parallel and/or series in the methods provided herein. In another embodiment, from about 5 to about 20 or from about 5 to about 15 TFF units are connected in series in one of the methods provided herein.

In one embodiment, a circuit system that includes two or more TFF units can include fluid conduits fluidly connecting neighboring pairs of TFF units in the system. In other examples, a circuit system can include two or more TFF units fluidly connected by fluid conduits. The TFF unit, in one embodiment, is a single pass TFF (SPTFF) unit. In another embodiment, the two or more TFF units comprise a TFF unit and a SPTFF unit.

The first TFF unit comprises the aforementioned inlet and a first and second outlet. The first outlet of the first TFF unit is the retentate outlet, and is in fluid communication with the second inlet of the central vessel and the second outlet of the first TFF unit is a waste (permeate) outlet. The second outlet of the central vessel is in fluid communication with an inlet of a second TFF unit comprising the inlet and a first and second outlet. The first outlet of the second TFF unit is a retentate outlet and the second outlet of the second TFF unit is a waste (permeate) outlet.

The method further comprises continuously flowing the liposomal encapsulated API into the first TFF unit for a first period of time. The liposomal encapsulated API enters the first TFF unit through the TFF inlet and exits through the first outlet. The method further comprises flowing the liposomal encapsulated API from the central vessel through the inlet of the second TFF unit for a second period of time and collecting the liposomal API formulation from the first outlet of the second TFF unit.

"Fluid communication" as used herein, means direct or indirect fluid communication, e.g., directly through a connection port or indirectly through a process unit such as a TFF unit, central vessel, etc.

In one embodiment, the method comprises flowing the liposomal encapsulated API from the central vessel into one or more additional TFF units prior to flowing the liposomal API formulation into the second TFF unit.

In one embodiment, the second TFF unit is a single pass TFF unit (SPTFF).

The method, in a second embodiment, comprises introducing a liposomal encapsulated API into a central vessel or forming a liposomal encapsulated API in the central vessel. The central vessel comprises an inlet and an outlet. The liposomal encapsulated API in one embodiment, is introduced through the inlet of the central vessel.

The outlet of the central vessel is in fluid communication with an inlet of a first tangential flow filtration (TFF) unit. The first TFF unit comprises the aforementioned inlet and a first and second outlet. The first outlet of the first TFF unit is in fluid communication with the inlet of a second TFF unit comprising the inlet and a first and second outlet. The first outlet of the second TFF unit is a retentate outlet and the second outlet of the second TFF unit is a waste (permeate) outlet.

The method further comprises continuously flowing the liposomal encapsulated API into the first TFF unit for a first period of time. The liposomal encapsulated API enters the first TFF unit through the TFF inlet and exits through the first outlet. The method further comprises flowing the liposomal encapsulated API from the first outlet of the first TFF through the inlet of the second TFF unit for a second period of time and collecting the liposomal API formulation from the first outlet of the second TFF unit.

In one embodiment, the method comprises flowing the liposomal encapsulated API from the central vessel into one or more additional TFF units prior to flowing the liposomal API formulation into the second TFF unit.

In one embodiment, the second TFF unit is a single pass TFF unit (SPTFF).

In a third embodiment of a continuous liposomal API formulation manufacturing method, the method comprises introducing the liposomal encapsulated API into a first central vessel or forming the liposomal encapsulated API in the first central vessel. The first central vessel comprises a first inlet, a second inlet, a first outlet and a second outlet. The liposomal encapsulated API in one embodiment is introduced into the central vessel through the first inlet. The first outlet of the first central vessel is in fluid communication with an inlet of a first tangential flow filtration (TFF) unit comprising the inlet and a first and second outlet. The first outlet of the first TFF unit is in fluid communication with the second inlet of the first central vessel and the second outlet of the first TFF unit is a waste (permeate) outlet. The second outlet of the first central vessel is in fluid communication with a first inlet of a second central vessel.

The second central vessel comprises the first inlet, a second inlet, a first outlet and a second outlet. The first outlet of the second central vessel is in fluid communication with an inlet of a second tangential flow filtration (TFF) unit comprising the inlet and a first and second outlet. The first outlet (retentate outlet) of the second TFF unit is in fluid communication with the second inlet of the second central vessel, the second outlet of the second TFF unit is a waste (permeate) outlet. The second outlet of the second central vessel is in fluid communication with an inlet of a third TFF unit comprising the inlet and a first and second outlet. The first outlet of the third TFF unit is a retentate outlet and the second outlet of the third TFF unit is a waste (permeate) outlet.

In this embodiment, the method further comprises continuously flowing the liposomal encapsulated API into the first TFF unit for a first period of time, wherein the liposomal encapsulated API enters the first TFF unit through the TFF inlet and exits through the first outlet. The method further comprises flowing the liposomal encapsulated API from the first central vessel into the second central vessel for a second period of time and continuously flowing the liposomal encapsulated API into the second TFF unit from the second central vessel for a third period of time. The liposomal encapsulated API enters the second TFF unit through the TFF inlet and exits through the first outlet. The method further comprises flowing the liposomal encapsulated API from the second central vessel through the inlet of the third TFF unit for a fourth period of time; and collecting the liposomal encapsulated API formulation from the first outlet of the third TFF unit.

The "first period of time". "second period of time", "third period of time" and "fourth period of time" can each be selected by the user of the method, depending in part on the selection of materials used to formulate the liposomal API, and/or the desired concentration of the liposomal API formulation. In one embodiment, the first period of time", "second period of time", "third period of time" and/or "fourth period of time" are each independently 1 h, 2 h, 3 h, 4 h, 5 h, 6 h, 8 h, 12 h, 18 h, 24 h, 36 h, 48 h, 60 h, 72 h, 84 h, 96 h or 108 h.

In each of the methods provided herein, an initial liposome formation step is employed. A variety of liposomal encapsulation methods are available to those of ordinary skill in the art, and can be employed herein. The liposomal encapsulation step, in one embodiment, is carried out upstream of an initial filtration step. The liposomal encapsulation, in one embodiment, takes place in a first central vessel. In another embodiment, the liposomal encapsulation takes place upstream of the first central vessel, and is provided to the first central vessel.

Liposomes were first discovered the early-1960s and a number of strategies have been demonstrated for their manufacture since (Mozafari. Liposomes: an overview of manufacturing techniques. *Cell Mol Biol Lett.* 2005, 10(4), 711-719; Maherani et al., Liposomes: A Review of Manufacturing Techniques and Targeting Strategies. *Current Nanoscience.* 2011, 7(3), 436-445: each of which is incorporated by reference herein in its entirety for all purposes).

Frequently, liposomal products are reformulations of compendial APIs meant to alleviate adverse clinical side effects and/or provide a more targeted delivery as compared to systemic dosages (Maurer et al. *Expert Opinion on Biological Therapy.* 2001, 6, 923-947; Lian and Ho. *Expert, J Pharm Sci.* 2001, 6, 667-680; each of which is incorporated by reference herein in its entirety for all purposes).

However, until recently, the application of liposomal products in pharmaceutical development has suffered from a lack of reliable manufacturing methods with sufficient throughput to enable commercial scale-up. Table 1 provides a summary of various liposome formation methods. In embodiments described herein, a liposomal API can be provided to the first central vessel or in the first central vessel via a supercritical fluid method, dense gas method, alcohol injection or crossflow method.

TABLE 1

| Liposome formation methods | | |
| --- | --- | --- |
| Method | Mechanism | Reference |
| Bangham | Rehydration of thin lipid film | Bangham et al., The action of steroids and streptolysin S on the permeability of phospholipid structures to cations. *J. Mol. Biol.* 1965, 13, 253-259. Bangham et al., Diffusion of univalent ions across the lamellae of swollen phospholipids. *J. Mol. Biol.* 1965, 13, 238-252. Deamerand Bangham, Large volume liposomes by an ether vaporization method. *Biochimica et Biophysica Acta.* 1976, 443, 629-634. |
| Sonication method | Sonication of an aqueous lipid suspension | Perrett et al. A simple method for the preparation of liposomes for pharmaceutical applications: characterization of the liposomes. *J Pharm Pharmacol.* 1991, 43(3), 154-161. |
| Reverse phase evaporation | Aqueous phase added to organic phase and evaporated to form liposomes | Meure et al., Conventional and dense gas technology for the production of liposomes: A review. *AAPS Pharma. Sci. Tech.* 2008, 9(3), 798-809. Szoka Jr. and Papahadjopoulos, Procedure for preparation of liposomes with large internal aqueous space and high capture by reverse-phase evaporation. *Proc. Natl. Acad. Sci.*, USA, 1978, 75(9), 4194-4198. |
| Detergent depletion | Liposomes formed through detergent lipid interaction | Brunner et al., Single bilayer vesicles prepared without sonication. Physico-chemical properties. *Biochim Biophys Acta.* 1976, 455(2), 322-331. Lasch et al., Preparaton of liposomes, in: Torchilin, V., Wessig, V. (Ed.), *Liposomes: A practical approach*, Oxford University Press, New York, 2003, p 3-29. |
| Microfluidic channel | Intersection of lipid/API solutions in micro-channels | Jahn et al., Microfluidic directed formation of liposomes of controlled size. *Langmuir.* 2007, 23(11), 6289-6293. |

TABLE 1-continued

Liposome formation methods

| Method | Mechanism | Reference |
|---|---|---|
| High pressure homogenization | Liposome formation through high pressure mixing | Barnadas-Rodriguez and Sabes, Factors involved in the production of liposomes with a high-pressure homogenizer. *Int. J. Pharma.* 2001, 213, 175-186.<br>Carugo et al., Liposome production by microfluidics: potential and limiting factors. *Scientific Reports.* 2016, 6, DOI: 10.1038/srep25876. |
| Heating method | Heating of a lipid aqueous/glycerol solution to form liposomes | Mozafari. Liposomes: an overview of manufacturing techniques. *Cell Mol Biol Lett.* 2005. 10(4), 711-719.<br>Mortazavi et al. Preparation of liposomal gene therapy vectors by a scalable method without using volatile solvents or detergents. *J. Biotechnol.* 2007, 129(4), 604-613.<br>Mozafari et al., Development of non-toxic liposomal formulations for gene and drug delivery to the lung. *Technol. Health Care.*, 2002, 10(3-4), 342-344. |
| Supercritical fluid methods | Use of supercritical fluids as solvent for lipids instead of organic solvents | Meure et al. Conventional and dense gas technology for the production of liposomes: A review. *AAPS Pharma. Sci. Tech.* 2008, 9(3), 798-809.<br>Santo et al. Liposomes Size Engineering by Combination of Ethanol Injection and Supercritical Processing. *J Pharm Sci.* 2015, 104(11), 3842-3850.<br>Santo et al. Liposomes prepration using a supercritical fluid assisted continuous process. *Chemical Engineering Journal.* 2014, 249, 153-159.<br>Campardelli et al., Efficient encapsulation of proteins in submicro liposomes using a supercritical fluid assisted continuous process. *The Journal of Supercritical Fluids.* 2016, 107, 163-169.<br>Frederiksen et al. Preparation of Liposomes Encapsulating Water-Soluble Compounds Using Supercritical Carbon Dioxide. *Journal of Pharmaceutical Sciences.* 1997, 86(8), 921-928.<br>Otake et al., Development of a new preparation method of liposomes using supercritical carbon dioxide. *Langmuir.* 2001, 17(13), 3898-3901. |
| Dense Gas methods | Use of dense gas as solvent for lipids instead of organic solvents | Meure et al., Conventional and dense gas technology for the production of liposomes: A review. *AAPS Pharma. Sci. Tech.* 2008, 9(3), 798-809.<br>Otake et al., Development of a new preparation method of liposomes using supercritical carbon dioxide. *Langmuir.* 2001, 17(13), 3898-3901.<br>Anton et al., *Preparation of a liposome dispersion containing an active agent by compression-decompression.* EP616801, 1994. |
| Ethanol/ether injection | Precipitation of liposome from organic phase into aqueous | Jaafar-Maalej et al. Ethanol injection method for hydrophilic and lipophilic drug-loaded liposome preparation. *Journal of Liposome Research.* 2010, 20: 3, 228-243.<br>Santo et al. Liposomes Size Engineering by Combination of Ethanol Injection and Supercritical Processing. *J Pharm Sci.* 2015, 104(11), 3842-3850.<br>Batzri and Korn. Single bilayer vesicles prepared without sonication. *Biochim Biophys Acta.* 1973, 298, 1015-1019.<br>Deamer and Bangham. Large volume liposomes by an ether vaporization method. *Biochim Biophys Acta-Biomembr.* 1976, 443(3), 629-634. |
| Crossflow method | In-line Precipitation of liposome from organic phase into aqueous | Wagner et al. GMP Production of Liposomes - A New Industrial Approach. *Journal of Liposome Research.* 2006, 16: 3, 311-319.<br>Wagner et al. Liposomes produced in a pilot scale: production, purification and efficiency aspects. *European Journal of Pharmaceutics and Biopharmaceutics.* 2002, 54, 213-219.<br>Wagner et al. The crossflow injection technique: An improvement of the ethanol injection method. *Journal of Liposome Research.* 2002, 12: 3, 259-270.<br>Wagner and Vorauer-Uhl. Liposome Technology for Industrial Purposes. *Journal of Drug Delivery.* 2011, 2011, DOI: 10.1155/2011/591325.<br>Wagner et al. Enhanced protein loading into liposomes by the multiple crossflow injection technique. *Journal of Liposome Research.* 2002, 12: 3, 271-283. |

Generally, strategies for liposome synthesis focus on addressing and optimizing one or several of the key driving forces of vesicle assembly including the component solubilities, concentrations, and process thermodynamic parameters (e.g., temperature, pressure, etc.) (Mozafari (2005). *Cell Mol Biol Let.*, 10(4), pp. 711-719, Maherani et al. (2011). *Current Nanoscience*. 7(3), pp. 436445, each of which is incorporated by reference herein in its entirety for all purposes). Manufacture methods can be designed to fine-tune liposomes with various properties and, in doing so, can lend both advantages and disadvantages amenable to large-scale processing. In addition, selection of the manufacturing method often depends on the end product requirements for clinically efficacy including liposome size and size distribution, lipid composition, and the API release characteristics, together, which dictate the pharmacokinetic demonstration of adsorption, distribution, metabolism, and elimination (ADME).

The earliest methods for liposome formation began with multistep synthetic strategies involving the rehydration of thin phospholipid films in aqueous media which resulted in the spontaneous formation of lipid structures of varying sizes, shapes, and lamella (Bangham et al. The action of steroids and streptolysin S on the permeability of phospholipid structures to cations. *J Mol. Biol.* 1965, 13, 253-259; Bangham et al. Diffusion of univalent ions across the lamellae of swollen phospholipids. *J. Mo. Biol.* 1965, 13, 238-252; Deamer and Bangham. Large volume liposomes by an ether vaporization method. *Biochimica et Biophysica Aca.* 1976, 443, 629-634). For uniform product generation, these suspensions required post-formation mechanical size manipulations strategies (Barnadas-Rodriguez and Sabes. Factors involved in the production of liposomes with a high-pressure homogenizer. *Int. J Pharma.* 2001, 213, 175-186: Carugo et al. Liposome production by microfluidics: potential and limiting factors. *Scientific Reports*. 2016, 6, DOI:10.1038/srep25876). More recently, efforts have been dedicated towards investigating the possibility for single-step scalable techniques that involve programmable online flow-based strategies to arrive at the controlled precipitation and subsequent self-assembly of phospholipids into uniform structures, which can be implemented in a regulated pharmaceutical environment (Wagner et al. Production of Liposomes—A New Industrial Approach. *Journal of Liposome Research*. 2006, 16:3, 311-319).

In one embodiment, an alcohol injection or crossflow technique is employed in one of the manufacturing methods provided herein. The liposomes are formed in the first central vessel, e.g., via alcohol injection, or provided to the first central vessel after liposome formulation at an upstream in-line formation step. In one embodiment, one of the liposome formation methods set forth in International patent application publication nos. WO 2007/117550 (crossflow); WO 2007/011940 (crossflow) and/or WO 2004/110346 (alcohol injection), each of which is incorporated by reference herein in its entirety for all purposes, is employed herein in an initial liposome formation step.

In alcohol injection and/or crossflow liposomal formation embodiments, dissolved lipids are precipitated from an organic solvent into an aqueous solution (anti-solvent) by means of reciprocal diffusion of the alcohol and aqueous phases (FIGS. 1-2) (Jaafar-Maalej et al. Ethanol injection method for hydrophilic and lipophilic drug-loaded liposome preparation. *Journal of Liposome Research*. 2010, 20:3, 228-243; Wagner et al. Liposomes produced in a pilot scale: production, purification and efficiency aspects. *European Journal of Pharmaceutics and Biopharmaceutics*. 2002, 54, 213-219; Wagner et al. The crossflow injection technique: An improvement of the ethanol injection method. *Journal of Liposome Research*. 2002, 12:3, 259-270; Wagner and Vorauer-Uhl. Liposome Technology for Industrial Purposes. *Journal of Drug Delivery*. 2011, 2011, DOI: 10.1155/2011/591325; Wagner et al. Enhanced protein loading into liposomes by the multiple crossflow injection technique. *Journal of Liposome Research*. 2002, 12:3, 271-283). A change in the local solubility of the lipids during this process ultimately leads to the spontaneous formation of liposomes that encapsulate a small volume of the aqueous solution. Depending on the chemical nature of the API, it can be encapsulated in the aqueous core or embedded in the lipid bilayer of the liposome. Parameters for the formation of liposomes by this method are residence time and geometry of the mixing/intersection of organic-solvated lipid and the antisolvent, which are dictated by programmed flow conditions. After liposome formation, the mixture containing undesired organic solvent and unencapsulated API can then be refined to the desired formulation strength and composition using TFF or similar methods, as set forth herein.

It should be noted that the supercritical fluid and dense gas methods use their namesakes as the solvent for the lipid solution while the injection and crossflow method use organic solvents. Without wishing to be bound by theory, it is thought that supercritical and dense gas feed solutions require high pressure that would be difficult adapt to a continuous design (Meure et al. Conventional and dense gas technology for the production of liposomes: A review. *AAPS Pharma. Sci. Tech.* 2008, 9(3), 798-809; Santo et al. Liposomes Size Engineering by Combination of Ethanol Injection and Supercritical Processing. *J Pharm Sci*. 2015, 104 (11), 3842-3850; Santo et al. Liposomes preparation using a supercritical fluid assisted continuous process. *Chemical Engineering Journal*. 2014, 249, 153-159; Campardelli et al. Efficient encapsulation of proteins in submicro liposomes using a supercritical fluid assisted continuous process. *The Journal of Supercritical Fluids*. 2016, 107, 163-169: Frederiksen et al. Preparation of Liposomes Encapsulating Water-Soluble Compounds Using Supercritical Carbon Dioxide. *Journal of Pharmaceutical Sciences*. 1997, 86(8), 921-928; Otake et al. Development of a new preparation method of liposomes using supercritical carbon dioxide. *Langmuir*. 2001, 17(13), 3898-3901; Anton et al. *Preparation of a liposome dispersion containing an active agent by compression-decompression*. EP616801, 1994). With continuous formulation of the feed solutions, the liposome formation step can proceed indefinitely. By adding continuous steps, continuous manufacturing of liposomal API products can be carried out.

In one aspect, the present invention provides a method for continuous manufacture of a liposomal product comprising an active pharmaceutical ingredient (API) encapsulated by a liposome, or complexed with a liposome. In some embodiments, the API is an aminoglycoside. In a further embodiment, the aminoglycoside is amikacin, or a pharmaceutically acceptable sat thereof.

A "pharmaceutically acceptable salt" includes both acid and base addition salts. A pharmaceutically acceptable addition salt refers to those salts which retain the biological effectiveness and properties of the free bases, which are not biologically or otherwise undesirable, and which are formed with inorganic acids such as, but are not limited to, hydrochloric acid (HCl), hydrobromic acid, sulfuric acid, nitric acid, phosphoric acid and the like, and organic acids such as, but not limited to, acetic acid, 2,2-dichloroacetic acid, adipic acid, alginic acid, ascorbic acid, aspartic acid, benzenesulfonic acid, benzoic acid, 4-acetamidobenzoic acid, camphoric acid, camphor-10-sulfonic acid, capric acid, caproic acid, caprylic acid, carbonic acid, cinnamic acid, citric acid, cyclamic acid, dodecylsulfuric acid, ethane-1,2-disulfonic acid, ethanesulfonic acid, 2-hydroxyethanesulfonic acid, formic acid, fumaric acid, galactaric acid, gentisic acid, glucoheptonic acid, gluconic acid, glucuronic acid, glutamic acid, glutaric acid, 2-oxo-glutaric acid, glycerophosphoric acid, glycolic acid, hippuric acid, isobutyric acid, lactic acid (e.g., as lactate), lactobionic acid, lauric acid, maleic acid, malic acid, malonic acid, mandelic acid, methanesulfonic acid, mucic acid, naphthalene-1,5-disulfonic acid, naphthalene-2-sulfonic acid, 1-hydroxy-2-naphthoic acid, nicotinic acid, oleic acid, orotic acid, oxalic acid, palmitic acid, pamoic acid, propionic acid, pyroglutamic acid, pyruvic acid, salicylic acid, 4-aminosalicylic acid, sebacic acid, stearic acid, succinic acid, acetic acid (e.g., as acetate), tartaric acid, thiocyanic acid, p-toluenesulfonic acid, trifluoroacetic acid (TFA), undecylenic acid, and the like. In one embodiment, the pharmaceutically acceptable salt is HCl, TFA, lactate or acetate.

A pharmaceutically acceptable base addition salt retains the biological effectiveness and properties of the free acids, which are not biologically or otherwise undesirable. These salts are prepared from addition of an inorganic base or an organic base to the free acid. Salts derived from inorganic bases include, but are not limited to, the sodium, potassium, lithium, ammonium, calcium, magnesium, iron, zinc, copper, manganese, aluminum salts and the like. Inorganic salts include the ammonium, sodium, potassium, calcium, and magnesium salts. Salts derived from organic bases include, but are not limited to, salts of primary, secondary, and tertiary amines, substituted amines including naturally occurring substituted amines, cyclic amines and basic ion exchange resins, such as ammonia, isopropylamine, trimethylamine, diethylamine, triethylamine, tripropylamine, diethanolamine, ethanolamine, deanol, 2-dimethylaminoethanol, 2-diethylaminoethanol, dicyclohexylamine, lysine, arginine, histidine, caffeine, procaine, hydrabamine, choline, betaine, benethamine, benzathine, ethylenediamine, glucosamine, methylglucamine, theobromine, triethanolamine, tromethamine, purines, piperazine, piperidine, N-ethylpiperidine, polyamine resins and the like. Organic bases that can be used to form a pharmaceutically acceptable salt include isopropylamine, diethylamine, ethanolamine, trimethylamine, dicyclohexylamine, choline and caffeine.

The term "unit operation" is a term of art and means a functional step that can be performed in a process of manufacturing a liposomal encapsulated API. For example, a unit of operation can be mixing a lipid and API to form a liposomal encapsulated API, filtering (e.g., removal of contaminant bacteria, removal of free API, removal of free lipid, etc., from a fluid containing a liposomal encapsulated API), adjusting the ionic concentration and/or pH of a fluid containing the liposomal encapsulated API, removing unwanted salts.

The unit operations downstream of liposome formation in the continuous manufacturing processes provided herein are used to refine the liposomal API formulation to the desired specification. Frequently, unit operations such as TFF are used to remove undesired elements, such as non-encapsulated API or organic solvent, and concentrate the liposomal API formulation to a final desired strength. In this case, the retentate contains the liposomal API formulation and the permeate acts as a waste stream. See, e.g., FIGS. 3-6 for Examples of processes that can be employed in the methods provided herein.

Figure 2:
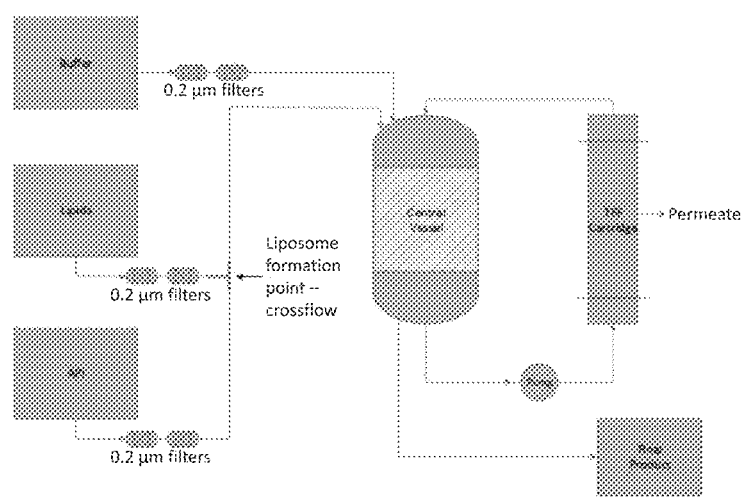
FIG. 2 is a liposomal API manufacturing process flow diagram. Crossflow method: solvent/anti-solvent mix in-line at an intersection point. Formulations are refined in multi-step buffer exchange diafiltration and concentration steps.

In embodiments provided herein, TFF for the buffer exchange and concentration in liposomal API formulation manufacturing is balanced to support continuous operation. A batch mode design for this operation entails a TFF step where the liposome-containing retentate is returned to the central vessel and the permeate/waste stream is made up with a feed of fresh buffer (constant-weight diafiltration), facilitating the buffer exchange. Once buffer exchange is complete, the product is concentrated to the desired strength by ceasing buffer addition (FIGS. 1, 2). In contrast, in particular embodiments provided herein, continuous buffer exchange and/or a concurrent concentration step are employed.

Figure 3:
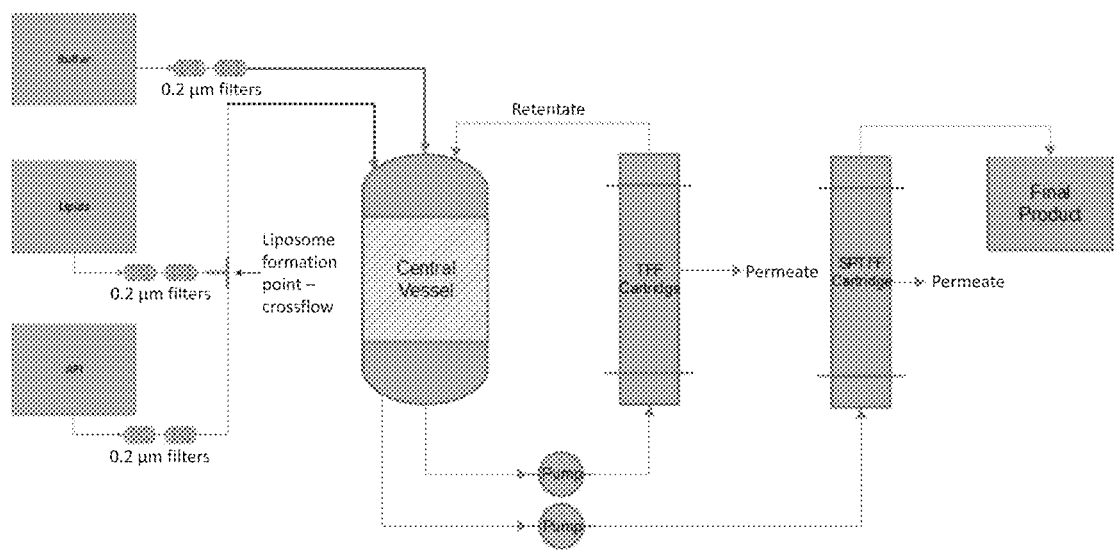
FIG. 3 is a process design for continuous liposome API manufacturing. Single tank buffer exchange tangential flow filtration (TFF) and single stage concurrent concentrating single-pass tangential flow filtration (SPTFF).
Figure 4:
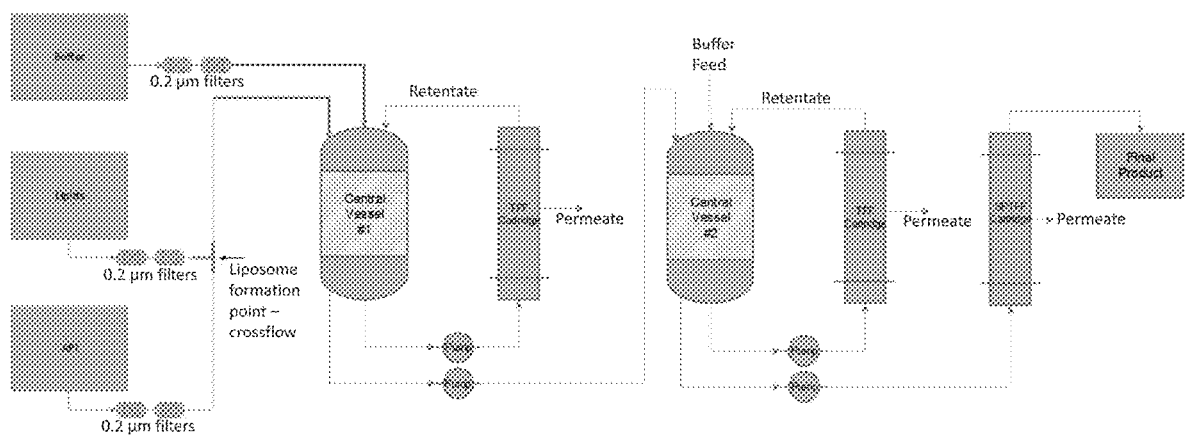
FIG. 4 is a process design for continuous liposome API manufacturing. Continuous multistage (multi-vessel) buffer exchange TFF and single stage concurrent concentrating SPTFF.
Figure 5:
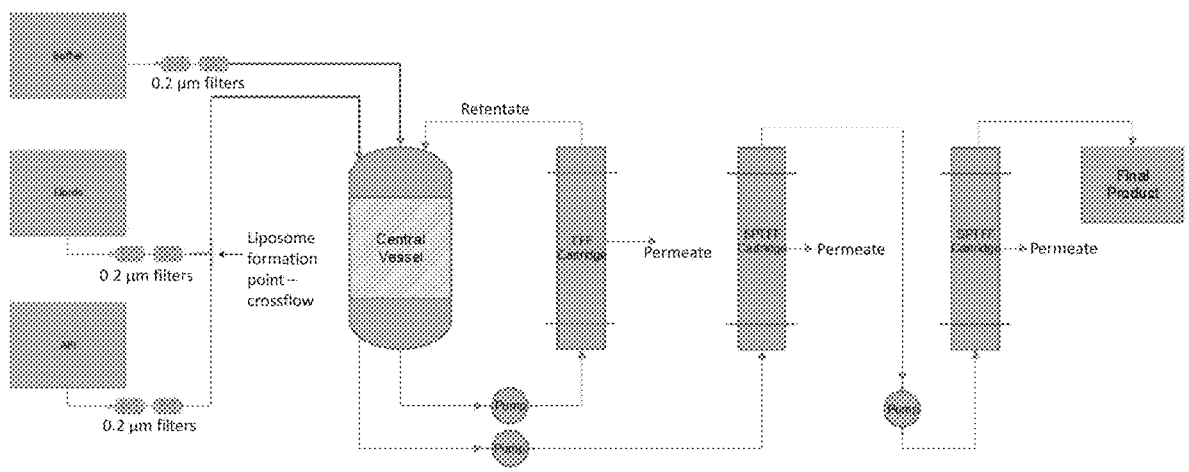
FIG. 5 is a process design for continuous liposome API manufacturing. Single tank buffer exchange TFF and multistage concurrent concentrating SPTFF.
Figure 6:
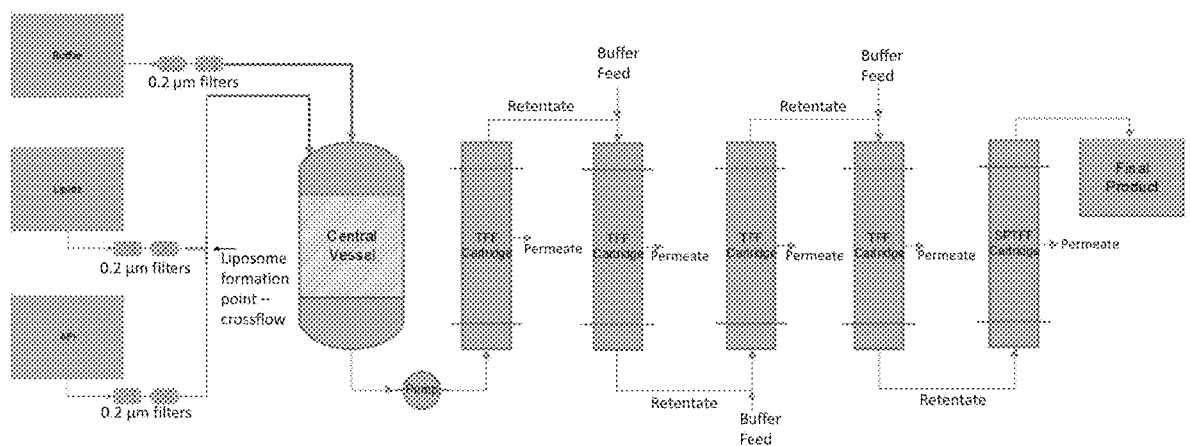
FIG. 6 is a process design for continuous liposome API manufacturing. Multistage buffer exchange (in-line diafiltration (ILDF)) with concurrent concentrating SPTFF.

Depending on the composition of the incoming feeds and specification of the desired end formulation, various arrangements for a continuous operation can be employed. A single vessel buffer exchange TFF system with single stage concurrent concentrating SPTFF serves as one embodiment for a continuous design (FIG. 3). If steady state diafiltration or single pass concentration are not able to achieve the required rate of buffer exchange or concentration with a single stage, additional stages may be added (FIGS. 4, 5). Additionally, more compact designs for continuous buffer exchange, such as the Cadence™ In-line Diafiltration Module (ILDF), are becoming available and can be employed in a continuous liposomal manufacturing process provided herein (see, e.g., Gjoka et al. (2017) Platform for Integrated Continuous Bioprocessing. *BioPharm International.* 30:7, pp. 26-32, incorporated by reference herein in its entirety for all purposes). An ILDF design concluding with SPTFF, without wishing to be bound by theory, is thought to eliminate the need for multiple vessels to support continuous buffer exchange (FIG. 6). Moreover, the ILDF design in FIG. 6 can be modified, e.g., to include additional TFF units in series and/or parallel, for example, an additional, 1, 2, 3, 4, 5 or 6 TFF Units in series and/or parallel. Other ILDF system architectures amenable for use with the methods provided herein are found in U.S. Patent Application Publication No. 2017/0225123, the disclosure of which is incorporated by reference herein in its entirety for all purposes.

During manufacturing of liposomal formulations, there is allowable and expected variability in capture efficiency of the API. In a batch process, this is compensated for by offline in-process measurement of active ingredient concentration prior to the concentration step. Measurements such as flow rates, mass, and density provide a level of control that can be implemented in a continuous operation provided herein. In another embodiment, real-time concentration measurement such as in-line high performance liquid chromatography (HPLC) is employed. In another embodiment, rapid HPLC, which reduces off-line testing time from 60 minutes to 4 minutes is employed to measure concentration of liposomal API product during the manufacturing process (Kumar, V., Joshi, V., A Rapid HPLC Method for Enabling PAT Application for Processing of GCSF. *LCGC North America.* 2013, 31:11, 948-953, incorporated by reference herein in its entirety for all purposes). Other in-line measurements, such as particle size, in one embodiment, are employed. Particle size measurements, in one embodiment, are used to correlate size to concentration of the liposomal API product.

In one embodiment provided herein, the continuous manufacturing process is set up using pre-sterilized componentry and/or steam-in-place (SIP) equipment, and the feed solutions (API containing aqueous solution, lipid in organic solvent, or buffer) must enter the system through sterilizing filters containing a pore size of typically 0.2 µm or less. In one embodiment, the capability (ability of the filter to remove given concentrations of organism) and/or duration (time of use before grow-through of an organism compromises the filter) of the sterile filtration step is validated prior to implementing one or both in the continuous manufacturing methods provided herein. In one embodiment of the methods provided herein, a massively redundant filtration design or a sequential use of a parallel filtration pathways is employed. Without wishing to be bound by theory, it is thought that sequential use of parallel pathways is a viable solution since multiple redundant pathways can cause significant pressure drop issues.

In one embodiment, the API encapsulated by the liposomal manufacturing processes provided herein is an antiinfective. Antiinfectives are agents that act against infections, such as bacterial, mycobacterial, fungal, viral or protozoal infections. Antiinfectives that can be liposomally encapsulated by the methods provided herein include but are not limited to aminoglycosides (e.g., streptomycin, gentamicin, tobramycin, amikacin, netilmicin, kanamycin, and the like), tetracyclines (such as chlortetracycline, oxytetracycline, methacycline, doxycycline, minocycline and the like), sulfonamides (e.g., sulfanilamide, sulfadiazine, sulfamethaoxazole, sulfisoxazole, sulfacetamide, and the like), paraaminobenzoic acid, diaminopyrimidines (such as trimethoprim, often used in conjunction with sulfamethoxazole, pyrazinamide, and the like), quinolones (such as nalidixic acid, cinoxacin, ciprofloxacin and norfloxacin and the like), penicillins (such as penicillin G, penicillin V, ampicillin, amoxicillin, bacampicillin, carbenicillin, carbenicillin indanyl, ticarcillin, azlocillin, mezlocillin, piperacillin, and the like), penicillinase resistant penicillin (such as methicillin, oxacillin, cloxacillin, dicloxacillin, nafcillin and the like), first generation cephalosporins (such as cefadroxil, cephalexin, cephradine, cephalothin, cephapirin, cefazolin, and the like), second generation cephalosporins (such as cefaclor, cefamandole, cefonicid, cefoxitin, cefotetan, cefuroxime, cefuroxime axetil; cefmetazole, cefprozil, loracarbef, ceforanide, and the like), third generation cephalosporins (such as cefepime, cefoperazone, cefotaxime, ceftizoxime, ceftriaxone, ceftazidime, cefixime, cefpodoxime, ceftibuten, and the like), other beta-lactams (such as imipenem, meropenem, aztreonam, clavulanic acid, sulbactam, tazobactam, and the like), betalactamase inhibitors (such as clavulanic acid), chlorampheriicol, macrolides (such as erythromycin, azithromycin, clarithromycin, and the like), lincomycin, clindamycin, spectinomycin, polymyxin B, polymixins (such as polymyxin A. B, C, D, E1(colistin A), or E2, colistin B or C, and the like) colistin, vancomycin, bacitracin, isoniazid, rifampin, ethambutol, ethionamide, aminosalicylic acid, cycloserine, capreomycin, sulfones (such as dapsone, sulfoxone sodium, and the like), clofazimine, thalidomide, or any other antibacterial agent that can be lipid encapsulated. Antiinfectives can include antifungal agents, including polyene antifungals (such as amphotericin B, nystatin, natamycin, and the like), flucytosine, imidazoles (such as n-ticonazole, clotrimazole, econazole, ketoconazole, and the like), triazoles (such as itraconazole, fluconazole, and the like), griseofulvin, terconazole, butoconazole ciclopirax, ciclopirox olamine, haloprogin, tolnaftate, naftifine, terbinafine, or any other antifungal that can be lipid encapsulated or complexed. Discussion and the examples are directed primarily toward amikacin but the scope of the application is not intended to be limited to this antiinfective. Combinations of APIs can be used.

In one embodiment, the API is an aminoglycoside, quinolone, a polyene antifungal or a polymyxins.

In one embodiment, the API is an aminoglycoside. In a further embodiment, the aminoglycoside is an aminoglycoside free base, or its salt, solvate, or other non-covalent derivative. In a further embodiment, the aminoglycoside is amikacin. Included as suitable aminoglycosides used in the API formulations of the present invention are pharmaceutically acceptable addition salts and complexes of APIs. In cases where the compounds may have one or more chiral centers, unless specified, the present invention comprises each unique racemic compound, as well as each unique nonracemic compound. In cases in which the active agents have unsaturated carbon-carbon double bonds, both the cis (Z) and trans (E) isomers are within the scope of this invention. In cases where the active agents exist in tautomeric forms, such as keto-enol tautomers, each tautomeric form is contemplated as being included within the invention. Amikacin, in one embodiment, is present in the pharmaceutical formulation as amikacin base, or amikacin salt, for example, amikacin sulfate or amikacin disulfate. In one embodiment, a combination of one or more of the above aminoglycosides is used in the formulations, systems and methods described herein. In a further embodiment, the combination comprises amikacin.

In one embodiment, the API is amikacin, or a pharmaceutically acceptable salt thereof. In a further embodiment, the amikacin is amikacin sulfate.

In yet another embodiment, the API is an aminoglycoside selected from amikacin, apramycin, arbekacin, astromicin, capreomycin, dibekacin, framycetin, gentamicin, hygromycin B, isepamicin, kanamycin, neomycin, netilmicin, paromomycin, rhodestreptomycin, ribostamycin, sisomicin, spectinomycin, streptomycin, tobramycin, verdamicin, or a combination thereof.

In yet another embodiment, the API is an aminoglycoside selected from AC4437, amikacin, apramycin, arbekacin, astromicin, bekanamycin, boholmycin, brulamycin, capreomycin, dibekacin, dactimicin, etimicin, framycetin, gentamicin. H107, hygromycin, hygromycin B, inosamycin, K-4619, isepamicin, KA-5685, kanamycin, neomycin, netilmicin, paromomycm, plazomicin, ribostamycin, sisomicm, rhodestreptomycin, sorbistin, spectinomycin, sporaricin, streptomycin, tobramcin, verdamicin, vertilmicin, or a combination thereof.

In one embodiment, the API comprises a glycopeptide antibiotic. Glycopeptide antibiotics, including vancomycin and teicoplanin, are large, rigid molecules that inhibit a late stage in bacterial cell wall peptidoglycan synthesis. Glycopeptides are characterized by a multi-ring peptide core containing six peptide linkages, an unusual triphenyl ether moiety, and sugars attached at various sites. Over 30 antibiotics designated as belonging to the glycopeptide class have been reported. Among the glycopeptides, vancomycin and teicoplanin are used widely and are recommended for treatment of severe infections, especially those caused by multiple-drug-resistant Gram-positive pathogens. The glycopeptide avoparcin has been introduced as a growth promoter in animal husbandry in the past, and represents the main reservoir for the VanA type of vancomycin resistance in enterococci. Semisynthetic derivatives of vancomycin and teicoplanin, lipoglycopeptides, showed an extended spectrum of activity against multi-resistant and partly vancomycin-resistant bacteria (Reynolds (1989). Eur. J. Clin Microbiol Infect Dis 8, pp. 943-950; Nordmann et al. (2007). Curr. Opin. Microbiol. 10, pp. 436-440). Each of the publications referenced in this paragraph are incorporated by reference herein in their entireties.

Glycopeptide antibiotics are active against Gram-positive organisms and a few anaerobes. The main indications for glycopeptide antibiotics are infections caused by beta-lactamase-producing *Staphylococcus aureus* (for which beta-lactamase-resistant penicillins, cephalosporins, and combinations of penicillins with inhibitors of beta-lactamases proved safer alternatives), and colitis caused by *Clostridium difficile*. The emergence and rapid spread of methicillin-resistant *S. aureus* (MRSA) strains, which were resistant not only to all beta-lactams but also to the main antibiotic classes, renewed the interest in vancomycin and pushed teicophalnin, another natural glycopeptide, onto the market. Teicoplanin is comparable to vancomycin in terms of activity, but presents pharmacokinetic advantages, such as prolonged half-life, allowing for a once-daily administration (van Bambeke F., Curr. Opin. Pharm., 4(5):471-478).

A representative number of glycopeptides that can be used in the compositions of the present invention are provided in Table 2. The antibiotic complexes are listed in alphabetical order along with the structure type producing organism. These metabolites are elaborated by a diverse group of actinomycetes ranging from the more prevalent *Streptomyces* species to the relatively rare genera of *Streptosporangium* and *Saccharomnonospora*. The less common *Actionplanes* and *Amycolatopsis* account for almost half of the producing oranisms (Nagarajan, R., Glycopeptide Antibiotics, CRC Press. 1994, incorporated by reference herein in its entirety).

TABLE 2

Glycopeptide Antibiotics and Producing Organisms

| Antibiotic | Type | Producing Organism |
| --- | --- | --- |
| A477 | ND | *Actinoplanes* sp. NRRL 3884 |
| A35512 | III | *Streptomyces candidus* NRRL 8156 |
| A40926 | IV | *Actinomadura* sp. ATTC39727 |
| A41030 | III | *Streptomyces virginiae* NRRL 15156 |
| A42867 | I | *Nocardia* sp. ATTC 53492 |
| A47934 | III | *Streptomyces toyocaensis* NRRL 15009 |
| A80407 | III | *Kibdelosporangium philippinensis* NRRL 18198 or NRRL 18199 |
| A82846 | I | *Amycolatopsis orientalis* NRRL 18100 |
| A83850 | I | *Amycolatopsis albus* NRRL 18522 |
| A84575 | I | *Streptosporangium carneum* NRRL 18437, 18505 |
| AB-65 | ND | *Saccharomonospora viride* T-80 FERM-P 2389 |
| Actaplanin | III | *Actinoplanes missouriensis* ATCC 23342 |
| Actinoidin | II | *Proactinomyces actinoides* |
| Ardacin | IV | *Kibdelosporangium aridum* ATCC 39323 |
| Avoparcin | II | *Streptomyces candidus* NRRL 3218 |
| Azureomycin | ND | *Pseudonocardia azurea* NRRL11412 |
| Chloroorienticin | I | *Amyclolatopsis orientalis* PA-45052 |
| Chloropolysporin | II | *Micropolyspora* sp. FERM BP-538 |
| Decaplanin | I | *Kibdelosporangium deccaensis* DSM 4763 |
| N-demethylvancomycin | I | *Amycolatopsis orientalis* NRRL 15252 |
| Eremomycin | I | *Actinomycetes* sp. INA 238 |
| Galacardin | II | *Actinomycetes* strain SANK 64289 FERM P-10940 |
| Helvecardin | II | *Pseudonocardia compacta* subsp. *helvetica* |
| Izupeptin | ND | *Norcardia* AM-5289 FERM P-8656 |
| Kibdelin | IV | *Kibdelosporangium aridum* ATCC 39922 |
| LL-AM374 | ND | *Streptomyces eburosporeus* NRRL 3582 |
| Mannopeptin | ND | *Streptomyces platenis* FS-351 |
| MM45289 | I | *Amycolatopsis orientalis* NCIB12531 |
| MM47761 | I | *Amycolatopsis orientalis* NCIB 12608 |
| MM47766 | II | *Amycolatopsis orientalis* NCBI 40011 |
| MM55266 | IV | *Amycolatopsis* sp. NCIB 40089 |
| MM55270 | ND | *Amycolatopsis* sp. NCIB 40086 |
| OA-7653 | I | *Streptomyces hygromscopicus* ATCC 31613 |
| Orienticin | I | *Nocardia orientalis* FERM BP-1230 |
| Parvodicin | IV | *Actinomadura parvosata* ATCC 532463 |
| Ristocetin | III | *Amycolatopsis orientalis* subsp. *lurida* NRRL 2430 |
| Ristomycin | III | *Proactinomyces fructiferi* |
| Synmonicin | II | *Synnemomyces mamnoorii* ATCC 53296 |
| Teicoplanin | IV | *Actinoplanes teichomyceticus* ATCC 31121 |
| UK-68597 | III | *Actinoplanes* ATCC 53533 |
| UK-69542 | III | *Saccharothix aerocolonigenes* |
| UK-72051 | I | *Amycolatopsis orientalis* |
| Vancomycin | I | *Amycolatoposis orientalis* NRRL 2450 |

According to another embodiment, the glycopeptide antibiotic used in the composition of the present invention includes, but is not limited to, A477, A35512, A40926, A41030 A42867 A47934, A80407, A82846, A83850, A84575, AB-65, Actaplanin, Actinoidin, Ardacin, Avoparcin, Azureomycin, Chloroorienticin Chloropolysporin, Decaplanin, N-demethylvancomycin, Eremomycin, Galacardin, Helvecardin Izupeptin, Kibdelin, LL-AM374, Mannopeptin, MM45289, MM47761, MM47766, MM55266, MM55270, OA-7653 Orienticin, Parvodicin, Ristocetin, Ristomycin, Synmonicin, Teicoplanin, UK-68597, UK-69542, UK-72051, vancomycin, and a mixture thereof.

According to one embodiment, the API is vancomycin. Vancomycin is a water soluble amphoteric glycopeptide bactericidal antibiotic that inhibits gram-positive bacterial mucopeptide biosynthesis. It consists of a tricyclic nonribosomal heptapeptide core structure to which is attached a disaccharide unit consisting of the aminodeoxy sugar, vancosamine, and D-glucose. This natural antibiotic of ~1450 Daltons is obtained from *Streptomyces orientalis* (also known as; *Nocardia onentalis*, or *Amycolatopsis orientalis*). Vancomycin has one carboxyl group with pKa 2.18, and two amino groups: primary amine with pKa 7.75 and the secondary amine with pKa 8.89. At sub-physiological pH vancomycin has a net positive charge.

In another embodiment, the API is oritavancin (LY333328). Oritavancin is obtained by reductive alkylation with 4' chloro-biphenylcarboxaldehyde of the natural glycopeptide chloroeremomycin, which differs from vancomycin by the addition of a 4-epi-vancosamine sugar and the replacement of the vancosamine by a 4-epivancosamine (Cooper, R. et al., J Antibiot (Tokyo) 1996, 49:575-581, incorporated by reference herein in its entirety). Although oritavancin presents a general spectrum of activity comparable to that of vancomycin, it offers considerable advantages in terms of intrinsic activity (especially against streptococci), and remains insensitive to the resistance mechanisms developed by staphylococci and enterococci. Because the binding affinity of vancomycin and oritavancin to free D-Ala-D-Ala and D-Ala-D-Lac are of the same order of magnitude, the difference in their activity has been attributed to the cooperative interactions that can occur between the drug and both types of precursors in situ. The previous study suggested that the effect is caused possibly by a much stronger ability to dimerize and the anchoring in the cytosolic membrane of the chlorobiphenyl side chain (Allen, et al., FEMS Microbiol Rev, 2003, 26:511-532, incorporated by reference herein).

In another embodiment, the API is telavancin (TD-6424). Telavancin is a semi-synthetic derivative of vancomycin, possessing a hydrophobic side chain on the vancosamine sugar (decylaminoethyl) and a (phosphonomethyl) aminomethyl substituent on the cyclic peptidic core (van Bambeke, F., Curr. Opin. Pharm., 4(5): 471478; Judice, J. et al., Bioorg Med Chem Lett 2003, 13: 41654168, incorporated by reference herein in its entirety). The length of the hydrophobic side chain was chosen to reach a compromise between optimized activity against MRSA (8-10 carbons) and VanA enterococci (12-16 carbons). Pharmacological studies suggest that the enhanced activity of telavancin on *S. pneumoniae, S. aureus* (to a lesser extent), and staphylococci or enterococci harboring the vanA gene cluster results from a complex mechanism of action which, on the basis of data obtained with close analogs, involves a perturbation of lipid synthesis and possibly membrane disruption.

In even another embodiment, the API is dalbavancin (BI 397). Dalbavancin is a semi-synthetic derivative of A40926, a glycopeptide with a structure related to that of teicoplanin. As with oritavancin and telavancin, dalbavancin is more active against *S. pneumoniae* than are conventional glycopeptides, and its activity against *S. aureus* is also substantially improved, which was not observed with the semi-synthetic derivatives of vancomycin. However, studies have shown that it is not more active than teicoplanin against enterococci harboring the VanA phenotype of resistance to glycopeptides.

The lipid component used in the continuous manufacturing process described herein in one embodiment, comprises a net neutral lipid, or a combination of net neutral lipids. In one embodiment, the lipid component is free of anionic lipids. In one embodiment, the lipid is a phospholipid, including but not limited to, a phosphatidylcholine such as dipalmitoylphosphatidylcholine or dioleoylphosphatidylcholine; a sterol, including, but not limited to, cholesterol; or a combination of a phosphatidylcholine and a sterol (e.g., cholesterol).

Examples of the lipid component that can be used in preparing the stabilized lipid-based glycopeptide antibiotic composition of the present invention includes, but is limited to, phosphatidylcholine (PC), phosphatidylglycerol (PG), phosphatidylinositol (PI), phosphatidylserine (PS), phosphatidylethanolamine (PE), phosphatidic acid (PA), egg phosphatidylcholine (EPC), egg phosphatidylglycerol (EPG), egg phosphatidylinositol (EPI), egg phosphatidylserine (EPS), phosphatidylethanolamine (EPE), phosphatidic acid (EPA), soy phosphatidylcholine (SPC), soy phosphatidylglycerol (SPG), soy phosphatidylserine (SPS), soy phosphatidylinositol (SPI), soy phosphatidylethanolamine (SPE), soy phosphatidic acid (SPA), hydrogenated egg phosphatidylcholine (HEPC), hydrogenated egg phosphatidylglycerol (HEPG), hydrogenated egg phosphatidylinositol (HEPI), hydrogenated egg phosphatidylserine (HEPS), hydrogenated phosphatidylethanolamine (HEPE), hydrogenated phosphatidic acid (HEPA), hydrogenated soy phosphatidylcholine (HSPC), hydrogenated soy phosphatidylglycerol (HSPG), hydrogenated soy phosphatidylserine (HSPS), hydrogenated soy phosphatidylinositol (HSPI), hydrogenated soy phosphatidylethanolamine (HSPE), hydrogenated soy phosphatidic acid (HSPA), dipalmitolphosphatidylcholine (DPPC), dimyristoylphosphatidylcholine (DMPC), dimyristoylphosphatidylglyccrol (DMPG), dipalmitoylphosphatidylglycerol (DPPG), distearoylphosphatidylcholine (DSPC), distearoylphosphatidylglycerol (DSPG), dioleoylphosphatidylcholine (DOPC), dioleylphosphatidylethanolamine (DOPE), palmitoylstearoylphosphatidylcholine (PSPC), palmitoylstearolphosphatidylglycerol (PSPG), mono-oleoyl-phosphatidylethanolamine (MOPE), tocopherol, tocopherol hemisuccinate, cholesterol sulfate, cholesteryl hemisuccinate, cholesterol derivatives, ammonium salts of fatty acids, ammonium salts of phospholipids, ammonium salts of glycerides, myristylamine, palmitylamine, laurylamine, stearylamine, dilauroyl ethylphosphocholine (DLEP), dimyristoyl ethylphosphocholine (DMEP), dipalmitoyl ethylphosphocholine (DPEP) and distearoyl ethylphosphocholine (DSEP),N-(2, 3-di-(9-(Z)-octadecenyloxy)-prop-1-yl-N,N,N-trimethylammonium chloride (DOTMA), 1, 2-bis(oleoyloxy)-3-(trimethylammonio)propane (DOTAP), distearoylphosphatidylglycerol (DSPG), dimvristoylphosphatidylacid (DMPA), dipalmitoylphosphatidylacid (DPPA), distcarovlphosphatidylacid (DSPA), dimyristoylphosphatidylinositol (DMPI), dipalmitoylphosphatidylinositol (DPPI), distearoylphospatidylinositol (DSPI), dimyristoylphosphatidylserine (DMPS), dipalmitoylphosphatidylserine (DPPS), distearoylphosphatidylserine (DSPS), or a mixture thereof.

In another embodiment, the lipid component used in the continuous manufacturing process of the present invention comprises palmitoylstearoylphosphatidylcholine (PSPC), palmitoylstearoylphosphatidylglycerol (PSPG), triacylglycerol, diacylglycerol, seranide, sphingosine, sphingomyelin, a single acylated phospholipid, such as mono-oleoyl-phosphatidylethanol amine (MOPE), or a combination thereof.

In another embodiment, the lipid component used in the continuous manufacturing process comprises an ammonium salt of a fatty acid, a phospholipid, sterol, a phosphatidylglycerols (PG), a phosphatidic acid (PA), a phosphotidylholine (PC), phosphatidylinositol (PI) or a phosphatidylserine (PS). The fatty acid can be a fatty acids of carbon chain lengths of 12 to 26 carbon atoms that is either saturated or unsaturated. Some specific examples include, but are not limited to, myristylamine, palmitylamine, laurylamine and stearylamine, dilauroyl ethylphosphocholine (DLEP), dimyristoyl ethylphosphocholine (DMEP), dipalmitoyl ethylphosphocholine (DPEP) and distearoyl ethylphosphocholine (DSEP), N-(2, 3-di-(9 (Z)-octadecenyloxy)-prop-1-yl-N,N,N-trimethylammonium chloride (DOTMA) and 1, 2-bis(oleoyloxy)-3-(trimethylammonio) propane(DOTAP).

According to another embodiment, the lipid component comprises a phosphatidylcholine. In a further embodiment, the phosphatidylcholine is dipalmitoylphosphatidylcholine (DPPC) or palmitoyloleoylphosphatidylcholine (POPC). In even a further embodiment, the phosphatidylcholine comprises DPPC.

According to another embodiment, the lipid component comprises a phosphatidylglycerol. In a further embodiment, the phosphatidylglycerol is 1-palmitoyl-2-olcoyl-sn-glycro-3-phosphoglycerol (POPG).

According to another embodiment, the lipid component comprises a sterol, including, but not limited to, cholesterol and ergosterol. In one embodiment, the lipid component comprises a phospholipid and a sterol. In a further embodiment, the sterol is cholesterol.

The lipid-to-API weight ratio of the liposomal encapsulated API provided herein, in one embodiment, is 3 to 1 or less, 2.5 to 1 or less, 2 to 1 or less, 1.5 to 1 or less, or 1 to 1 or less. The lipid to API ratio of the liposomal encapsulated API provided herein, in another embodiment, is less than 3 to 1, less than 2.5 to 1, less than 2 to 1, less than 1.5 to 1, or less than 1 to 1. In a further embodiment, the lipid to API ratio is about 0.7 to 1 or less or about 0.7 to 1. In even a further embodiment, the API is an aminoglycoside, e.g., amikacin or a pharmaceutically acceptable salt thereof.

The lipid-to-API weight ratio (lipid:API) of the liposomal encapsulated API provided herein, in one embodiment, is from about 3:1 to about 0.5:1, from about 2.5:1 to about 0.5:1, from about 2:1 to about 0.5:1, from about 1.5:1 to about 0.5:1, or from about 1:1 to about 0.5:1. In a further embodiment, the API is an aminoglycoside, e.g., amikacin or a pharmaceutically acceptable salt thereof.

EXAMPLES

The present invention is further illustrated by reference to the following Examples. However, it should be noted that the Examples, like the embodiments described above, are illustrative and not to be construed as restricting the scope of the invention in any way.

Example 1—Case Study of Batch and Continuous Liposome Manufacturing Processes

Figure 7:
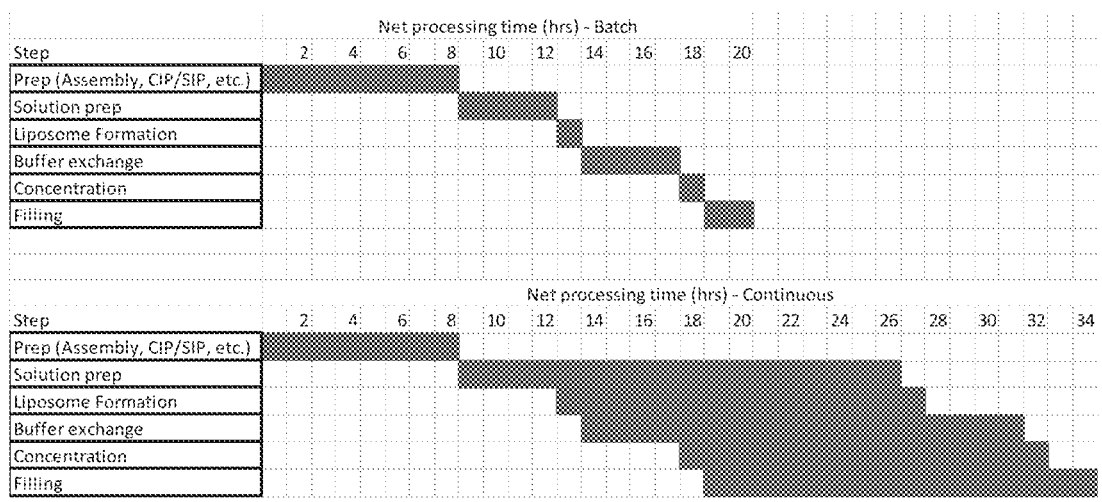
FIG. 7 compares batch vs. continuous processing steps/times for a liposomal API product.

For the purposes of the case study, the following options are compared; (1) a batch process design producing 2500 filled units from a 1 hr. liposome formation step with supporting batch process steps and (2) a continuous process design allowing for a 24 hr. liposome formation step with concurrent continuous unit operations. The batch process is based on a process used for early phase clinical production. It is assumed that the batch and continuous designs are using similar scale equipment with similar processing rates. A summary of the unit operations and processing times is in FIG. 7.

The batch process is able to produce 2500 filled units in 20 hr. of total processing time including preparation (assembly, CIP/SIP, etc.). This calculates to 125 units/hr. The continuous process with a 24 hr. liposome formation step produces 18,750 filled units in 34 hr. of total process time or 551 units/hr. This translates to a 4.4-fold increase in output for the same overhead costs and a 7.5-fold output increase for the same process preparation costs and single-use componentry costs (sterilizing filters, TFF cartridges). This ignores the additional capital expenses needed to achieve one of the continuous designs previously mentioned (e.g., set forth at FIGS. 3-6).

Another way to compare the processes is by their ability to fulfill a given production forecast. For a forecast of 1 million units per year, the continuous design requires the 34-hr. process to be run approximately once per week. For the batch design, the 20-hr. process would have to be run more than once per day, necessitating multiple lines running at a higher rate to fulfill the forecast.

By converting the early phase clinical scale production line to a continuous operation, not only are cost savings and higher throughput achieved, but the need for scaling up the process is alleviated, which eliminates the need for supporting process development work and large-scale capital equipment purchases.

Example 2-Continuous Liposome Manufacturing

This example outlines a continuous inline dialfiltration (ILDF)/concentration of a liposomal amikacin formulation having a lipid component consisting of DPPC and cholesterol. This Example is concerned with understanding the operating conditions/parameters for the continuous in-line diafiltration module.

Equipment and Components

The equipment and components in Table 3 below was used for both experiments executed under this Example. The ILDF setup utilized two standard peristaltic pumps for operations—the first to control the feed and retentate, and the second to control the buffer injection. The ILDF included six fluid treatment modules. A fluid treatment module comprises a filtration membrane, feed channel and permeate channel (i.e., the diagram shown in FIG. 6 with one additional fluid treatment module).

TABLE 3

| Equipment | Manufacturer | Vendor Part No. |
| --- | --- | --- |
| Cadence Inline Diafiltration Module | Pall Corporation | DFOS030T120612 |
| 135 L SS Jacketed Vessel | Sharpsville | 1103 |
| 100 L SS Jacketed Vessel | Lee Industries | B8783-A |
| Tubing Flowpaths with Sensors | Pall Corporation | DFOS030T120612 |
| 1000 L PVDF Vessel | Terracon | Custom |
| Infusion Peristaltic Pumps | Watson Marlow | 520U |
| Masterflex L/S Pumps for Saline (DF control) and Feed/Retentate | Cole-Parmer | EW-07522-20 |
| Masterflex Easy Load II Pump Heads | Cole-Parmer | EW-77201-60 |
| Masterflex L/S cartridge pump head (6 channel, 6 roller) | Cole-Parmer | EW-07519-15 |
| Masterflex L/S pump head cartridges | Cole-Parmer | EW-07519-75 |
| Pressure Monitor (Feed. Retentate) | PendoTECH | PMAT4A-BAR |
| Balance for Raw Material Weighing | Sartorius | Signum 1 |
| Flow Meters | Endress Hauser | 83P08 |

Solution Preparation

Prior to beginning each experiment, all product contact surfaces in the process train were either cleaned using 0.1N NaOH or replaced with new components where appropriate. Post cleaning rinsing with RODI water was completed until neutral pH was achieved. Following cleaning, the amikacin solution and saline was prepared, followed by lipid solution. All raw materials weighed were within expected accuracy from the target. All raw materials weights and additional processing information related to infusion, diafiltration and concentration was recorded during processing. Raw materials for solution preparation are provided in Table 4 below.

TABLE 4

| Solution | Raw Materials | Vendor |
| --- | --- | --- |
| Amikacin | Water | RODI |
|  | Amikacin | ACS Dobfar |
|  | NaOH | J. T. Baker |
| Lipid | Ethanol | PhamcoAaper |
|  | Cholesterol | Dishman |
|  | DPPC | Lipoid |
| Saline | Water | RODI |
|  | NaCl | J. T. Baker |

Amikacin-Lipid Infusion

During processing, the Melfi system records flow rates, pressure, temperature, vessel weight and time. Amikacin and lipid infusion was carried out via an in-line method to create 2 L of a liposomal amikacin suspension, as described in U.S. Pat. No. 7,718,189, the disclosure of which is incorporated by reference herein in its entirety.

Inline Diafiltration

The 2 L of infused material was collected under the skid and processed by ILDF. PendoTECH's custom data acquisition software was used to record and log all process data for the duration of the diafiltration. After ~200 mL of product was diafiltered at one set of flowrates (Trial 1), the pump settings were changed and ~200 mL of product was collected at another set of flowrates (Trial 2). See Table 5 for a summary of process data collected throughout the experiments.

TABLE 5

| | | | | | | | |
|---|---|---|---|---|---|---|---|
| Sample | Infusion Flow rate (mL/min) | Buffer Flow rate (mL/min) | Average Feed Pressure (psi) | Average TMP (psi) | Average Feed Conductivity (mS) | Average Retentate Conductivity (mS) | Avg. Feed Temp (C.) | Avg. Retentate Temp (C.) |
| 1 | 10 | 30 | 25.0 | 0.88 | 6.89 | 454 | 25.3 | 23.6 |
| 2 | 5 | 25 | 24.4 | 0.87 | 6.83 | 364 | 24.7 | 23.7 |

Analytical Results

Table 6 provides the initial analytical results from the experiments.

TABLE 6

Analytical Results Summary

| Sample | Infusion Flowrate | Buffer Flowrate | Amikacin Conc. | Cholesterol Conc. | DPPC Conc. | Lipid-to-API weight ratio |
|---|---|---|---|---|---|---|
| 1 | 10 mL/min | 30 mL/min | 6 mg/mL | 2 mg/mL | 3 mg/mL | 0.83 |
| 2 | 5 mL/min | 25 mL/min | 14 mg/mL | 4 mg/mL | 8 mg/mL | 0.86 |

All publications, protocols, patents and patent applications cited herein are incorporated herein by reference in their entireties for all purposes.

While the described invention has been described with reference to the specific embodiments thereof it should be understood by those skilled in the art that various changes may be made and equivalents may be substituted without departing from the true spirit and scope of the invention. In addition, many modifications may be made to adopt a particular situation, material, composition of matter, process, process step or steps, to the objective spirit and scope of the invention. All such modifications are intended to be within the scope of the claims appended hereto.

The invention claimed is:

1. A method for making a liposomal active pharmaceutical ingredient (API) formulation, comprising,
    mixing a lipid solution comprising a lipid dissolved in an organic solvent with an aqueous API solution, wherein the lipid solution and aqueous API solution are mixed from two separate streams in an in-line fashion, and wherein a liposomal encapsulated API is formed at the intersection of the two streams,
    introducing the liposomal encapsulated API into a first central vessel comprising a first inlet, a second inlet, a first outlet and a second outlet, through the first inlet, wherein the first outlet is in fluid communication with an inlet of a first tangential flow filtration (TFF) unit comprising the inlet and a first and second outlet, wherein the first outlet of the first TFF unit is in fluid communication with the second inlet of the first central vessel and the second outlet of the first TFF unit is a waste (permeate) outlet; and the second outlet of the first central vessel is in fluid communication with an inlet of a second TFF unit comprising the inlet and a first and second outlet, wherein the first outlet of the second TFF unit is a retentate outlet and the second outlet of the second TFF unit is a waste (permeate) outlet;
    continuously flowing the liposomal encapsulated API into the first TFF unit for a first period of time, wherein the liposomal encapsulated API enters the first TFF unit through the TFF inlet and exits through the first outlet;
    flowing the liposomal encapsulated API from the first central vessel through the inlet of the second TFF unit for a second period of time; and
    collecting the liposomal API formulation from the first outlet of the second TFF unit.

2. A method for making a liposomal active pharmaceutical ingredient (API) formulation, comprising,
    mixing a lipid solution comprising a lipid dissolved in an organic solvent with an aqueous API solution, wherein the lipid solution and aqueous API solution are mixed from two separate streams in an in-line fashion, and wherein a liposomal encapsulated API is formed at the intersection of the two streams,
    introducing the liposomal encapsulated API into a first central vessel comprising an inlet and an outlet, through the inlet, wherein the outlet is in fluid communication with an inlet of a first tangential flow filtration (TFF) unit comprising the inlet and a first and second outlet, wherein the first outlet of the first TFF unit is in fluid communication with the inlet of a second TFF comprising the inlet and a first and second outlet, and the second outlet of the first TFF unit is a waste (permeate) outlet; and wherein the first outlet of the second TFF unit is a retentate outlet and the second outlet of the second TFF unit is a waste (permeate) outlet;
    flowing the liposomal encapsulated API into the first TFF unit for a first period of time, wherein the liposomal encapsulated API enters the first TFF unit through the TFF inlet and exits through the first outlet;
    flowing the liposomal encapsulated API from the first outlet of the first TFF through the inlet of the second TFF unit for a second period of time; and
    collecting the liposomal API formulation from the first outlet of the second TFF unit.

3. A method for making a liposomal active pharmaceutical ingredient (API) formulation, comprising,
    mixing a lipid solution comprising a lipid dissolved in an organic solvent with an aqueous API solution, wherein the lipid solution and aqueous API solution are mixed from two separate streams in an in-line fashion, and wherein liposomal encapsulated API is formed at the intersection of the two streams, introducing the liposomal encapsulated API into a first central vessel comprising a first inlet, a second inlet, a first outlet and a second outlet, through the first inlet, wherein the first outlet is in fluid communication with an inlet of a first tangential flow filtration (TFF) unit comprising the inlet and a first and second outlet, wherein the first outlet of the first TFF unit is in fluid communication with the second inlet of the first central vessel and the second outlet of the first TFF unit is a waste outlet; and the second outlet of the first central vessel is in fluid communication with a first inlet of a second central vessel, wherein the second central vessel comprises the first inlet, a second inlet, a first outlet and a second outlet, and the first outlet of the second central vessel is in fluid communication with an inlet of a second tangential flow filtration (TFF) unit comprising the inlet and a first and second outlet, wherein the first outlet of the second TFF unit is in fluid communication with the second inlet of the second central vessel, the second outlet of the second TFF unit is a waste outlet; the second outlet of the second central vessel is in fluid communication with an inlet of a third TFF unit comprising the inlet and a first and second outlet, wherein the first outlet of the third TFF unit is a retentate outlet and the second outlet of the third TFF unit is a waste (permeate) outlet;

continuously flowing the liposomal encapsulated API into the first TFF unit for a first period of time, wherein the liposomal encapsulated API enters the first TFF unit through the TFF inlet and exits through the first outlet;

flowing the liposomal encapsulated API from the first central vessel into the second central vessel for a second period of time;

continuously flowing the liposomal encapsulated API into the second TFF unit from the second central vessel for a third period of time, wherein the liposomal encapsulated API enters the second TFF unit through the TFF inlet and exits through the first outlet;

flowing the liposomal encapsulated API from the second central vessel through the inlet of the third TFF unit for a fourth period of time; and collecting the liposomal encapsulated API formulation from the first outlet of the third TFF unit.

4. The method of claim 2, wherein the mixing results in the formation of an API coacervate.

5. The method of claim 2, wherein a buffer is introduced into the first central vessel through a third inlet prior to the first period of time or during the first period of time.

6. The method of claim 2, wherein the second TFF unit is a single pass TFF unit (SPTFF).

7. The method of claim 5, wherein the buffer is a sodium chloride buffer.

8. The method of claim 2, wherein the lipid comprises a phospholipid.

9. The method of claim 8, wherein the phospholipid is a phosphatidylcholine.

10. The method of claim 9, wherein the phosphatidylcholine is dipalmitoyl phosphatidylcholine (DPPC).

11. The method of claim 2, wherein the lipid comprises cholesterol.

12. The method of claim 2, wherein the lipid consists of DPPC and cholesterol.

13. The method of claim 2, wherein the API is an antiinfective.

14. The method of claim 13, wherein the antiinfective is an aminoglycoside, or a pharmaceutically acceptable salt thereof.

15. The method of claim 14, wherein the aminoglycoside is amikacin, or a pharmaceutically acceptable salt thereof.

16. The method of claim 15, wherein the amikacin is amikacin sulfate.

17. The method of claim 14, wherein the aminoglycoside is AC4437, amikacin, apramycin, arbekacin, astromicin, bekanamycin, boholmycin, brulamycin, capreomycin, dibekacin, dactimicin, etimicin, framycetin, gentamicin, H107, hygromycin, hygromycin B, inosamycin, K-4619, isepamicin, KA-5685, kanamycin, neomycin, netilmicin, paromomycin, plazomicin, ribostamycin, sisomicin, rhodestreptomycin, sorbistin, spectinomycin, sporaricin, streptomycin, tobramycin, verdamicin, vertilmicin, a pharmaceutically acceptable salt thereof, or a combination thereof.

18. The method of claim 16, wherein the lipid-to-API weight ratio of the collected liposomal API formulation is about 0.7 to 1.

19. The method of claim 16, wherein the lipid-to-API weight ratio of the collected liposomal API formulation is from about 3:1 to about 0.5:1, from about 2.5:1 to about 0.5:1, from about 2:1 to about 0.5:1, from about 1.5:1 to about 0.5:1, or from about 1:1 to about 0.5:1.

20. The method of claim 19, wherein lipid consists of DPPC and cholesterol.

* * * * *